United States Patent
Kim et al.

(10) Patent No.: US 9,938,561 B2
(45) Date of Patent: Apr. 10, 2018

(54) METHOD FOR DIAGNOSING CANCER THROUGH DETECTION OF DEGLYCOSYLATION OF GLYCOPROTEIN

(71) Applicant: SEOUL NATIONAL UNIVERSITY R&DB FOUNDATION, Seoul (KR)

(72) Inventors: Youngsoo Kim, Seoul (KR); Jung-Hwan Yoon, Seoul (KR); Hyunsoo Kim, Bucheon-si (KR); Kyunggon Kim, Goyang-si (KR); Jonghwa Jin, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 14/906,799

(22) PCT Filed: Jul. 17, 2014

(86) PCT No.: PCT/KR2014/006479
§ 371 (c)(1),
(2) Date: Jan. 21, 2016

(87) PCT Pub. No.: WO2015/012533
PCT Pub. Date: Jan. 29, 2015

(65) Prior Publication Data
US 2016/0168618 A1 Jun. 16, 2016

(30) Foreign Application Priority Data
Jul. 25, 2013 (KR) .......................... 10-2013-0088006

(51) Int. Cl.
| | | |
|---|---|---|
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *C12Q 1/34* | (2006.01) | |
| *C12Q 1/37* | (2006.01) | |
| *G01N 33/574* | (2006.01) | |

(52) U.S. Cl.
CPC .................. *C12Q 1/34* (2013.01); *C12Q 1/37* (2013.01); *G01N 33/57484* (2013.01); *G01N 2333/98* (2013.01); *G01N 2440/38* (2013.01); *G01N 2560/00* (2013.01); *G01N 2800/7028* (2013.01)

(58) Field of Classification Search
CPC . G06Q 40/08; C12Q 1/34; C12Q 1/37; G01N 2333/98; G01N 2440/38; G01N 2560/00; G01N 2800/7028; G01N 33/57484
See application file for complete search history.

(56) References Cited

U.S. PATENT DOCUMENTS

2006/0269980 A1* 11/2006 Gibbs ...................... C12Q 1/34
435/23
2007/0269895 A1* 11/2007 Aebersold ................ C12Q 1/34
436/56
2015/0346194 A1* 12/2015 Magnelli .............. G01N 33/531
435/7.92

FOREIGN PATENT DOCUMENTS

KR  10-2010-0120788 A  11/2010
KR  10-2012-0125157 A  11/2012

OTHER PUBLICATIONS

Morinaga et al. Primary structures of human alpha-fetoprotein and its mRNA. PNAS, 1983. vol. 80, pp. 4604-4608.*
Whelan et al. Mass spectrometry (LC-MS/MS) site-mapping of N-glycosylated membrane proteins for breast cancer biomarkers. J Proteome Res, 2009. vol. 8. No. 8, pp. 4151-4160.*
Anderson et al. Quantitative Mass Spectrometric Multiple Reaction Monitoring Assays for Major Plasma Proteins. MCP. 2006, pp. 573-588.*
Fujikawa et al. Amino Acid Sequence of Human Factor XI, a Blood Coagulation Factor with Four Tandem Repeats that Are Highly Homologous with Plasma Prekallikrein. Biochemistry, 1986. vol. 25, pp. 2417-2424.*
Ruhaak et al.Developments in the Identification of Glycan Biomarkers for the Detection of Cancer. Molecular and Celular Proteomics, Jan. 30, 2013, 12: 10.10744, pp. 846-855.*
De Leoz et al. High-Mannose Glycans are Elevated during Breast Cancer Progression. Molecular and Cellular Proteomics. Published, MCP Papers in Press, Nov. 19, 2010. 10.1074, pp. 1-9.*
Roth et al. Glycoconjug J. 2010, N-glycan moieties of the crustacean egg yolk protein and their glycosylation sites.vol. 27, pp. 159-169.*

* cited by examiner

*Primary Examiner* — Marcela M Cordero Garcia
(74) *Attorney, Agent, or Firm* — Vorys, Sater, Seymour & Pease LLP; Mih Suhn Koh

(57) ABSTRACT

Provided is a method for diagnosing cancer through a difference with a control group in view of the ratio of a deglycosylated peptide fragment and a non-glycosylated peptide fragment in a protein including an N-linked glycosylation motif. Further provided is a method for diagnosing cancer through the detection of the glycosylation ratio in the protein according to the subject matter enables the diagnosis of cancer with high specificity and sensitivity using at least one existing marker, and can be useful in discovering new markers for diagnosing cancer.

6 Claims, 67 Drawing Sheets

FIG. 2

|P10594| Invertase 1 (INV1)_Saccharomyces cerevisiae (yeast)     SEQ ID NO: 1

MLLQAFLFLLAGFAAKISASMTNETSDRPLVHFTPNKGWMNDPNGLWYDAKEGKWHLYFQVNPNDTVWGLPLFWG
HATSDDLTHWQDEPIAIAPKRKDSGAYSGSMVDYNNTSGFFNDTIDPRQRCVAIWTYNTPESEEQYISYSLDGGYTFT
EYQKNPVLAANSTQFRDPKVFWYEPSKKWIMTAAKSQDYKIEIYSSDDLKSWKLESAFANEGFLGYQYECPGLIEVPS
EQDPSKSHWVMFISINPGAPAGGSFNQYFVGSFNGHHFEAFDNQSRVVDFGKDYYALQTFFNTDPTYGSALGIAWA
SNWEYSAFVPSNPWRSSMSLVRPESLNTEYQANPETELINLKAEPILNISSAGPWSRFATNTTLTKANSYNVDLSNSTG
TLEFELVYAVNTTQTISKSVFADLSLWFKGLEDPEEYLRMGFEVSASSFFLDRGNSKVKFVKENPYFTNRMSVNNQPFKS
ENDLSYKWGLDQNILELYFNDGOVVSTNTYFMTTGNALGSVNMTTGVDNLFYIDKFQVREVK

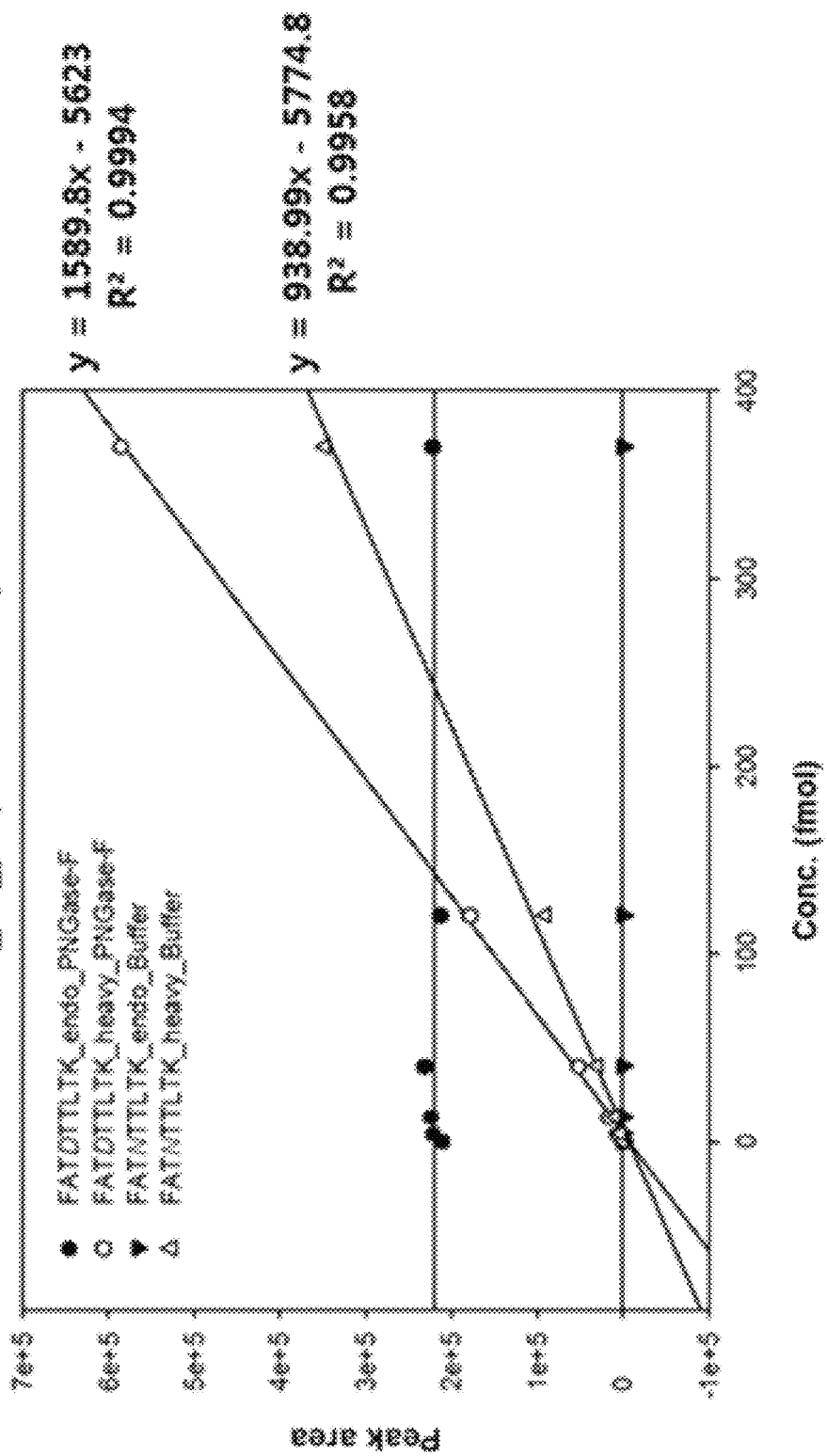

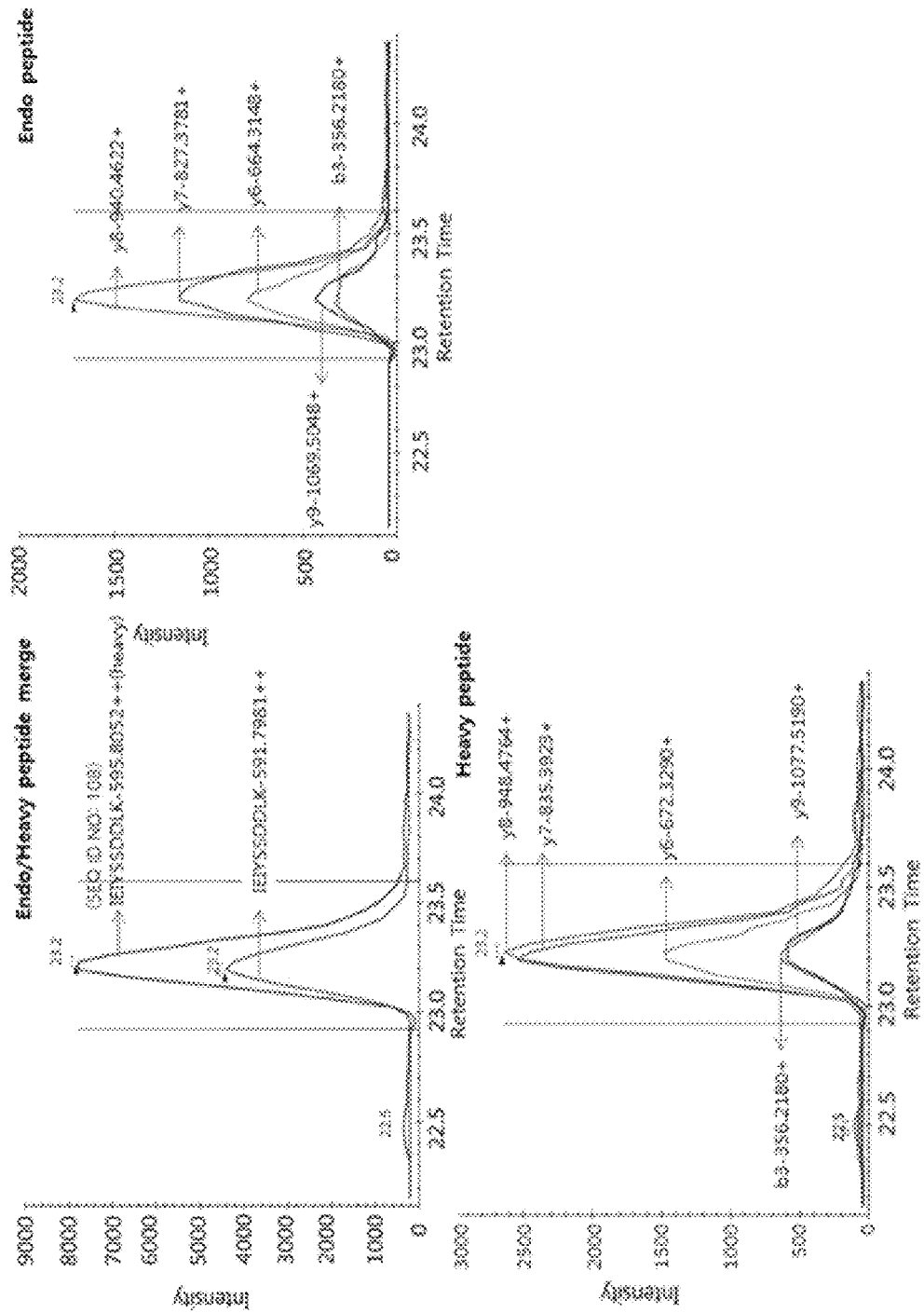

FIG. 8

P02771| Alpha-fetoprotein (AFP)_Homo sapiens (human)        SEQ ID NO: 2

MKWVESIFLIFLLNFTESRTLHRNEYGIASILDSYQCTAEISLADLATIFFAQFVQEATYKEVSKMVKDALTAIEKPTGDEQSS
GCLENQLPAFLEELCHEKEILEKYGHSDCCSQSEEGRHNCFLAHKKPTPASLPEQVPEPVTSCEAYEEDRETFMNKFIYEI
ARRHPFLYAPTILLWAARYDKIIPSCCKAENAVECFQTKAATVTKELRESSLLNQHACAVMKNFGTRTFQAITVTKLSQKF
TKVNFTEIQKLVLDVAHVHEHCCRGDVLDCLQDGEKIMSYICSQQDTLSNKITECCKLTTLERGQCIIHAENDEKPEGLS
PNLNRFLGDRDFNQFSSGEKNIFLASFVHEYSRRHPQLAVSVILRVAKGYQELLEKCFQTENPLECQQKGEEELQKYIQE
SQALAKRSCGLFQKLGEYYLQNAFLVAYTKKAPQLTSSELMAITRKMAATAATCCQLSEDKLLACGEGAADIIIGHLCIRH
EMTPVNPGVGQCCTSSYANRRPCFSSLVVDETYVPPAFSDDKFIFHKDLCQAQGVALQTMKQEFLINLVKQKPQITEEQ
LEAVIADFSGLLEKCCQGQEQEVCFAEEGQKLISKTRAALGV

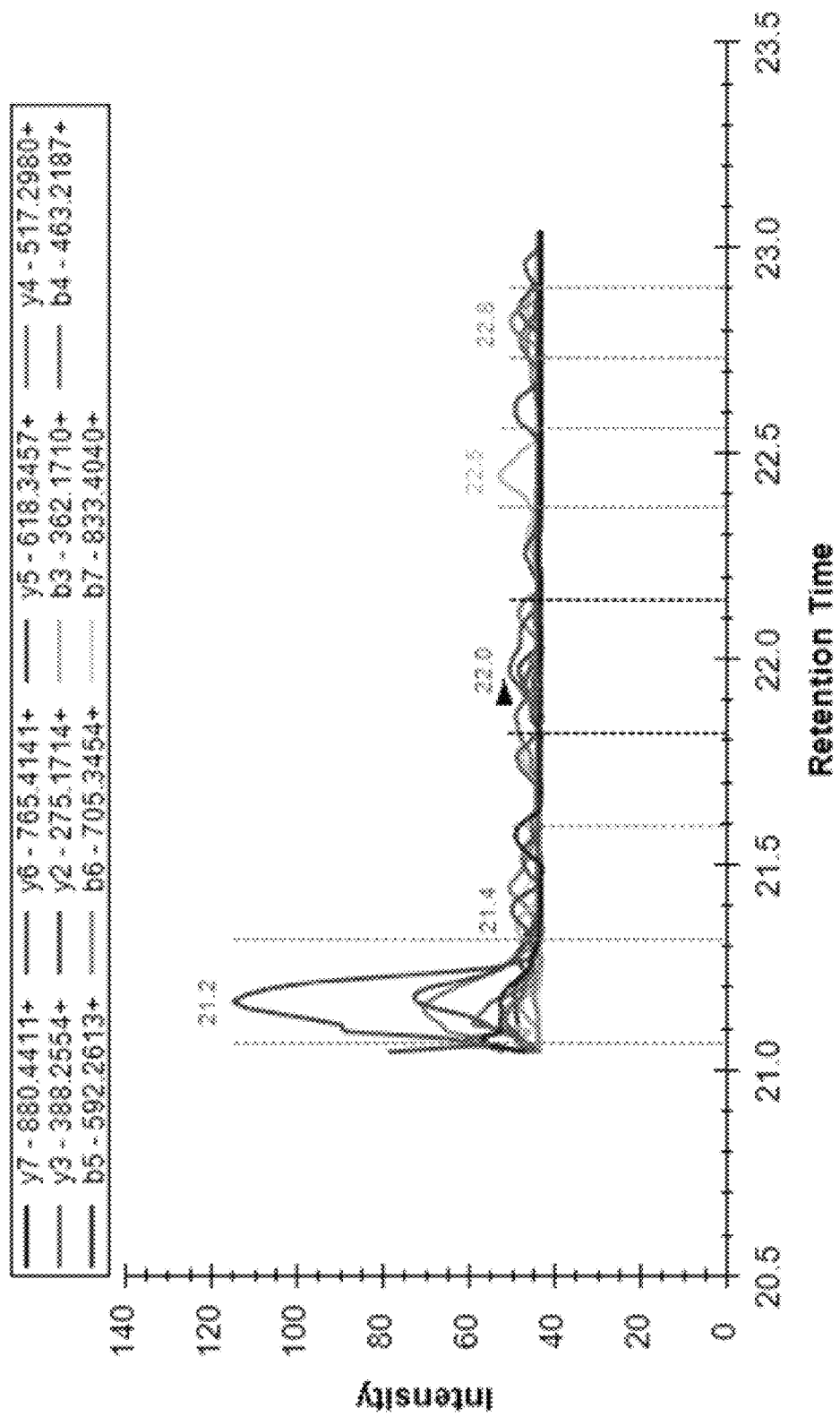

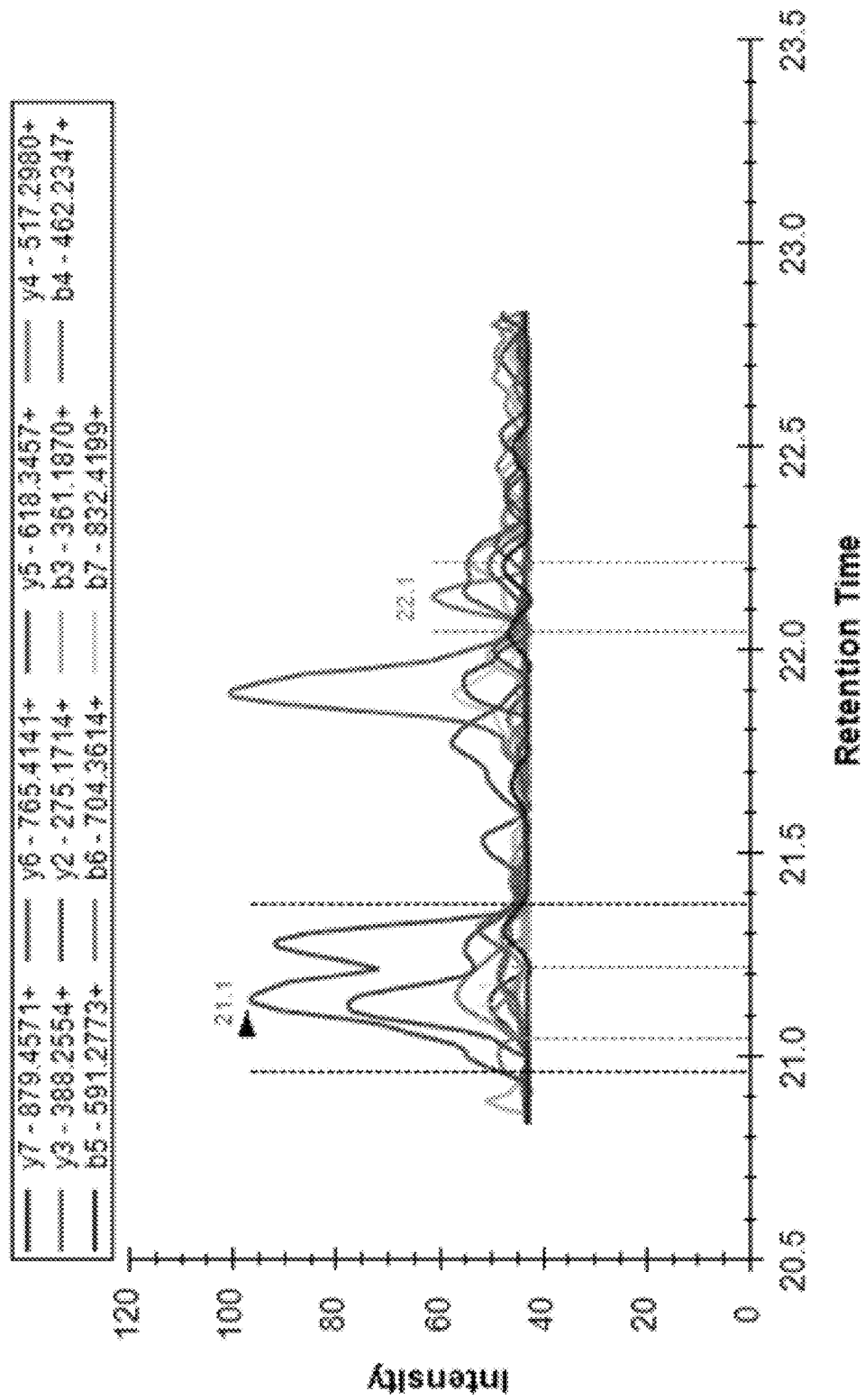

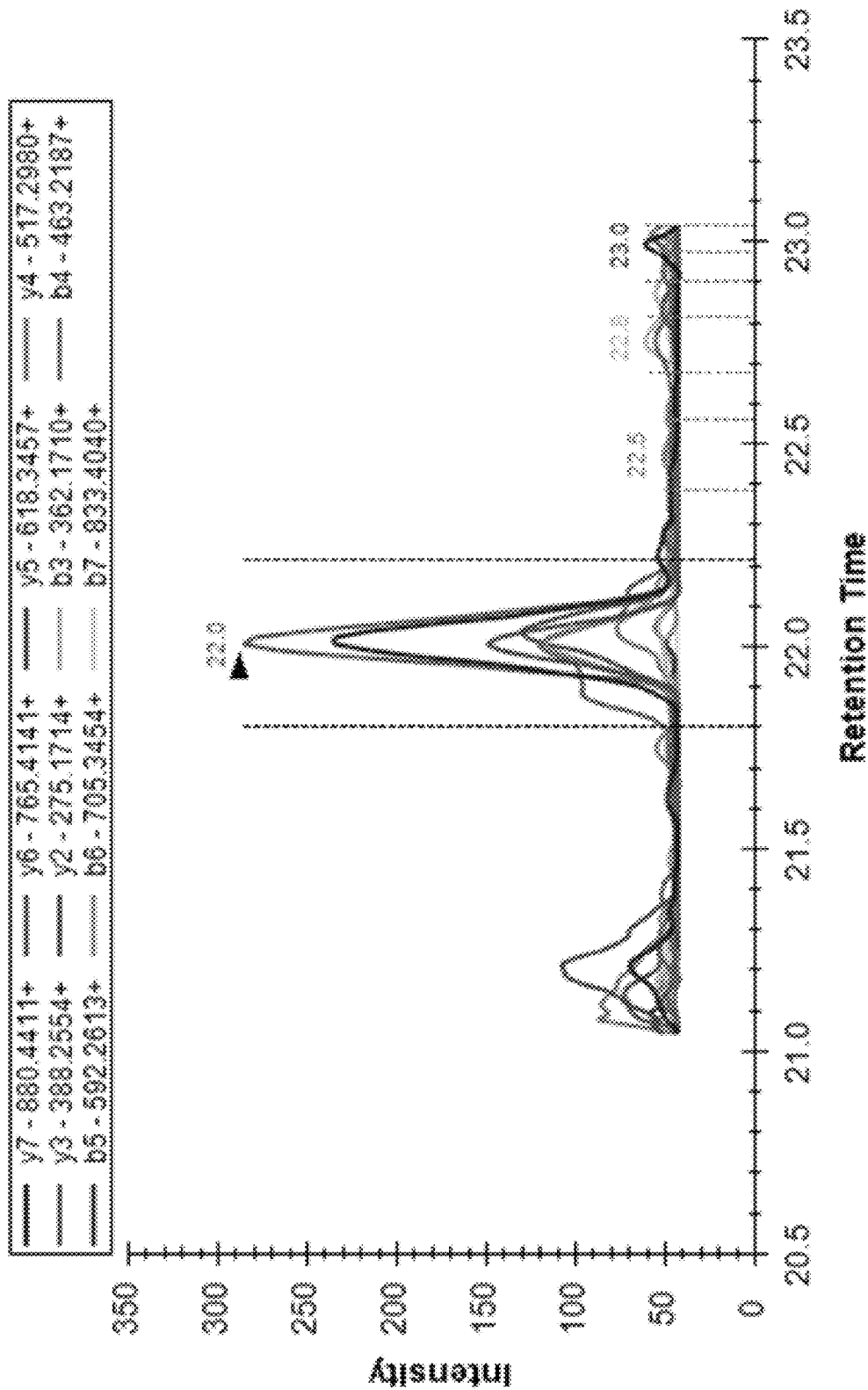

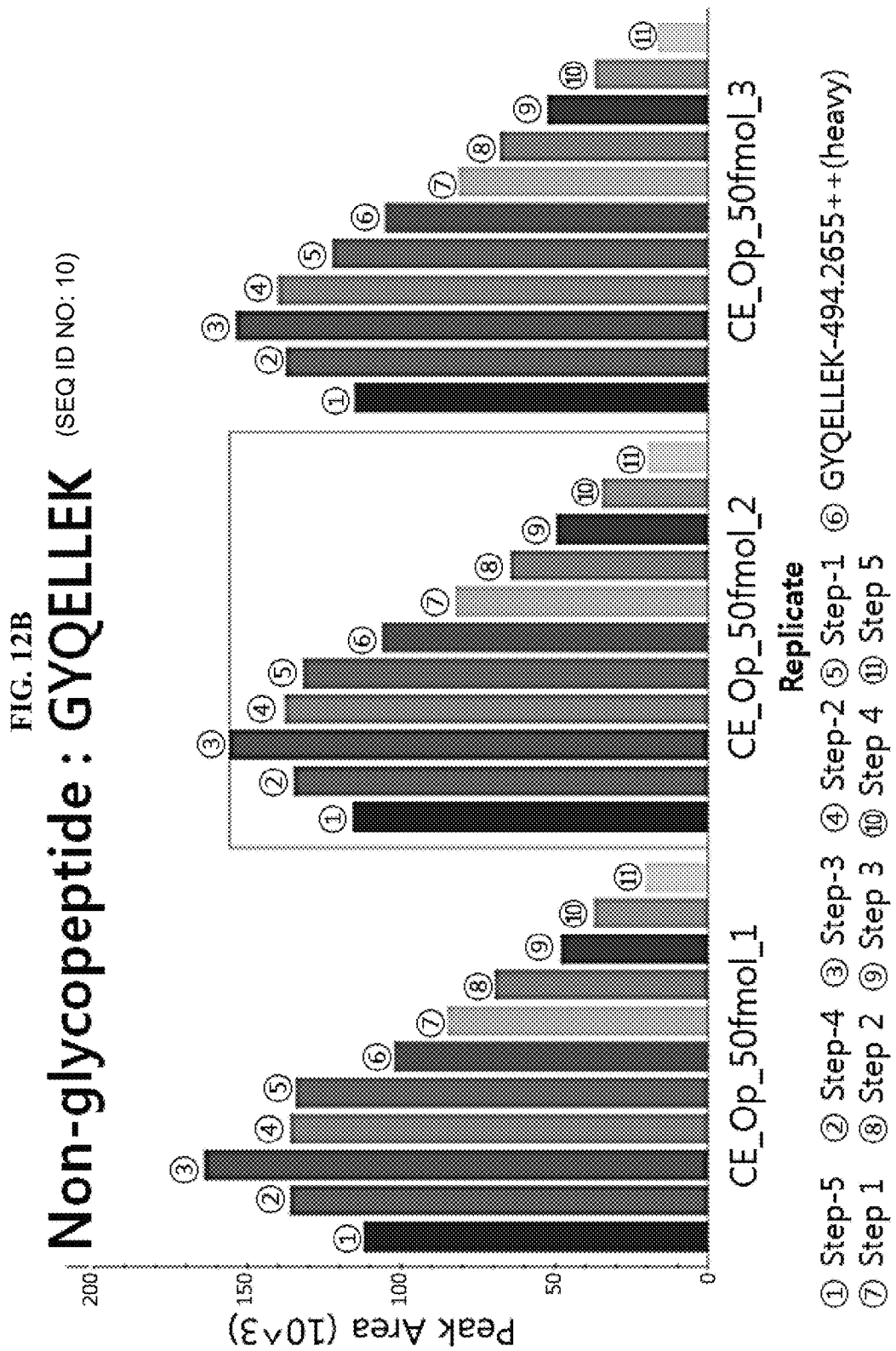

FIG. 14
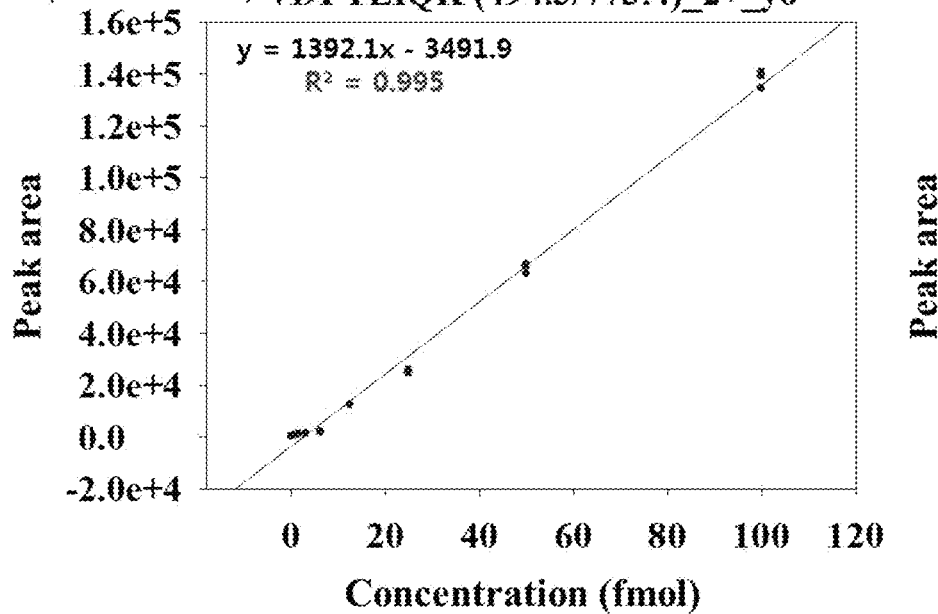
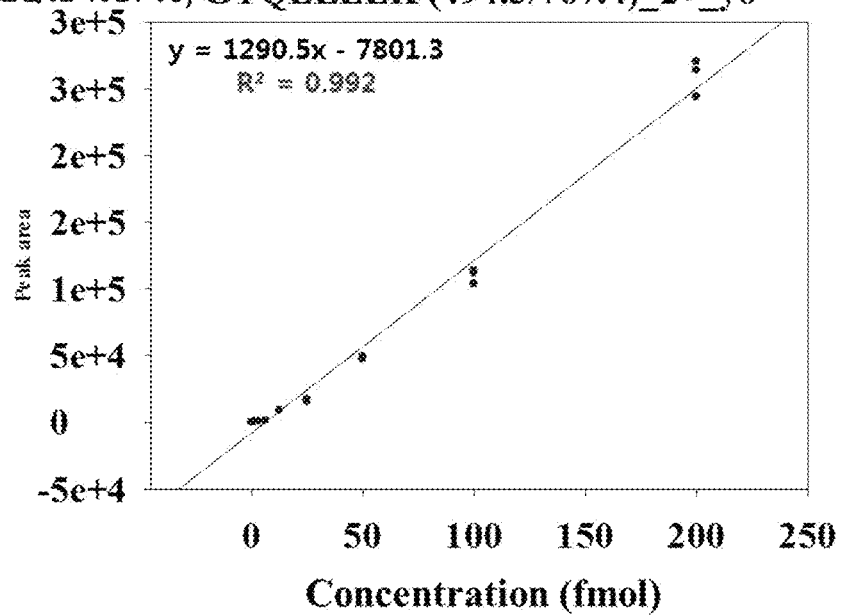

FIG. 15
De-glycopeptide
(SEQ ID NO: 9) V*D*FTEIQK (494.3/773.4)_2+_y6
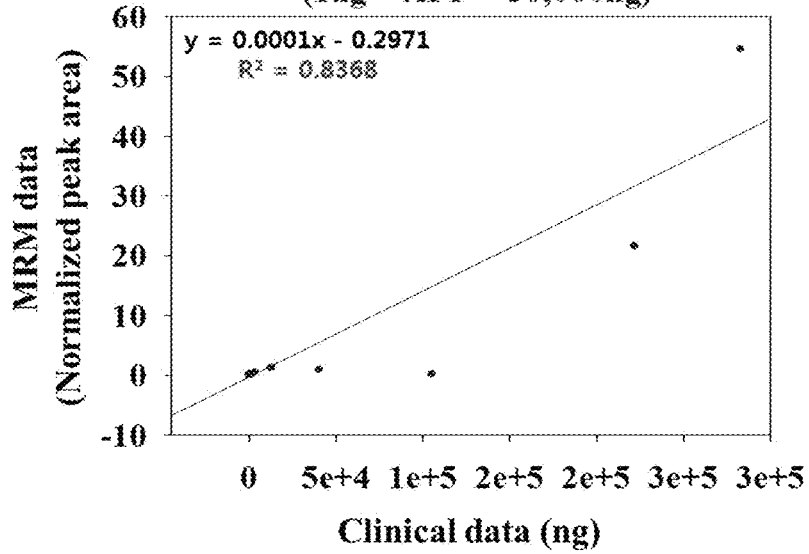
Non-glycopeptide
(SEQ ID NO: 10) GYQELLEK (494.3/767.4)_2+_y6
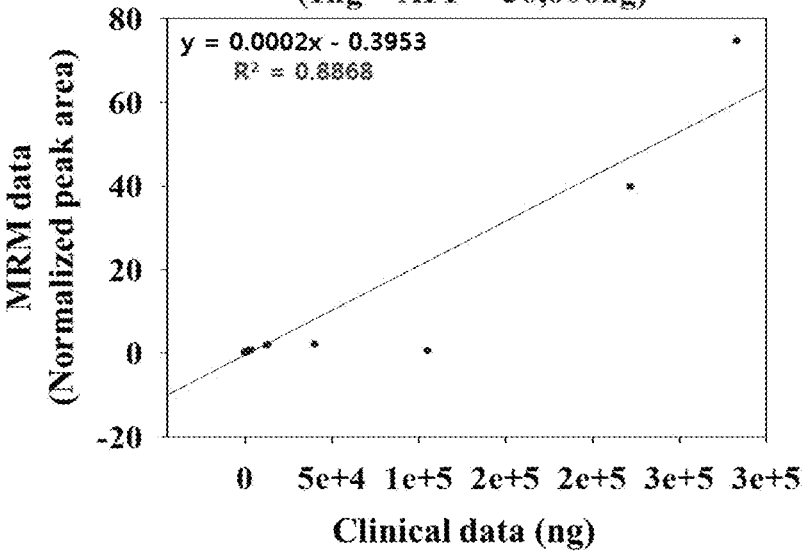

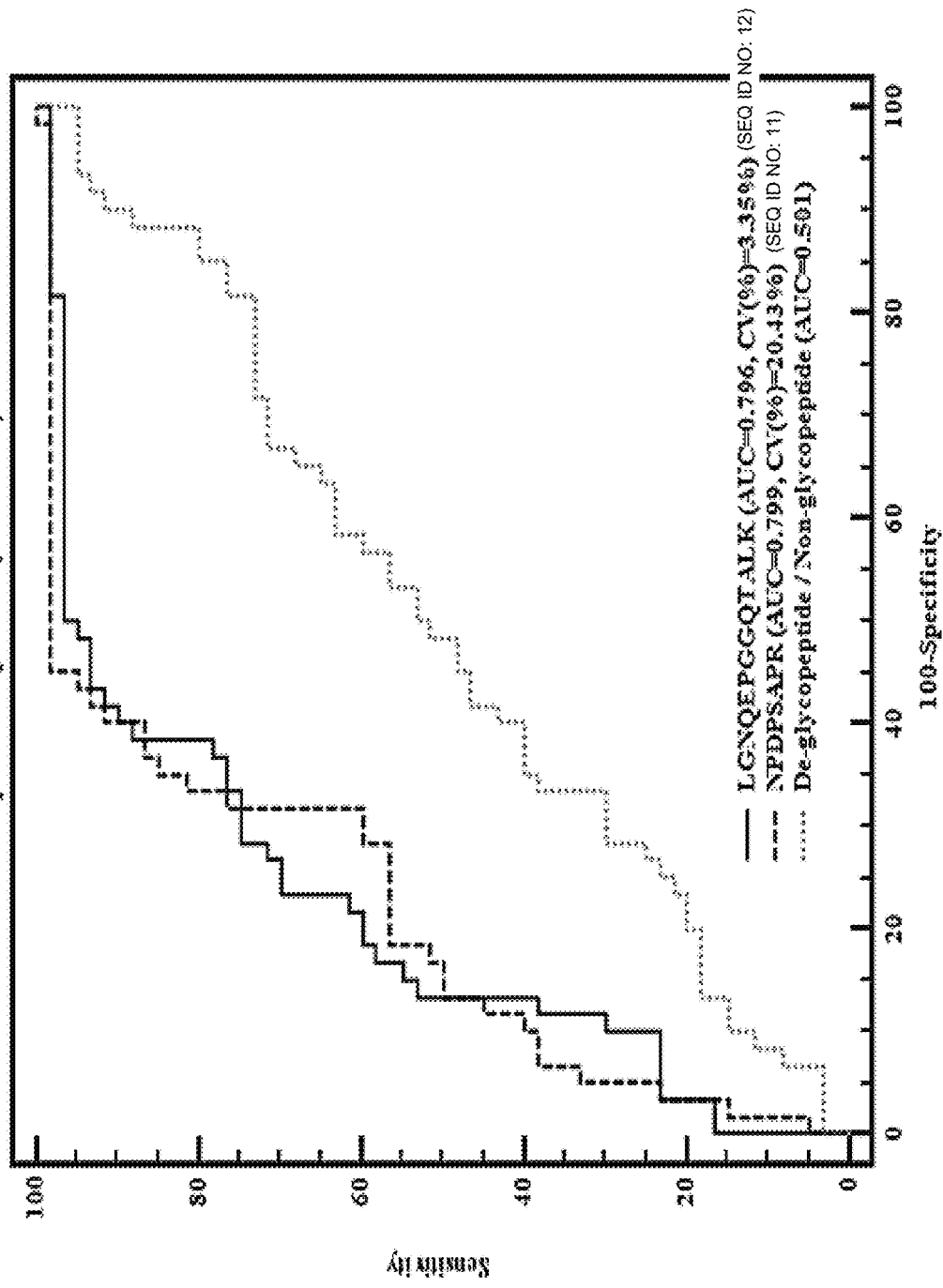

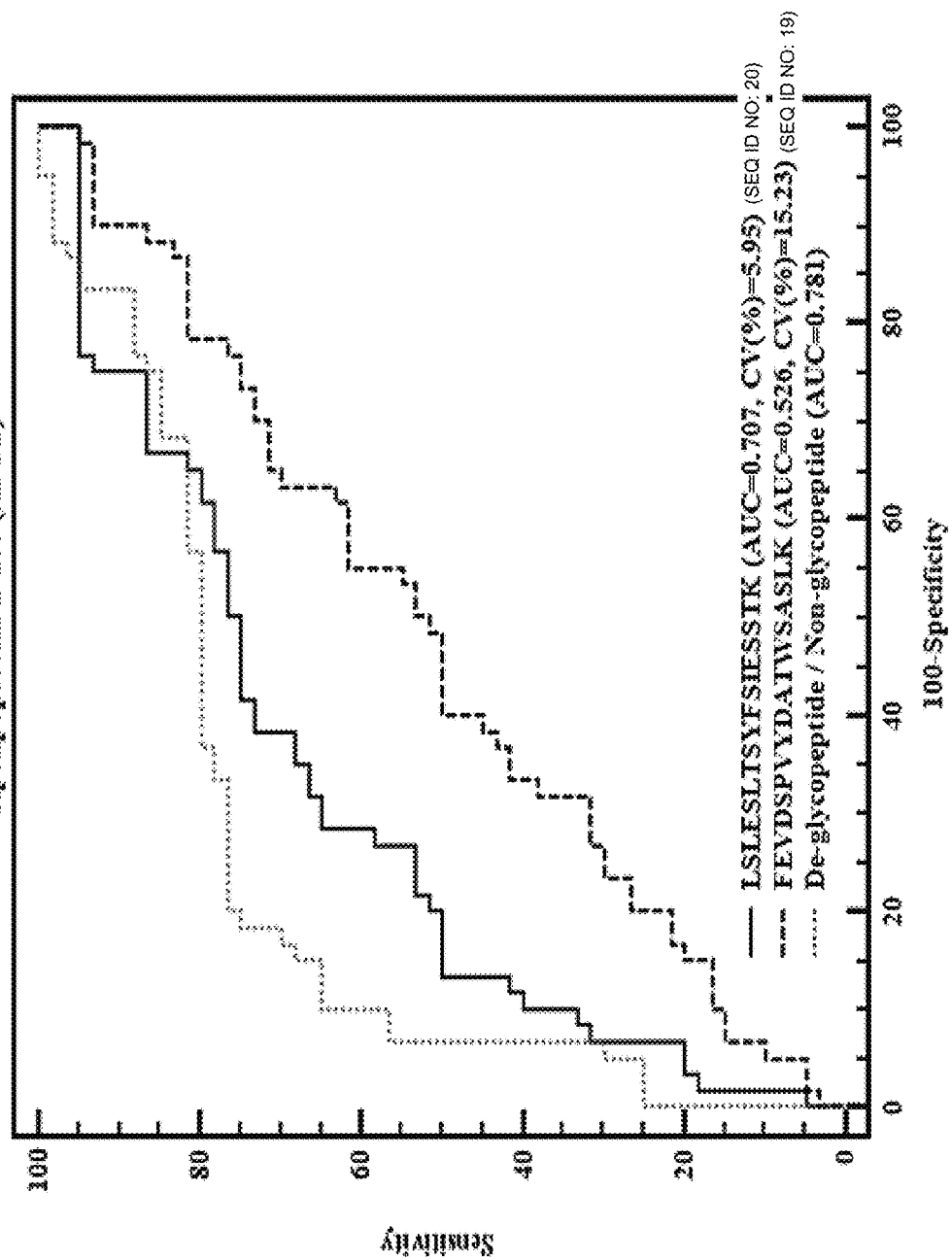

Beta-galactosidase (GLB1)

Bone morphogenetic protein 1 (BMP1)

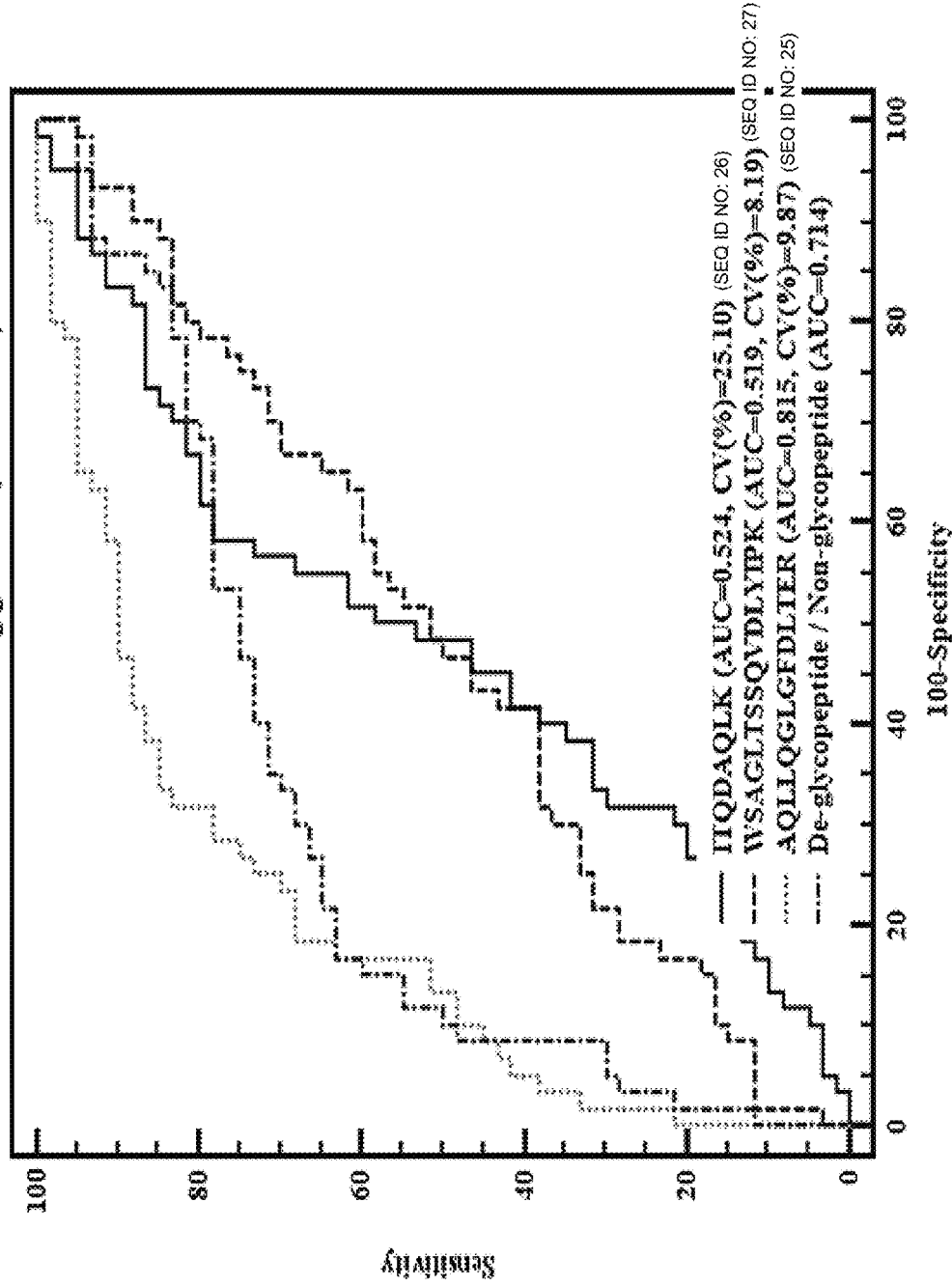

Complement factor H (CFH)

Cholinesterase (BCHE)

Clusterin (CLU)

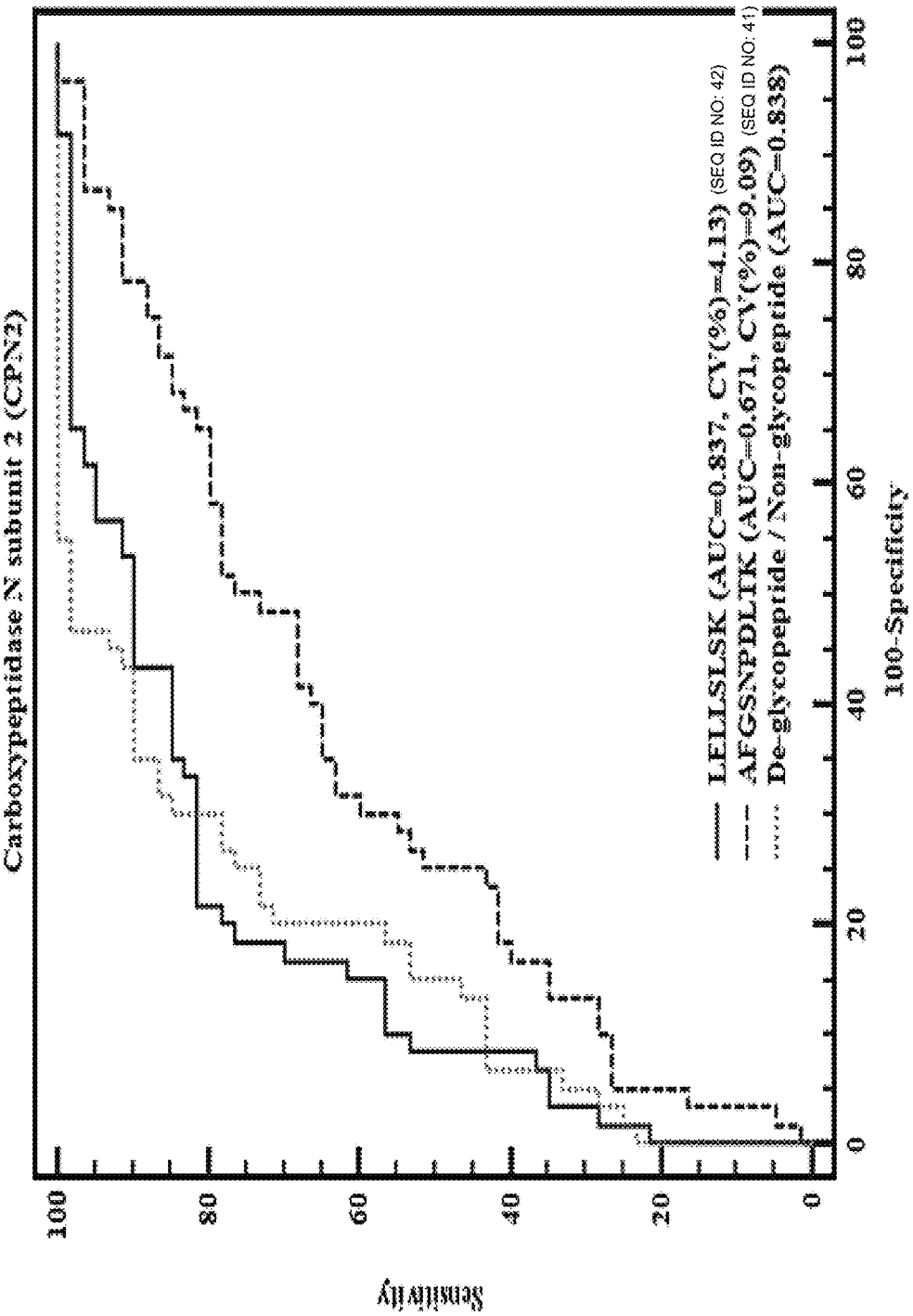

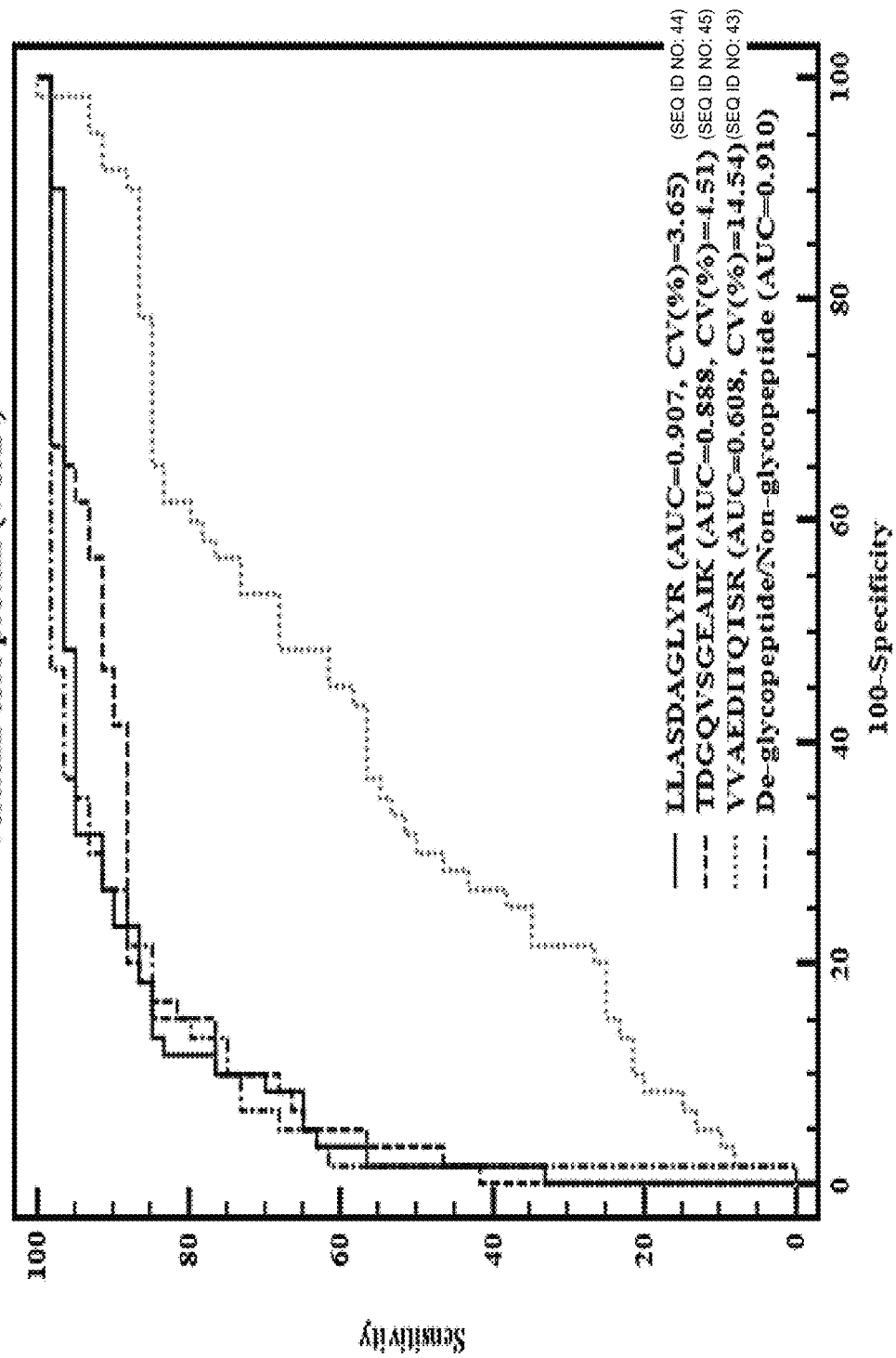

Coagulation factor V (F5)

Coagulation factor XI (F11)

Follistatin-related protein 1 (FSTL1)

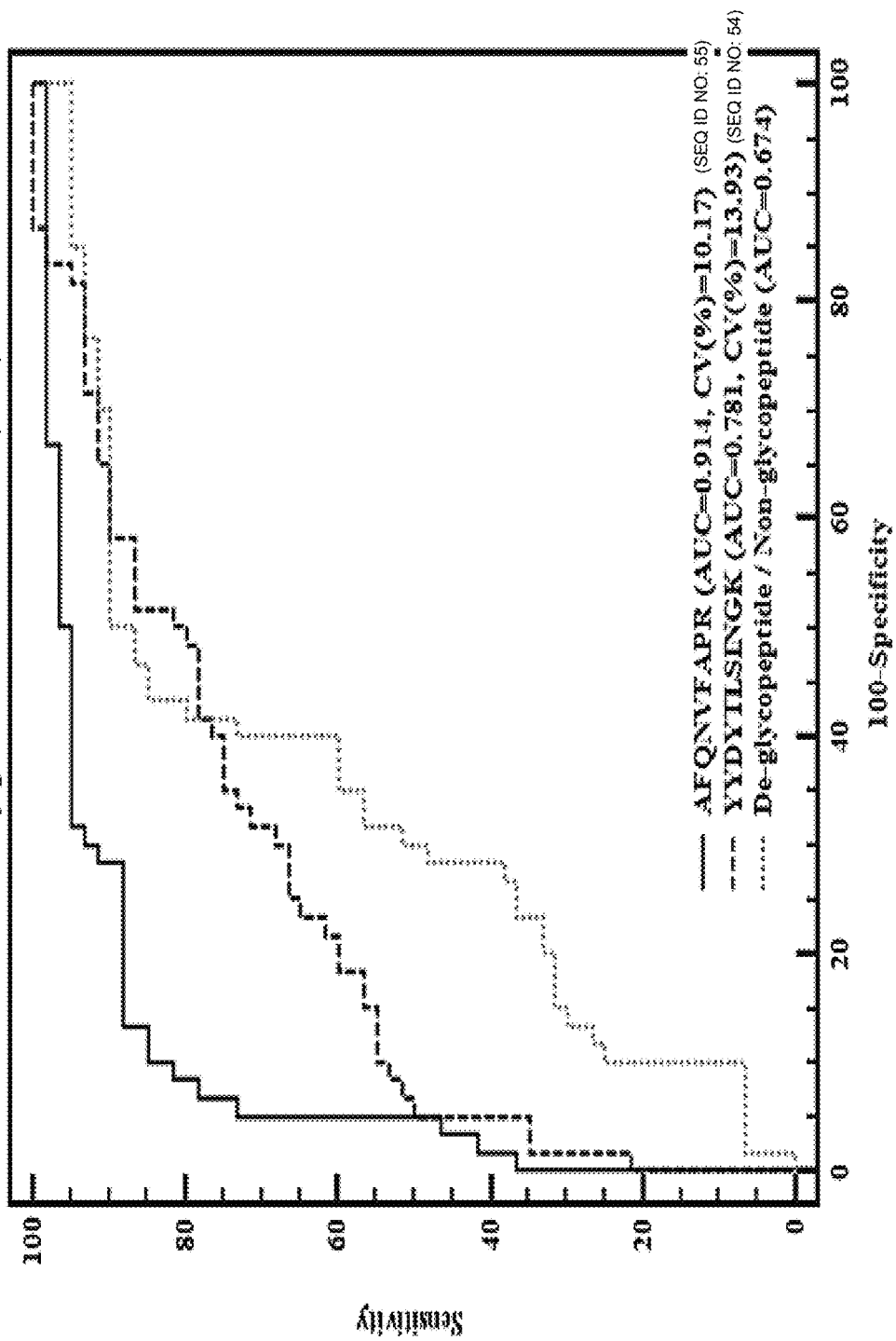

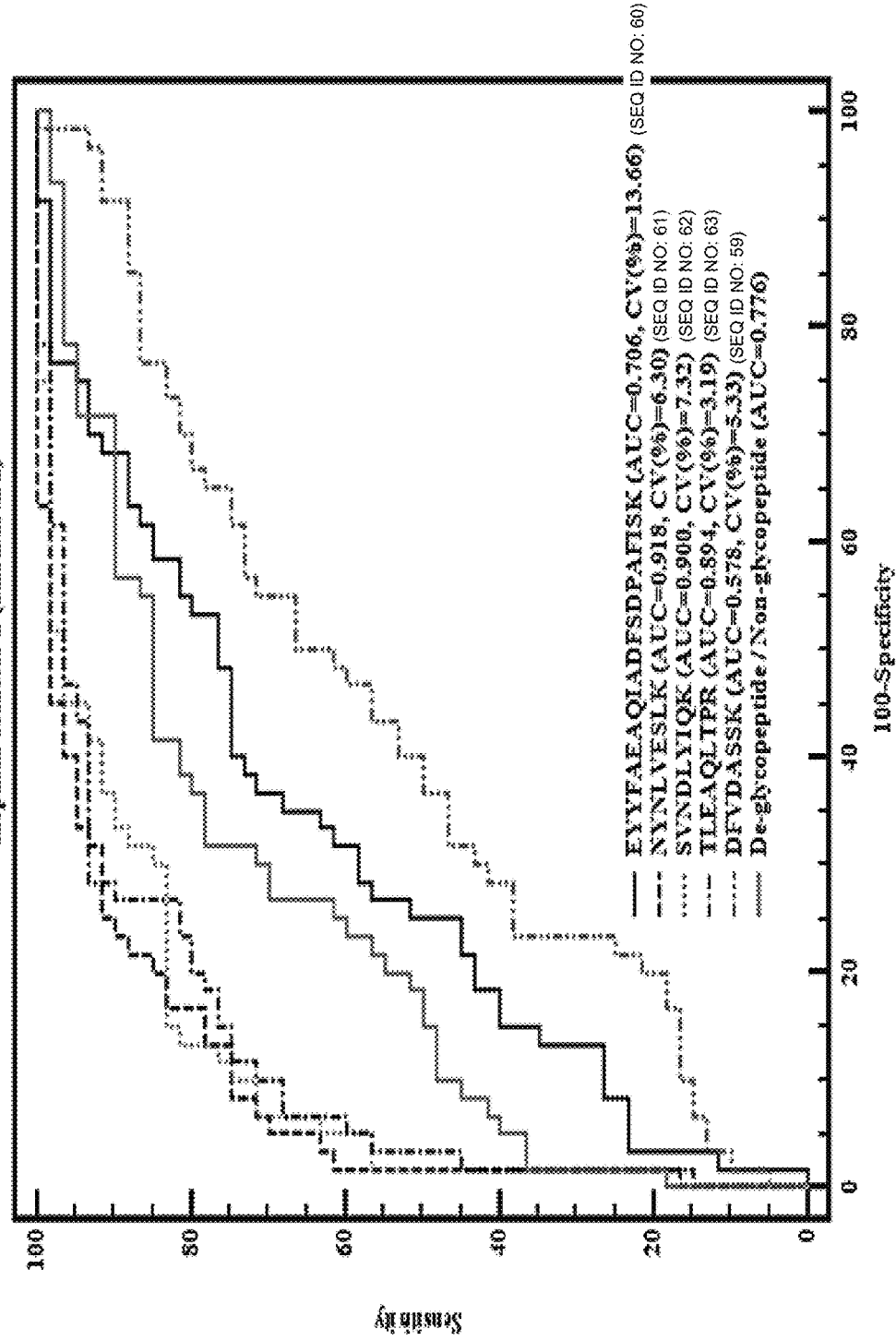

Integrin alpha-3 (ITGA3)

Integrin alpha-M (ITGAM)

Integrin beta-2 (ITGB2)

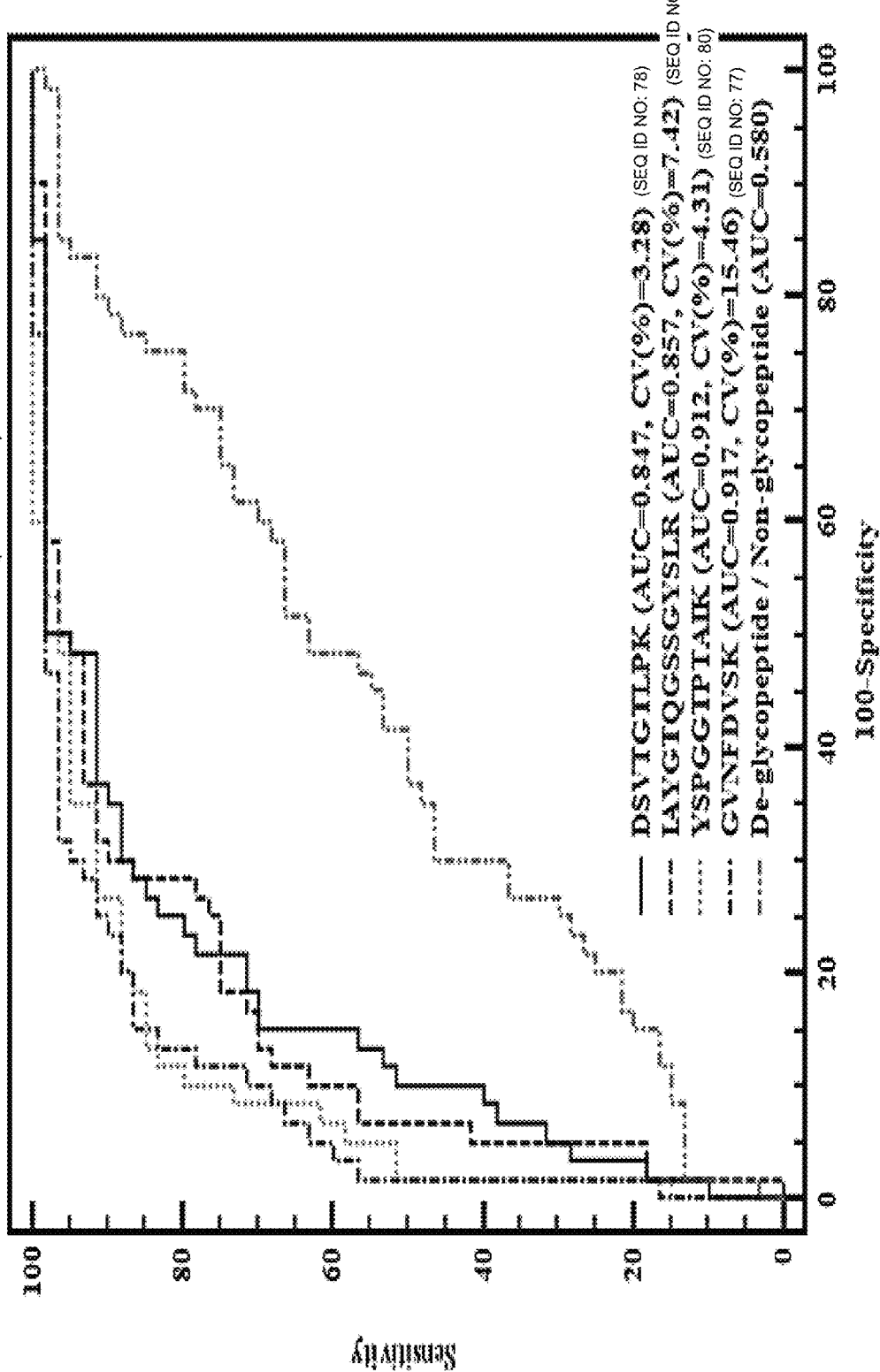

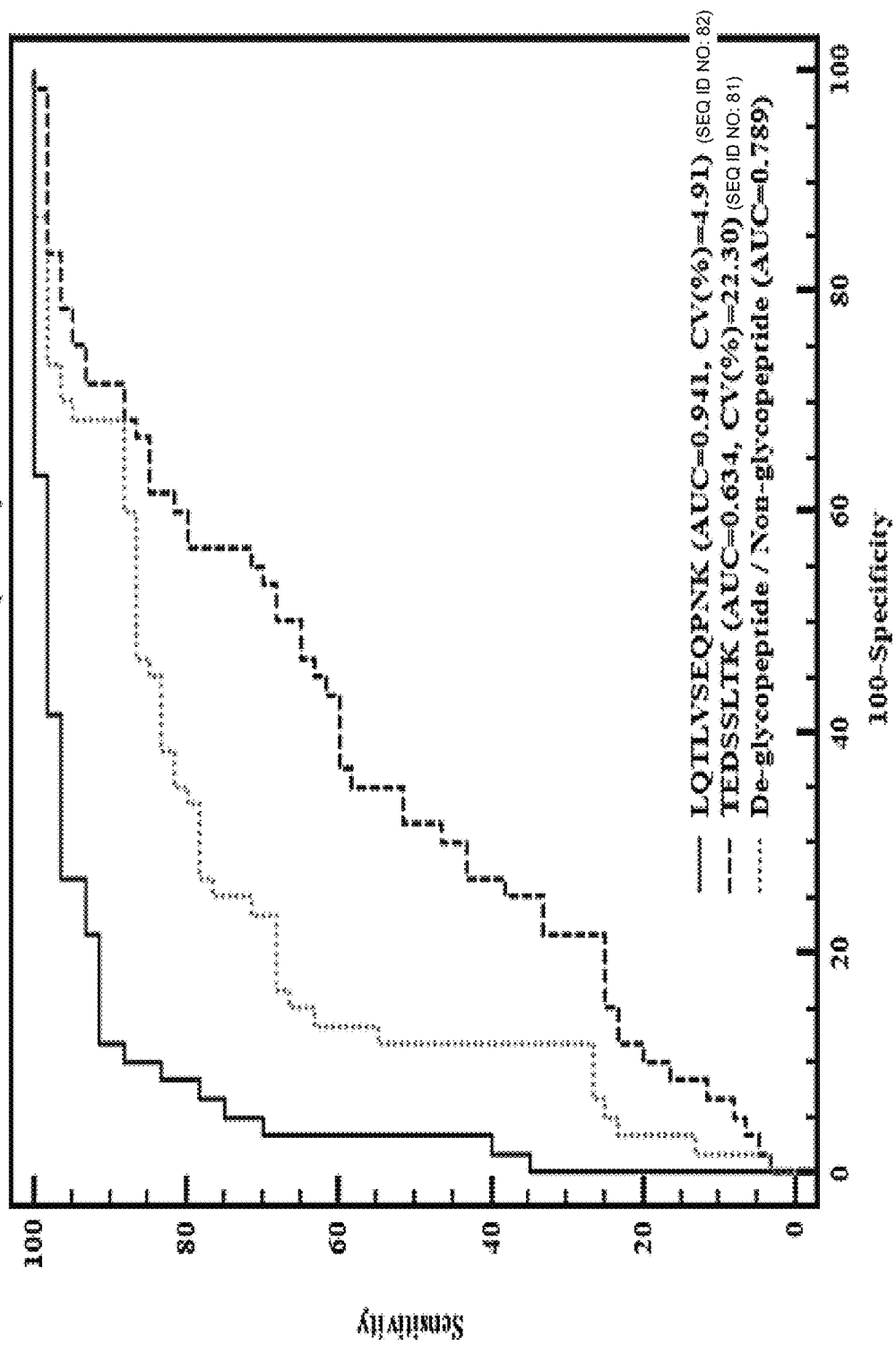
FIG. 18A Kinectin (KTN1)

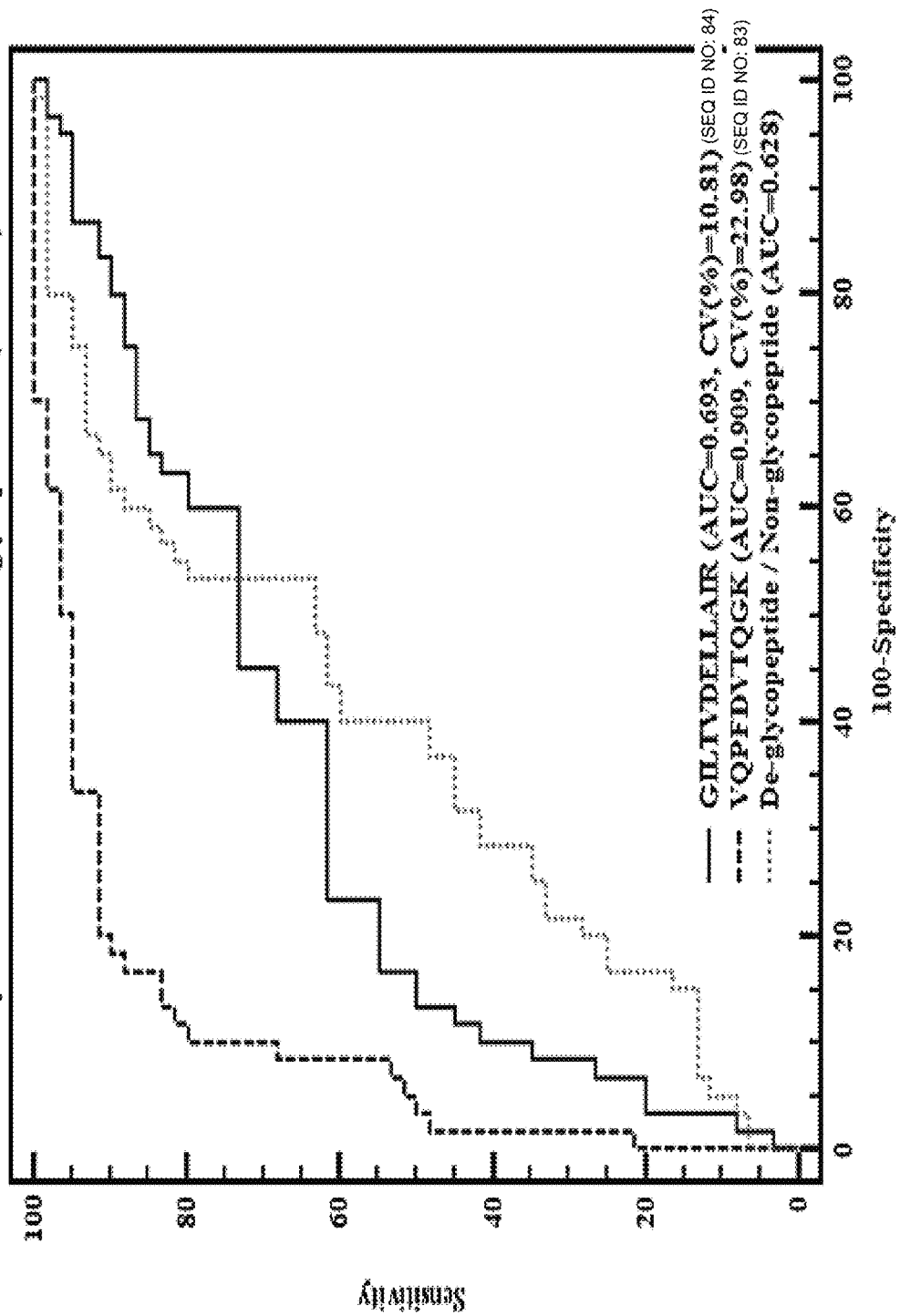

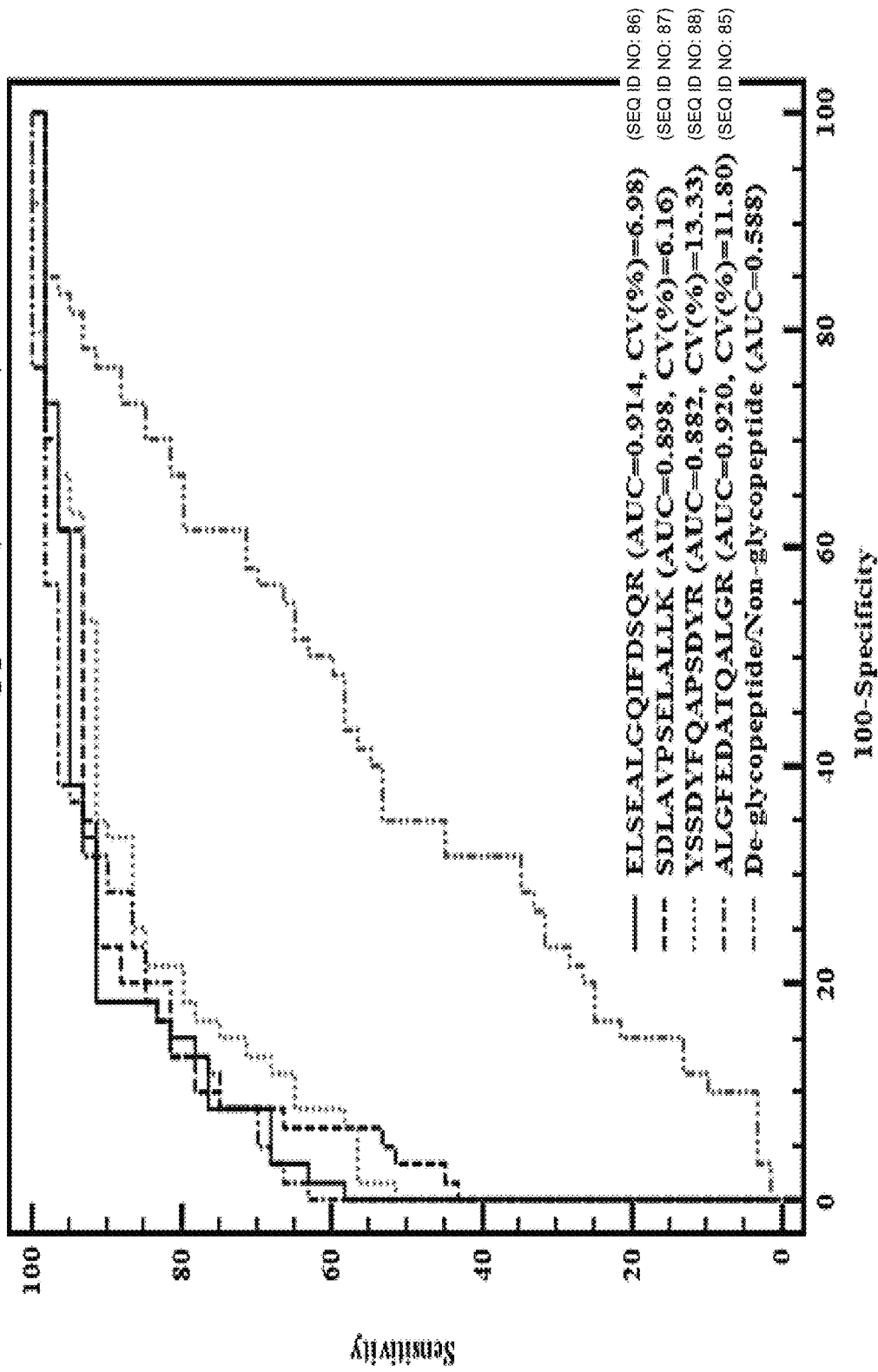

Plexin-A1 (PLXNA1)

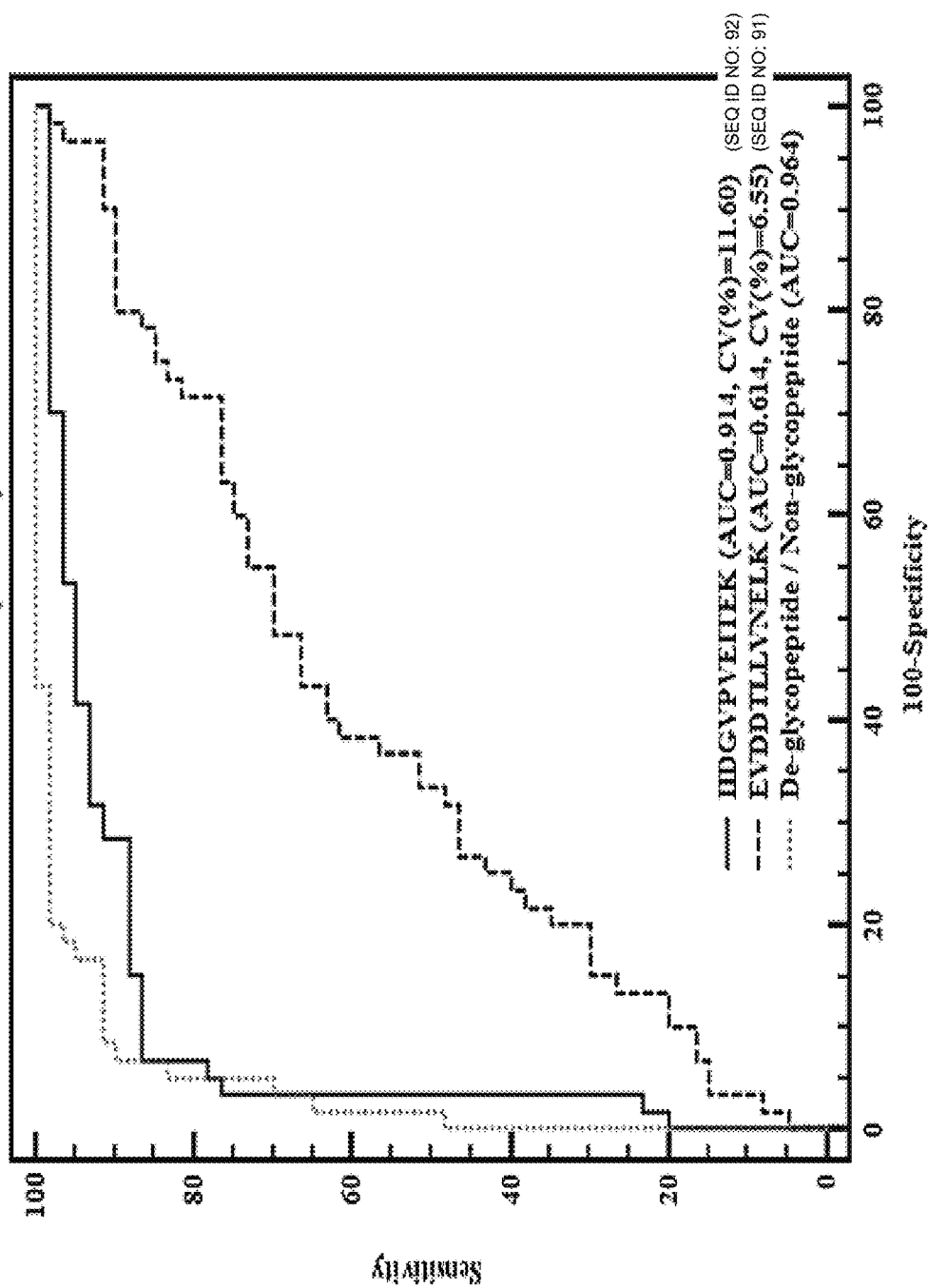

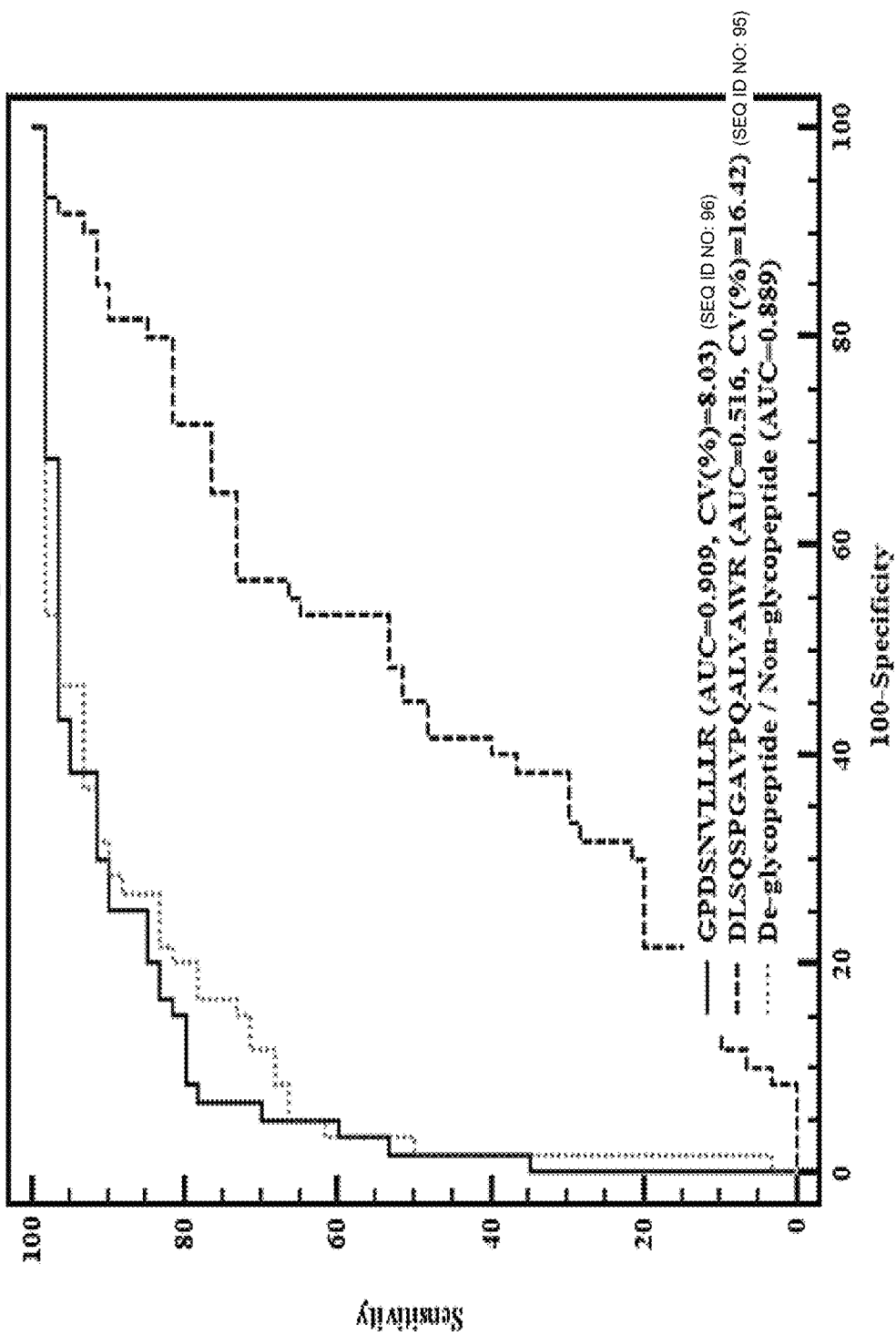

Tenascin (TNC)

Vitronectin (VTN)

SEQUENCE LISTING

<160> NUMBER OF SEQ ID NOS: 109

<210> SEQ ID NO 1
<211> LENGTH: 532
<212> TYPE: PRT
<213> ORGANISM: Saccharomyces cerevisiae
<220> FEATURE:
<221> NAME/KEY: PEPTIDE
<222> LOCATION: (1)..(532)
<223> OTHER INFORMATION: Invertase 1 (INV1)

<400> SEQUENCE: 1

```
Met Leu Leu Gln Ala Phe Leu Phe Leu Leu Ala Gly Phe Ala Ala Lys
  1               5                  10                  15

Ile Ser Ala Ser Met Thr Asn Glu Thr Ser Asp Arg Pro Leu Val His
             20                  25                  30

Phe Thr Pro Asn Lys Gly Trp Met Asn Asp Pro Asn Gly Leu Trp Tyr
         35                  40                  45

Asp Ala Lys Glu Gly Lys Trp His Leu Tyr Phe Gln Tyr Asn Pro Asn
     50                  55                  60

Asp Thr Val Trp Gly Leu Pro Leu Phe Trp Gly His Ala Thr Ser Asp
 65                  70                  75                  80

Asp Leu Thr His Trp Gln Asp Glu Pro Val Ala Ile Ala Pro Lys Arg
                 85                  90                  95

Lys Asp Ser Gly Ala Tyr Ser Gly Ser Met Val Ile Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Lys Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Ser Glu Gln Asp Pro Ser Lys Ser His
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly His His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Ser Asn
305                 310                 315                 320

Pro Trp Arg Ser Ser Met Ser Leu Val Arg Pro Phe Ser Leu Asn Thr
                325                 330                 335

Glu Tyr Gln Ala Asn Pro Glu Thr Glu Leu Ile Asn Leu Lys Ala Glu
            340                 345                 350
```

```
Pro Ile Leu Asn Ile Ser Ser Ala Gly Pro Trp Ser Arg Phe Ala Thr
            355                 360                 365

Asn Thr Thr Leu Thr Lys Ala Asn Ser Tyr Asn Val Asp Leu Ser Asn
370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
            405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
            485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
            515                 520                 525

Arg Glu Val Lys
            530

<210> SEQ ID NO 2
<211> LENGTH: 609
<212> TYPE: PRT
<213> ORGANISM: Homo sapiens
<220> FEATURE:
<221> NAME/KEY: PEPTIDE
<222> LOCATION: (1)..(609)
<223> OTHER INFORMATION: Alpha-fetoprotein (AFP)

<400> SEQUENCE: 2

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
            35                  40                  45

Ile Phe Phe Ala Gln Phe Val Gln Glu Ala Thr Tyr Lys Glu Val Ser
        50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
            85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
            130                 135                 140

Val Thr Ser Cys Glu Ala Tyr Glu Glu Asp Arg Glu Thr Phe Met Asn
145                 150                 155                 160
```

```
Lys Phe Ile Tyr Glu Ile Ala Arg Arg His Pro Phe Leu Tyr Ala Pro
            165                 170                 175
Thr Ile Leu Leu Trp Ala Ala Arg Tyr Asp Lys Ile Ile Pro Ser Cys
            180                 185                 190
Cys Lys Ala Glu Asn Ala Val Glu Cys Phe Gln Thr Lys Ala Ala Thr
            195                 200                 205
Val Thr Lys Glu Leu Arg Glu Ser Ser Leu Leu Asn Gln His Ala Cys
            210                 215                 220
Ala Val Met Lys Asn Phe Gly Thr Arg Thr Phe Gln Ala Ile Thr Val
225                 230                 235                 240
Thr Lys Leu Ser Gln Lys Phe Thr Lys Val Asn Phe Thr Glu Ile Gln
            245                 250                 255
Lys Leu Val Leu Asp Val Ala His Val His Glu His Cys Cys Arg Gly
            260                 265                 270
Asp Val Leu Asp Cys Leu Gln Asp Gly Glu Lys Ile Met Ser Tyr Ile
            275                 280                 285
Cys Ser Gln Gln Asp Thr Leu Ser Asn Lys Ile Thr Glu Cys Cys Lys
            290                 295                 300
Leu Thr Thr Leu Glu Arg Gly Gln Cys Ile Ile His Ala Glu Asn Asp
305                 310                 315                 320
Glu Lys Pro Glu Gly Leu Ser Pro Asn Leu Asn Arg Phe Leu Gly Asp
            325                 330                 335
Arg Asp Phe Asn Gln Phe Ser Ser Gly Glu Lys Asn Ile Phe Leu Ala
            340                 345                 350
Ser Phe Val His Glu Tyr Ser Arg Arg His Pro Gln Leu Ala Val Ser
            355                 360                 365
Val Ile Leu Arg Val Ala Lys Gly Tyr Gln Glu Leu Leu Glu Lys Cys
            370                 375                 380
Phe Gln Thr Glu Asn Pro Leu Glu Cys Gln Asp Lys Gly Glu Glu Glu
385                 390                 395                 400
Leu Gln Lys Tyr Ile Gln Glu Ser Gln Ala Leu Ala Lys Arg Ser Cys
            405                 410                 415
Gly Leu Phe Gln Lys Leu Gly Glu Tyr Tyr Leu Gln Asn Ala Phe Leu
            420                 425                 430
Val Ala Tyr Thr Lys Lys Ala Pro Gln Leu Thr Ser Ser Glu Leu Met
            435                 440                 445
Ala Ile Thr Arg Lys Met Ala Ala Thr Ala Ala Thr Cys Cys Gln Leu
            450                 455                 460
Ser Glu Asp Lys Leu Leu Ala Cys Gly Glu Gly Ala Ala Asp Ile Ile
465                 470                 475                 480
Ile Gly His Leu Cys Ile Arg His Glu Met Thr Pro Val Asn Pro Gly
            485                 490                 495
Val Gly Gln Cys Cys Thr Ser Ser Tyr Ala Asn Arg Arg Pro Cys Phe
            500                 505                 510
Ser Ser Leu Val Val Asp Glu Thr Tyr Val Pro Pro Ala Phe Ser Asp
            515                 520                 525
Asp Lys Phe Ile Phe His Lys Asp Leu Cys Gln Ala Gln Gly Val Ala
            530                 535                 540
Leu Gln Thr Met Lys Gln Glu Phe Leu Ile Asn Leu Val Lys Gln Lys
545                 550                 555                 560
Pro Gln Ile Thr Glu Glu Gln Leu Glu Ala Val Ile Ala Asp Phe Ser
            565                 570                 575
Gly Leu Leu Glu Lys Cys Cys Gln Gly Gln Glu Gln Glu Val Cys Phe
```

```
                    580                 585                 590
Ala Glu Glu Gly Gln Lys Leu Ile Ser Lys Thr Arg Ala Ala Leu Gly
            595                 600                 605
Val

<210> SEQ ID NO 3
<211> LENGTH: 3
<212> TYPE: PRT
<213> ORGANISM: Homo sapiens
<220> FEATURE:
<221> NAME/KEY: PEPTIDE
<222> LOCATION: (1)..(3)
<223> OTHER INFORMATION: X is any amino acid

<400> SEQUENCE: 3

Asn Xaa Ser
  1

<210> SEQ ID NO 4
<211> LENGTH: 3
<212> TYPE: PRT
<213> ORGANISM: Homo sapiens
<220> FEATURE:
<221> NAME/KEY: PEPTIDE
<222> LOCATION: (1)..(3)
<223> OTHER INFORMATION: X is any amino acid

<400> SEQUENCE: 4

Asn Xaa Thr
  1

<210> SEQ ID NO 5
<211> LENGTH: 3
<212> TYPE: PRT
<213> ORGANISM: Homo sapiens
<220> FEATURE:
<221> NAME/KEY: PEPTIDE
<222> LOCATION: (1)..(3)
<223> OTHER INFORMATION: X is any amino acid

<400> SEQUENCE: 5

Asn Xaa Cys
  1

<210> SEQ ID NO 6
<211> LENGTH: 3
<212> TYPE: PRT
<213> ORGANISM: Homo sapiens
<220> FEATURE:
<221> NAME/KEY: PEPTIDE
<222> LOCATION: (1)..(3)
<223> OTHER INFORMATION: X is any amino acid

<400> SEQUENCE: 6

Asp Xaa Ser
  1

<210> SEQ ID NO 7
<211> LENGTH: 3
<212> TYPE: PRT
<213> ORGANISM: Homo sapiens
<220> FEATURE:
<221> NAME/KEY: PEPTIDE
<222> LOCATION: (1)..(3)
<223> OTHER INFORMATION: X is any amino acid

<400> SEQUENCE: 7
```

```
Asp Xaa Thr
  1

<210> SEQ ID NO 8
<211> LENGTH: 3
<212> TYPE: PRT
<213> ORGANISM: Homo sapiens
<220> FEATURE:
<221> NAME/KEY: PEPTIDE
<222> LOCATION: (1)..(3)
<223> OTHER INFORMATION: X is any amino acid

<400> SEQUENCE: 8

Asp Xaa Cys
  1

<210> SEQ ID NO 9
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: AFP De-glycosylated peptide

<400> SEQUENCE: 9

Val Asp Phe Thr Glu Ile Gln Lys
  1               5

<210> SEQ ID NO 10
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: AFP Non-glycosylation peptide

<400> SEQUENCE: 10

Gly Tyr Gln Glu Leu Leu Glu Lys
  1               5

<210> SEQ ID NO 11
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: SERPINF2 De-glycosylated peptide

<400> SEQUENCE: 11

Asn Pro Asp Pro Ser Ala Pro Arg
  1               5

<210> SEQ ID NO 12
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: SERPINF2 Non-glycosylation peptide

<400> SEQUENCE: 12

Leu Gly Asn Gln Glu Pro Gly Gly Gln Thr Ala Leu Lys
  1               5                  10
```

-continued

```
<210> SEQ ID NO 13
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: A2M De-glycosylated peptide

<400> SEQUENCE: 13

Val Ser Asp Gln Thr Leu Ser Leu Phe Phe Thr Val Leu Gln Asp Val
 1               5                  10                  15

Pro Val Arg

<210> SEQ ID NO 14
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: A2M Non-glycosylation peptide

<400> SEQUENCE: 14

Ala Ile Gly Tyr Leu Asn Thr Gly Tyr Gln Arg
 1               5                  10

<210> SEQ ID NO 15
<211> LENGTH: 9
<212> TYPE: PRT
<213> ORGANISM: Homo sapiens
<220> FEATURE:
<221> NAME/KEY: PEPTIDE
<222> LOCATION: (1)
<223> OTHER INFORMATION: A2M Non-glycosylation peptide

<400> SEQUENCE: 15

Phe Glu Val Gln Val Thr Val Pro Lys
 1               5

<210> SEQ ID NO 16
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: A2M Non-glycosylation peptide

<400> SEQUENCE: 16

Ile Ala Gln Trp Gln Ser Phe Gln Leu Glu Gly Gly Leu Lys
 1               5                  10

<210> SEQ ID NO 17
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: A2M Non-glycosylation peptide

<400> SEQUENCE: 17

Asn Glu Asp Ser Leu Val Phe Val Gln Thr Asp Lys
 1               5                  10

<210> SEQ ID NO 18
<211> LENGTH: 18
```

-continued

```
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: A2M Non-glycosylation peptide

<400> SEQUENCE: 18

Val Ser Val Gln Leu Glu Ala Ser Pro Ala Phe Leu Ala Val Pro Val
  1               5                  10                  15

Glu Lys

<210> SEQ ID NO 19
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: APOB De-glycosylated peptide

<400> SEQUENCE: 19

Phe Glu Val Asp Ser Pro Val Tyr Asp Ala Thr Trp Ser Ala Ser Leu
  1               5                  10                  15

Lys

<210> SEQ ID NO 20
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: APOB Non-glycosylation peptide

<400> SEQUENCE: 20

Leu Ser Leu Glu Ser Leu Thr Ser Tyr Phe Ser Ile Glu Ser Ser Thr
  1               5                  10                  15

Lys

<210> SEQ ID NO 21
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: GLB1 De-glycosylated peptide

<400> SEQUENCE: 21

Asn Asn Val Ile Thr Leu Asp Ile Thr Gly Lys
  1               5                  10

<210> SEQ ID NO 22
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: GLB1 Non-glycosylation peptide

<400> SEQUENCE: 22

Val Asn Tyr Gly Ala Tyr Ile Asn Asp Phe Lys
  1               5                  10
```

-continued

```
<210> SEQ ID NO 23
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: BMP1 De-glycosylated peptide

<400> SEQUENCE: 23

Ile Ile Leu Asp Phe Thr Ser Leu Asp Leu Tyr Arg
 1               5                  10

<210> SEQ ID NO 24
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: BMP1 Non-glycosylation peptide

<400> SEQUENCE: 24

Gly Ile Phe Leu Asp Thr Ile Val Pro Lys
 1               5                  10

<210> SEQ ID NO 25
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: SERPINA6 De-glycosylated peptide

<400> SEQUENCE: 25

Ala Gln Leu Leu Gln Gly Leu Gly Phe Asp Leu Thr Glu Arg
 1               5                  10

<210> SEQ ID NO 26
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: SERPINA6 Non-glycosylation peptide

<400> SEQUENCE: 26

Ile Thr Gln Asp Ala Gln Leu Lys
 1               5

<210> SEQ ID NO 27
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: SERPINA6 Non-glycosylation peptide

<400> SEQUENCE: 27

Trp Ser Ala Gly Leu Thr Ser Ser Gln Val Asp Leu Tyr Ile Pro Lys
 1               5                  10                  15

<210> SEQ ID NO 28
<211> LENGTH: 13
<212> TYPE: PRT
<213> ORGANISM: Homo sapiens
```

```
<220> FEATURE:
<221> NAME/KEY: PEPTIDE
<222> LOCATION: (1)..(13)
<223> OTHER INFORMATION: CFH De-glycosylated peptide

<400> SEQUENCE: 28

Ser Pro Asp Val Ile Asp Gly Ser Pro Ile Ser Gln Lys
  1               5                  10

<210> SEQ ID NO 29
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: CFH Non-glycosylation peptide

<400> SEQUENCE: 29

Ser Ser Ile Asp Ile Glu Asn Gly Phe Ile Ser Glu Ser Gln Tyr Thr
  1               5                  10                  15

Tyr Ala Leu Lys
             20

<210> SEQ ID NO 30
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: BCHE De-glycosylated peptide

<400> SEQUENCE: 30

Trp Ser Asp Ile Trp Asp Ala Thr Lys
  1               5

<210> SEQ ID NO 31
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: BCHE Non-glycosylation peptide

<400> SEQUENCE: 31

Ala Ile Leu Gln Ser Gly Ser Phe Asn Ala Pro Trp Ala Val Thr Ser
  1               5                  10                  15

Leu Tyr Glu Ala Arg
             20

<210> SEQ ID NO 32
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: BCHE Non-glycosylation peptide

<400> SEQUENCE: 32

Ile Phe Phe Pro Gly Val Ser Glu Phe Gly Lys
  1               5                  10

<210> SEQ ID NO 33
<211> LENGTH: 10
```

-continued

```
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: BCHE Non-glycosylation peptide

<400> SEQUENCE: 33

Tyr Leu Thr Leu Asn Thr Glu Ser Thr Arg
 1               5                  10

<210> SEQ ID NO 34
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: CLU De-glycosylated peptide

<400> SEQUENCE: 34

Leu Ala Asp Leu Thr Gln Gly Glu Asp Gln Tyr Tyr Leu
 1               5                  10

<210> SEQ ID NO 35
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: CLU Non-glycosylation peptide

<400> SEQUENCE: 35

Ala Ser Ser Ile Ile Asp Glu Leu Phe Gln Asp Arg
 1               5                  10

<210> SEQ ID NO 36
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: CLU Non-glycosylation peptide

<400> SEQUENCE: 36

Glu Ile Gln Asn Ala Val Asn Gly Val Lys
 1               5                  10

<210> SEQ ID NO 37
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: COL12A1 De-glycosylated peptide

<400> SEQUENCE: 37

Asn Val Gln Val Tyr Asp Pro Thr Pro Asn Ser Leu Asp Val Arg
 1               5                  10                  15

<210> SEQ ID NO 38
<211> LENGTH: 10
<212> TYPE: PRT
<213> ORGANISM: Homo sapiens
<220> FEATURE:
<221> NAME/KEY: PEPTIDE
```

-continued

```
<222> LOCATION: (1)..(10)
<223> OTHER INFORMATION: COL12A1 Non-glycosylation peptide

<400> SEQUENCE: 38

Ile Thr Glu Val Thr Ser Glu Gly Phe Arg
 1               5                  10

<210> SEQ ID NO 39
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: COL12A1 Non-glycosylation peptide

<400> SEQUENCE: 39

Val Gln Ile Ser Leu Val Gln Tyr Ser Arg
 1               5                  10

<210> SEQ ID NO 40
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: COL12A1 Non-glycosylation peptide

<400> SEQUENCE: 40

Val Tyr Asp Pro Ser Thr Ser Thr Leu Asn Val Arg
 1               5                  10

<210> SEQ ID NO 41
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: CPN2 De-glycosylated peptide

<400> SEQUENCE: 41

Ala Phe Gly Ser Asn Pro Asp Leu Thr Lys
 1               5                  10

<210> SEQ ID NO 42
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: CPN2 Non-glycosylation peptide

<400> SEQUENCE: 42

Leu Glu Leu Leu Ser Leu Ser Lys
 1               5

<210> SEQ ID NO 43
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: VCAN De-glycosylated peptide

<400> SEQUENCE: 43
```

```
Val Val Ala Glu Asp Ile Thr Gln Thr Ser Arg
1               5                   10

<210> SEQ ID NO 44
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: VCAN Non-glycosylation peptide

<400> SEQUENCE: 44

Leu Leu Ala Ser Asp Ala Gly Leu Tyr Arg
1               5                   10

<210> SEQ ID NO 45
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: VCAN Non-glycosylation peptide

<400> SEQUENCE: 45

Thr Asp Gly Gln Val Ser Gly Glu Ala Ile Lys
1               5                   10

<210> SEQ ID NO 46
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ERBB3 De-glycosylated peptide

<400> SEQUENCE: 46

Asn Leu Asp Val Thr Ser Leu Gly Phe Arg
1               5                   10

<210> SEQ ID NO 47
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ERBB3 Non-glycosylation peptide

<400> SEQUENCE: 47

Leu Ala Glu Val Pro Asp Leu Leu Glu Lys
1               5                   10

<210> SEQ ID NO 48
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: F5 De-glycosylated peptide

<400> SEQUENCE: 48

Thr Trp Asp Gln Ser Ile Ala Leu Arg
1               5
```

<210> SEQ ID NO 49
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: F5 Non-glycosylation peptide

<400> SEQUENCE: 49

Ala Ser Glu Phe Leu Gly Tyr Trp Glu Pro Arg
 1               5                  10

<210> SEQ ID NO 50
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: F11 De-glycosylated peptide

<400> SEQUENCE: 50

Leu Ser Ser Asp Gly Ser Pro Thr Lys
 1               5

<210> SEQ ID NO 51
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: F11 Non-glycosylation peptide

<400> SEQUENCE: 51

Val Val Ser Gly Phe Ser Leu Lys
 1               5

<210> SEQ ID NO 52
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: FSTL1 De-glycosylated peptide

<400> SEQUENCE: 52

Gly Ser Asp Tyr Ser Glu Ile Leu Asp Lys
 1               5                  10

<210> SEQ ID NO 53
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: FSTL1 Non-glycosylation peptide

<400> SEQUENCE: 53

Leu Ser Phe Gln Glu Phe Leu Lys
 1               5

<210> SEQ ID NO 54
<211> LENGTH: 11
<212> TYPE: PRT

```
<213> ORGANISM: Homo sapiens
<220> FEATURE:
<221> NAME/KEY: PEPTIDE
<222> LOCATION: (1)..(11)
<223> OTHER INFORMATION: GNS De-glycosylated peptide

<400> SEQUENCE: 54

Tyr Tyr Asp Tyr Thr Leu Ser Ile Asn Gly Lys
 1               5                  10

<210> SEQ ID NO 55
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: GNS Non-glycosylation peptide

<400> SEQUENCE: 55

Ala Phe Gln Asn Val Phe Ala Pro Arg
 1               5

<210> SEQ ID NO 56
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: GNS Non-glycosylation peptide

<400> SEQUENCE: 56

Ser Leu Ser Ser Ser Ser Ile Gly Ser Asp Ser Thr Tyr Leu Thr Ser
 1               5                  10                  15

Lys

<210> SEQ ID NO 57
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: GPR126 Non-glycosylation peptide

<400> SEQUENCE: 57

Ile Ser Val Val Ile Gln Asn Ile Leu Arg
 1               5                  10

<210> SEQ ID NO 58
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: GPR126 Non-glycosylation peptide

<400> SEQUENCE: 58

Val Ile Leu Pro Gln Thr Ser Asp Ala Tyr Gln Val Ser Val Ala Lys
 1               5                  10                  15

<210> SEQ ID NO 59
<211> LENGTH: 8
<212> TYPE: PRT
<213> ORGANISM: Homo sapiens
<220> FEATURE:
```

```
<221> NAME/KEY: PEPTIDE
<222> LOCATION: (1)..(8)
<223> OTHER INFORMATION: SERPIND1 De-glycosylated peptide

<400> SEQUENCE: 59

Asp Phe Val Asp Ala Ser Ser Lys
 1               5

<210> SEQ ID NO 60
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: SERPIND1 Non-glycosylation peptide

<400> SEQUENCE: 60

Glu Tyr Tyr Phe Ala Glu Ala Gln Ile Ala Asp Phe Ser Asp Pro Ala
 1               5                  10                  15

Phe Ile Ser Lys
            20

<210> SEQ ID NO 61
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SERPIND1 Non-glycosylation peptide

<400> SEQUENCE: 61

Asn Tyr Asn Leu Val Glu Ser Leu Lys
 1               5

<210> SEQ ID NO 62
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SERPIND1 Non-glycosylation peptide

<400> SEQUENCE: 62

Ser Val Asn Asp Leu Tyr Ile Gln Lys
 1               5

<210> SEQ ID NO 63
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SERPIND1 Non-glycosylation peptide

<400> SEQUENCE: 63

Thr Leu Glu Ala Gln Leu Thr Pro Arg
 1               5

<210> SEQ ID NO 64
<211> LENGTH: 11
<212> TYPE: PRT
<213> ORGANISM: Homo sapiens
<220> FEATURE:
<221> NAME/KEY: PEPTIDE
```

```
<222> LOCATION: (1)..(11)
<223> OTHER INFORMATION: HYOU1 De-glycosylated peptide

<400> SEQUENCE: 64

Val Phe Gly Ser Gln Asp Leu Thr Thr Val Lys
1               5                   10

<210> SEQ ID NO 65
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: HYOU1 De-glycosylated peptide

<400> SEQUENCE: 65

Val Ile Asp Glu Thr Trp Ala Trp Lys
1               5

<210> SEQ ID NO 66
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: HYOU1 Non-glycosylation peptide

<400> SEQUENCE: 66

Asp Glu Pro Gly Glu Gln Val Glu Leu Lys
1               5                   10

<210> SEQ ID NO 67
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: ITGA2 De-glycosylated peptide

<400> SEQUENCE: 67

Tyr Phe Phe Asp Val Ser Asp Glu Ala Ala Leu Leu Glu Lys
1               5                   10

<210> SEQ ID NO 68
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: ITGA2 Non-glycosylation peptide

<400> SEQUENCE: 68

Phe Gly Ile Ala Val Leu Gly Tyr Leu Asn Arg
1               5                   10

<210> SEQ ID NO 69
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ITGA3 De-glycosylated peptide

<400> SEQUENCE: 69
```

```
Asp Ile Thr Ile Val Thr Gly Ala Pro Arg
 1               5                  10

<210> SEQ ID NO 70
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ITGA3 Non-glycosylation peptide

<400> SEQUENCE: 70

Thr Val Glu Asp Val Gly Ser Pro Leu Lys
 1               5                  10

<210> SEQ ID NO 71
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: ITGA6 De-glycosylated peptide

<400> SEQUENCE: 71

Leu Trp Asp Ser Thr Phe Leu Glu Glu Tyr Ser Lys
 1               5                  10

<210> SEQ ID NO 72
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: ITGA6 Non-glycosylation peptide

<400> SEQUENCE: 72

Leu Pro Asn Ala Gly Thr Gln Val Arg
 1               5

<210> SEQ ID NO 73
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: ITGAM De-glycosylated peptide

<400> SEQUENCE: 73

Glu Phe Asp Val Thr Val Thr Val Arg
 1               5

<210> SEQ ID NO 74
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ITGAM Non-glycosylation peptide

<400> SEQUENCE: 74

Ile Leu Val Val Ile Thr Asp Gly Glu Lys
 1               5                  10
```

-continued

<210> SEQ ID NO 75
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: ITGB2 De-glycosylated peptide

<400> SEQUENCE: 75

Leu Thr Asp Asn Ser Asn Gln Phe Gln Thr Glu Val Gly Lys
 1               5                  10

<210> SEQ ID NO 76
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ITGB2 Non-glycosylation peptide

<400> SEQUENCE: 76

Ala Leu Asn Glu Ile Thr Glu Ser Gly Arg
 1               5                  10

<210> SEQ ID NO 77
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: KLKB1 De-glycosylated peptide

<400> SEQUENCE: 77

Gly Val Asn Phe Asp Val Ser Lys
 1               5

<210> SEQ ID NO 78
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: KLKB1 Non-glycosylation peptide

<400> SEQUENCE: 78

Asp Ser Val Thr Gly Thr Leu Pro Lys
 1               5

<210> SEQ ID NO 79
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: KLKB1 Non-glycosylation peptide

<400> SEQUENCE: 79

Ile Ala Tyr Gly Thr Gln Gly Ser Ser Gly Tyr Ser Leu Arg
 1               5                  10

<210> SEQ ID NO 80
<211> LENGTH: 11
<212> TYPE: PRT

```
<213> ORGANISM: Homo sapiens
<220> FEATURE:
<221> NAME/KEY: PEPTIDE
<222> LOCATION: (1)..(11)
<223> OTHER INFORMATION: KLKB1 Non-glycosylation peptide

<400> SEQUENCE: 80

Tyr Ser Pro Gly Gly Thr Pro Thr Ala Ile Lys
 1               5                  10

<210> SEQ ID NO 81
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: KTN1 De-glycosylated peptide

<400> SEQUENCE: 81

Thr Glu Asp Ser Ser Leu Thr Lys
 1               5

<210> SEQ ID NO 82
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: KTN1 Non-glycosylation peptide

<400> SEQUENCE: 82

Leu Gln Thr Leu Val Ser Glu Gln Pro Asn Lys
 1               5                  10

<210> SEQ ID NO 83
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: LAMP2 De-glycosylated peptide

<400> SEQUENCE: 83

Val Gln Pro Phe Asp Val Thr Gln Gly Lys
 1               5                  10

<210> SEQ ID NO 84
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: LAMP2 Non-glycosylation peptide

<400> SEQUENCE: 84

Gly Ile Leu Thr Val Asp Glu Leu Leu Ala Ile Arg
 1               5                  10

<210> SEQ ID NO 85
<211> LENGTH: 13
<212> TYPE: PRT
<213> ORGANISM: Homo sapiens
<220> FEATURE:
<221> NAME/KEY: PEPTIDE
<222> LOCATION: (1)..(13)
```

<223> OTHER INFORMATION: LGALS3BP De-glycosylated peptide

<400> SEQUENCE: 85

Ala Leu Gly Phe Glu Asp Ala Thr Gln Ala Leu Gly Arg
1               5                   10

<210> SEQ ID NO 86
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: LGALS3BP Non-glycosylation peptide

<400> SEQUENCE: 86

Glu Leu Ser Glu Ala Leu Gly Gln Ile Phe Asp Ser Gln Arg
1               5                   10

<210> SEQ ID NO 87
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: LGALS3BP Non-glycosylation peptide

<400> SEQUENCE: 87

Ser Asp Leu Ala Val Pro Ser Glu Leu Ala Leu Leu Lys
1               5                   10

<210> SEQ ID NO 88
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: LGALS3BP Non-glycosylation peptide

<400> SEQUENCE: 88

Tyr Ser Ser Asp Tyr Phe Gln Ala Pro Ser Asp Tyr Arg
1               5                   10

<210> SEQ ID NO 89
<211> LENGTH: 11
<212> TYPE: PRT
<213> ORGANISM: Homo sapiens
<220> FEATURE:
<221> NAME/KEY: NP_BIND
<222> LOCATION: (1)..(11)
<223> OTHER INFORMATION: PLXNA1 De-glycosylated peptide

<400> SEQUENCE: 89

Tyr Asp Tyr Thr Glu Asp Pro Thr Ile Leu Arg
1               5                   10

<210> SEQ ID NO 90
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: PLXNA1 Non-glycosylation peptide

<400> SEQUENCE: 90

```
Leu Ser Leu Pro Trp Leu Leu Asn Lys
 1               5
```

<210> SEQ ID NO 91
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: POSTN De-glycosylated peptide

<400> SEQUENCE: 91

```
Glu Val Asp Asp Thr Leu Leu Val Asn Glu Leu Lys
 1               5                  10
```

<210> SEQ ID NO 92
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: POSTN Non-glycosylation peptide

<400> SEQUENCE: 92

```
Ile Ile Asp Gly Val Pro Val Glu Ile Thr Glu Lys
 1               5                  10
```

<210> SEQ ID NO 93
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: PTK7 De-glycosylated peptide

<400> SEQUENCE: 93

```
Ser Ala Asp Ala Ser Phe Asn Ile Lys
 1               5
```

<210> SEQ ID NO 94
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: PTK7 Non-glycosylation peptide

<400> SEQUENCE: 94

```
Ser Ser Leu Gln Pro Ile Thr Thr Leu Gly Lys
 1               5                  10
```

<210> SEQ ID NO 95
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: ROBO4 De-glycosylated peptide

<400> SEQUENCE: 95

```
Asp Leu Ser Gln Ser Pro Gly Ala Val Pro Gln Ala Leu Val Ala Trp
 1               5                  10                  15

Arg
```

<210> SEQ ID NO 96
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: ROBO4 Non-glycosylation peptide

<400> SEQUENCE: 96

Gly Pro Asp Ser Asn Val Leu Leu Leu Arg
1               5                   10

<210> SEQ ID NO 97
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TNC De-glycosylated peptide

<400> SEQUENCE: 97

Leu Leu Glu Thr Val Glu Tyr Asp Ile Ser Gly Ala Glu Arg
1               5                   10

<210> SEQ ID NO 98
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TNC Non-glycosylation peptide

<400> SEQUENCE: 98

Ala Pro Thr Ala Gln Val Glu Ser Phe Arg
1               5                   10

<210> SEQ ID NO 99
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: VTN De-glycosylated peptide

<400> SEQUENCE: 99

Asp Gly Ser Leu Phe Ala Phe Arg
1               5

<210> SEQ ID NO 100
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: VTN Non-glycosylation peptide

<400> SEQUENCE: 100

Asp Val Trp Gly Ile Glu Gly Pro Ile Asp Ala Ala Phe Thr Arg
1               5                   10                  15

<210> SEQ ID NO 101
<211> LENGTH: 12

```
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: VTN Non-glycosylation peptide

<400> SEQUENCE: 101

Phe Glu Asp Gly Val Leu Asp Pro Asp Tyr Pro Arg
 1               5                  10

<210> SEQ ID NO 102
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: CLU De-glycosylated peptide

<400> SEQUENCE: 102

Leu Ala Asp Leu Thr Gln Gly Glu Asp Gln Tyr Tyr Leu Arg
 1               5                  10

<210> SEQ ID NO 103
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: ITGB2 Non-glycosylation peptide

<400> SEQUENCE: 103

Tyr Leu Ile Tyr Val Asp Glu Ser Arg
 1               5

<210> SEQ ID NO 104
<211> LENGTH: 12
<212> TYPE: PRT
<213> ORGANISM: Homo sapiens

<400> SEQUENCE: 104

Asn Pro Val Leu Ala Ala Asn Ser Thr Gln Phe Arg
 1               5                  10

<210> SEQ ID NO 105
<211> LENGTH: 12
<212> TYPE: PRT
<213> ORGANISM: Homo sapiens

<400> SEQUENCE: 105

Asn Pro Val Leu Ala Ala Asp Ser Thr Gln Phe Arg
 1               5                  10

<210> SEQ ID NO 106
<211> LENGTH: 9
<212> TYPE: PRT
<213> ORGANISM: Homo sapiens

<400> SEQUENCE: 106

Phe Ala Thr Asn Thr Thr Leu Thr Lys
 1               5

<210> SEQ ID NO 107
<211> LENGTH: 9
<212> TYPE: PRT
```

```
<213> ORGANISM: Homo sapiens

<400> SEQUENCE: 107

Phe Ala Thr Asp Thr Thr Leu Thr Lys
  1               5

<210> SEQ ID NO 108
<211> LENGTH: 10
<212> TYPE: PRT
<213> ORGANISM: Homo sapiens

<400> SEQUENCE: 108

Ile Glu Ile Tyr Ser Ser Asp Asp Leu Lys
  1               5                  10

<210> SEQ ID NO 109
<211> LENGTH: 6
<212> TYPE: PRT
<213> ORGANISM: Homo sapiens

<400> SEQUENCE: 109

Val Val Asp Phe Gly Lys
  1               5
```

METHOD FOR DIAGNOSING CANCER THROUGH DETECTION OF DEGLYCOSYLATION OF GLYCOPROTEIN

CROSS-REFERENCE TO RELATED APPLICATIONS

The present application is a national stage application of International Patent Application No. PCT/KR2014/006479, filed Jul. 17, 2014, and claims the benefit of Korean Patent Application No. 2013-0088006, filed Jul. 25, 2013 in the Korean Intellectual Property Office, the disclosure of which are incorporated herein.

STATEMENT OF SEQUENCE LISTING

The Sequence Listing submitted in text format (.txt) filed on Jul. 17, 2017, named "SequenceListing.txt", created on Jul. 17, 2017 (35.9 KB), is incorporated herein by reference.

BACKGROUND OF THE INVENTION

Field of the Invention

The present disclosure generally relates to biomarkers and cancer diagnosis using the same, particularly diagnosis or detection of liver cancer.

Description of the Related Art

Biomarkers are widely used to diagnosis various diseases including cancer in which the early detection or diagnosis is crucial for the successful treatment or the accurate diagnosis is difficult with conventional methods. Nucleic acid molecules or proteins are two commonly used types of biomarkers with which the expression levels or any changes in the amount are used as parameters for diagnosis. Recently post-translational modifications of proteins have been developed as biomarkers and one of them is to detect the glycosylation of proteins.

Thus methods have been developed to detect or analyze the changes or differences in the glycosylation levels of proteins. For example, glycoproteins are hydrolyzed to release glycans, which are then collected to profile the glycosylation status (Cooke C. L. et al., Anal. Chem., 2007, 79:8090-8097). Although such methods can be used to differentiate a healthy person from a patient, they have limitations in that various information such as specific information on the glycosylated proteins, positons of the glycosylation and isoforms are required for an accurate diagnosis.

Korean Patent Publication No. 2012-0125157 relates to biomarkers and methods to diagnosis cancer using the information on the aberrant glycosylation and discloses steps of isolating proteins abnormally glycosylated during the development or progression of cancers using lectins, and selecting and quantifying marker peptides generated from the hydrolysis of the isolated glycosylated proteins.

Korean Patent Publication No. 2010-0120788 relates to methods to diagnose a cancer using the glycosylation of proteins and discloses the use of specific changes in the hydrolysis pattern of particular peptides for the diagnosis of cancer.

However the glycosylation of proteins in patients with cancer or cured of cancer may occur at various amino acids residues such as aspargine, threonine, or serine and the like as in healthy patients. Thus, the specific glycosylation patterns or structure associated with a particular cancer may occur at one of the residues as above and coexist with the glycosylation found in normal cases leading to a microheterogeneity. Therefore the specific glycosylation associated with a particular cancer is present in a minute amount relative to a total amount of proteins, existing as a part of many glycan-isoforms found in any one of the residues. This requires a development of a more sensitive and specific methods for a reliable measurement of the glycosylation changes associated with a particular cancer.

SUMMARY OF THE INVENTION

The present disclosure is to provide a method of diagnosing cancer with a high specificity and sensitivity in a noninvasive way by determining the glycosylated ratio of proteins, biomarkers used therefor and a method of screening biomarkers.

In one aspect, the present disclosure provides a method of detecting marker in vitro to provide information for diagnosing or prognosis of cancer in a subject or a sample in need thereof comprising the steps of: providing a sample from the subject comprising proteins having a N-linked glycosylation motif; de-glycosylating the proteins comprised in the sample; fragmenting the de-glycosylated proteins; determining in the fragmented proteins the amount of the de-glycosylated peptide at the N-linked motif and the amount of the non-glycosylated peptide which does not contain the N-linked motif and the ratio therebetween; and diagnosing the subject or the sample as cancer or susceptible to cancer if the ratio is changed in the subject or in the sample compared to that of a control.

In other aspect, the present discourse provides a method of detecting, diagnosing or prognosis of cancer in a subject or a sample in need thereof comprising the steps of: providing a sample from the subject comprising proteins having a N-linked glycosylation motif; de-glycosylating the proteins comprised in the sample; fragmenting the de-glycosylated proteins; determining in the fragmented proteins the amount of the de-glycosylated peptide at the N-linked motif and the amount of the non-glycosylated peptide which does not contain the N-linked motif and the ratio therebetween; and diagnosing the subject or the sample as cancer or susceptible to cancer if the ratio is changed in the subject or in the sample compared to that of a control.

In still other aspect, the present disclosure provides a method of appraise or evaluating a cancer sample, in need thereof comprising the steps of: providing a sample from the subject comprising proteins having a N-linked glycosylation motif; de-glycosylating the proteins comprised in the sample; fragmenting the de-glycosylated proteins; determining in the fragmented proteins the amount of the de-glycosylated peptide at the N-linked motif and the amount of the non-glycosylated peptide which does not contain the N-linked motif and the ratio therebetween; and diagnosing the subject or the sample as cancer or susceptible to cancer if the ratio is changed in the subject or in the sample compared to that of a control. The methods are particularly performed in vitro to diagnose and/or prognosis of cancer and/or monitoring the therapeutic efficacy of the treatments and/or to determine the therapeutic regimes.

In the present methods, the values or ratios of the control samples may be determined or obtained in advance of the present methods are performed or may be determined during the present methods are performed.

In one embodiment of the present disclosure, the N-linked glycosylation motif is represented by the amino acid sequence of AsnXxxSer (SEQ ID NO: 3), AsnXxxThr (SEQ ID NO: 4) (or NxS/T) or AsnXxxCys (SEQ ID NO: 5), which are detected as AspXxxSer (SEQ ID NO: 6), AspXxxThr (SEQ ID NO: 7) and AspXxxCys (SEQ ID NO: 8), respectively when deglycosylated.

The de-glycosylation step may be performed using various methods known in the art including an enzyme. For example, the deglycosylation may be performed using PNGase-F, but is not limited thereto. The fragmentation of the present methods may be performed using various methods known in the art including for example a trypsin, a lysine-C, an arginine-C or an aspartic acid N without being limited thereto.

The present methods may be applied to determine or detect or diagnose or monitoring various cancers such as a blood cancer, a liver cancer, a stomach cancer, a colon cancer, a lung cancer, a uterine cancer, a breast cancer, a prostate cancer, a thyroid cancer and a pancreatic cancer without being limited thereto.

The samples comprising NxS/T motif which may be employed for the present methods includes at least one of a cell, a whole blood, a serum, a plasma, a saliva, a urine, a follicular fluid, a breast milk and a pancreatin without being limited thereto.

In the present methods, for the quantification of the peptides, a Mass spectrometry such as LC-MS (Liquid chromatography spectrometry) may be employed without being limited thereto. And the data from LC-MS may be obtained using Selected Ion Monitoring (SIM) or Multiple reaction monitoring (MRM). Further the determination of the amount using the MRM may be performed by monitoring a m/z value and optimized collision energy as described in the present Examples.

In the present methods, the protein having an N-linked motif may be a protein known in the art in relation to a particular disease. In one embodiment, AFP (alpha feto protein) is used and in which case the de-glycosylated peptide may be VDFTEIQK (SEQ ID NO: 9), and the non-glycosylated peptide may be GYQELLEK (SEQ ID NO: 10). The exact sequence to be detected may be various as long as they comprise NxS/T motif.

In other embodiment, the test protein sample having NxS/T motif to be analyzed is from liver cancer patient, and is blood, and may include ones listed in Table 1 disclosed herein. The de-glycosylated and non-glycosylated peptides corresponding to each protein of Table 1 may include ones listed in Table 1. However, the specific proteins and the corresponding peptides may be various for example depending on the particular methods of quantification employed and/or conditions thereof.

In other aspect, the present disclosure also provides a kit for diagnosis or prognosis of a cancer used for any one of the methods of the present disclosure, the kit comprising a first enzyme de-glycosylating a protein having a AsnXxxSer (SEQ ID NO: 3)/Thr motif, a second enzyme fragmenting the protein, and an agent for quantifying the de-glycosylated and the non-glycosylated peptides.

Advantageous Effects

The present methods can be advantageously used for diagnosis or prognosis or monitoring cancer with a high specificity and sensitivity by measuring the glycosylation ratio of the conventional markers. Also the present methods can be advantageously used to screen markers for cancer diagnosis. Particularly, by using MRM LC-MS in which LC-Mass are combined with Triple quadrupole (QQQ), the total analysis time is very short as 10-15 min and thus the present methods can be efficiently employed for diagnosis of multiple samples.

Also, the present methods can be applied to discover additional markers from the glycoproteins having a higher specificity or sensitivity than the conventional markers, which can be used advantageously to diagnose, monitor the cancer or determine the stages of the cancer. Also the biomarkers and the methods of the present disclosure employed in the glycosylation analysis provides a simple and non-invasive way of diagnose or monitoring cancer using blood as sample.

The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2 is an amino acid sequence (SEQ ID NO: 1) of Invertase-1 used as a standard glycosylated protein in one embodiment of the present disclosure.

FIGS. 4a to 4c are graphs showing the results of MRM analysis of the glycosylated peptide 2 (FATNTTLTK) (SEQ ID NO: 106) of the glycosylated standard protein, in which the peak area according to the concentrations are represented.

FIGS. 5a to 5c are graphs showing the results of MRM analysis of the non-glycosylated peptide 1 (IEIYSSDDLK) (SEQ ID NO: 108) of the glycosylated standard protein, in which the peak area according to the concentrations are represented.

FIG. 8 is an amino acid sequence of AFP (Alpha fetoprotein) (SEQ ID NO: 2), in which glycosylated peptide and non-glycosylated peptide are indicated as red and green, respectively.

FIGS. 9a and 9b are results of MRM analysis of glycosylated peptide (VNFTEIQ) (SEQ ID NO: 9) and de-glycosylated peptide (VDFTEIQK) (SEQ ID NO: 9) of AFP, respectively using the pooled normal control sample.

FIGS. 9c and 9d are results of MRM analysis of glycosylated peptide (VNFTEIQ) (SEQ ID NO: 9) and deglycosylated peptide (VDFTEIQK) (SEQ ID NO: 9) of AFP, respectively using the pooled liver cancer patient sample.

FIG. 14 is a result of MRM analysis showing the linearity which was performed to confirm the quantifiable property of the heavy labelled synthetic peptides to AFP target peptide.

FIG. 15 is a result of MRM analysis using clinical samples in which de-glycosylation of the glycosylated peptide and non-glycosylated peptide of AFP were analyzed.

FIGS. 18a to 18i are results showing AUC values of standardized de-glycosylated peptide and standardized non-glycosylated peptide and the ratio thereof of various selected proteins to discover the potential glycosylated markers.

DETAILED DESCRIPTION OF THE EMBODIMENTS

Figure 1:
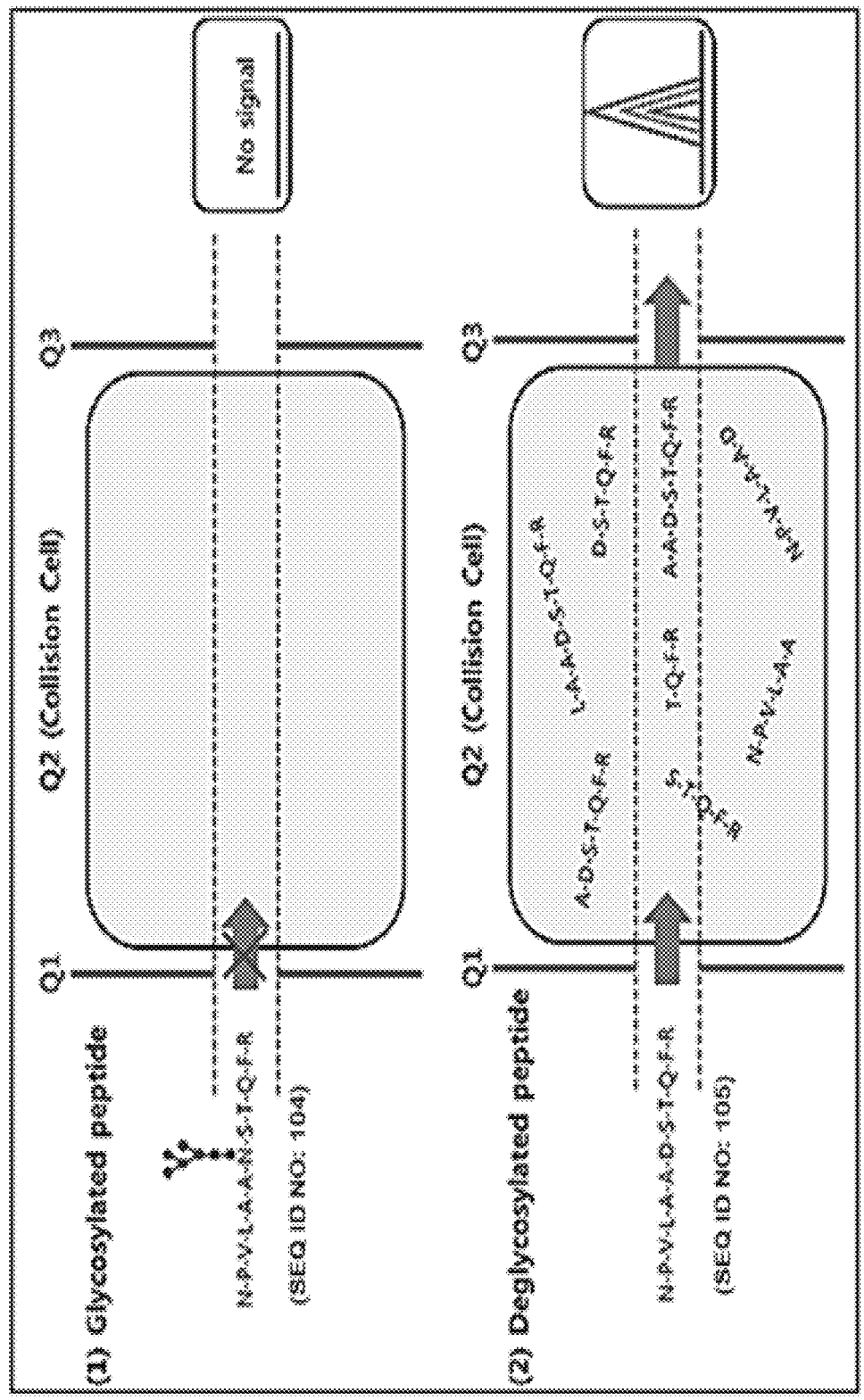
FIG. 1 is a schematic representation of the analysis principal of the glycosylated fragments using LC-Mass in one embodiment of the present disclosure, in which glycosylated and non-glycosylated peptides are indicated as green and glycosylated amino acids are indicated as red.

The present disclosure is based on the findings that the level of glycosylation of proteins in comparison to non-glycosylated proteins occurring during the post translational modification can be used effectively to diagnose cancers.

In one aspect of the present disclosure, there is provided a method of diagnosing or prognosis of cancer, or monitoring the progress of the therapy or the state the cancer in a subject or a sample in need thereof comprising steps of: providing a biological sample from the subject, the sample comprising proteins having a N-linked glycosylation motif; de-glycosylating the proteins comprised in the sample; fragmenting the de-glycosylated proteins; determining in the fragmented proteins the amount of the de-glycosylated peptides at the N-linked motif and the amount of the non-glycosylated peptides at a non N-linked motif and the ratio of the glycosylated peptide to the non-glycosylated peptide; and diagnosing the subject or the sample as cancer or susceptible to cancer if the ratio is changed in the subject compared to that of a normal control.

In other aspect of the present disclosure, there is provided a method of assess or diagnose a sample from a cancer patient or a patient suspected of cancer, comprising steps of: providing a sample from a cancer patient or a patient suspected of cancer comprising proteins having a N-linked glycosylation motif; de-glycosylating the proteins comprised in the sample; fragmenting the de-glycosylated proteins; determining in the fragmented proteins the amount of the de-glycosylated peptides at the N-linked motif and the amount of the non-glycosylated peptides at a non N-linked motif and the ratio of the glycosylated peptide to the non-glycosylated peptide; and diagnosing the sample as cancer or susceptible to cancer if the ratio is changed in the sample compared to that of a normal control. The present methods may be performed in vitro and/or in vivo. In one embodiment, the method is performed in vitro to diagnose and/or prognosis of cancer, and/or monitoring the progress or the status of a subject to provide the information on the efficacy of treatment, and/or selecting optimal therapy regimes.

In the present disclosure, the value determined in a normal control which is used to compare to that of a cancer sample may be a value determined during or before the method is performed.

Proteins undergo post translational modification (PTM) after translation to become functional. Among PTM, glycosylation plays an important role in various cellular process or properties of the proteins such as half-lives, cell-cell interaction and antigenic properties of the proteins. Glycosylation is the enzyme catalyzed process in contrast to non-enzymatic glycation process, and during the process sugars are added to proteins to form glycan chains.

Included in the types of Glycosylation are N-linked glycosylation, O-linked glycosylation, C-mannosylation and GPI (glycophosphatidyl-inositol) anchor attachment. Encompassed in the present disclosure is N-linked glycosylation.

By N-linked glycosylation, glycan is attached to Asparagine residue at the same time with a translation affecting protein folding. N-linked glycosylation occurs at a particular peptide motif including Asn-Xxx-Ser (SEQ ID NO: 3)/Thr (N-X-S/T) or Asn-Xxx-Cys (SEQ ID NO: 5) (N-X-C), in which Xxx refers to any amino acids except proline. The proteins comprised in the present biological sample comprise N-linked glycosylation motifs at all or part of which the proteins are glycosylated. As diseases such as cancer develops or progresses, the amount of proteins expressed and/or the level of glycosylation and a particular type of sugar for example fucose is attached.

In the present disclosure, the biological samples from a patient or a normal control employed in the present methods comprise N-linked glycosylation motif. The samples to be tested are from patients who have a cancer or who are suspected of having cancer or who are in need of a cancer diagnosis or who are undergoing cancer therapy or who are cured of cancer. As a control, biological samples from a normal subject or a subject cured of cancer may be used. In the present disclosure, the subject includes mammals, particularly humans.

In accordance of the present disclosure, not only biological samples from appropriate patients but also proteins extracted from the sample are included. In one embodiment, the samples embodied in the present disclosure are a biological sample obtained from an organism including proteins from which information related to disease such as cancer development or progress or status can be determined or detected. Such samples include biological tissues, cell lines obtained by culturing biological tissues or media from the culture cells, cells, whole blood, serum, plasma, saliva, urine, cerebro-spinal fluid, liquor folliculi, milk and pancreatin, but are not limited thereto. Particularly glycoproteins related to cancer development or progress of the disease are released from the cells into the blood or extracellular fluids and thus bloods from the patient/subject to be tested or culture media in which cancer cells have been cultured can be advantageously used for detecting glycoproteins. In case of blood, the concentrations of proteins comprised therein varies widely among them. Thus, the samples may be pretreated to remove abundant proteins using a column such as MARS (Multiple Affinity Removal System) and the like. However the pretreatment may be omitted if the sensitivity and reproducibility of the target protein detection is not affected.

Particularly, many kinds of monosaccharides present on the surface of the cell membrane and they move inside the cell membrane by a signal transduction and are enzymatically transferred to proteins in the membrane by N-acetylglucosaminyltransferase to produce glycosylated proteins. The glycoproteins then perform their cellular function. Many glycoproteins present on the cell surface undergo abnormal glycosylation by particular signals generated from such as oncogenes. It has been known that abnormal function of glycosyltransferases and glycolytic enzymes due in response to the signal by oncogenes are involved in the cancer development (Kim, Y. J., et al., Glycoconj. J., 1997, 14, 569-576., Hakomori, S., Adv. Cancer Res., 1989, 52, 257-331., Hakomori, S., Cancer Res., 1996, 56, 5309-5318).

In the present methods, the ratio of glycosylated proteins to non-glycosylated proteins at a particular motif is determined and that is used to diagnose and/or prognosis and/or monitor various cancers in which glycosylation is associated with the development or progression of cancer. For example, such cancers include blood cancer, liver cancer, colon cancer, lung cancer, uterine cancer, breast cancer, prostate cancer, thymus cancer and pancreatic cancer but are not limited thereto. The term diagnosis as used herein refers to determining susceptibility of a subject to a disease or disorder, determining whether a subject has a specific disease or disorder, determining the prognosis (for example, identification of transitional cancer status, stages or progression of a cancer or determining the response to cancer treatments) of a subject who has a particular disease or disorder, or therametrics (for example, monitoring the status of a subject to provide the information on the efficacy of treatment).

In accordance with the present methods, the level of de-glycosylated motif at the glycosylation motif and the level of non-glycosylation motif and its ratio are determined, which is then compared to the values obtained from a normal control. In comparison to the control, when the ratio is changed, i.e., decreased or increased, in the subject or in the sample, the ratios are used to diagnose, prognosis or detect cancer, or monitor the stages or progression of cancer. The levels may be determined as described hererinafter. When liquid chromatographic methods are used, the area of the peak corresponding to de-glycosylated fragments and the area of the peak corresponding to non-glycosylation fragments are determined, which are then used to calculate the ratios after normalization of each of the peak area above with that of the internal standard peptide, i.e., to calculate the normalized peak area of the de-glycosylated fragment/the normalized peak area of the non-glycosylated fragment.

Therefore, to de-glycosylate the glycosylation motif and fragment them, various de-glycosylation enzymes known in the art may be employed for the present methods. In one embodiment, PNGase-F (Peptide N Glycosidase F) is used. In the present methods, the proteins in the sample are fragmented into polypeptides of 6-24 amino acids in length. For this, various hydrolytic enzymes may be employed, which include for example trypsin that digest amide bond between lysine and arginine. Also lysine-C that hydrolyzes at a lysine residue, arginine-C that hydrolyzes at an arginine residue, an aspartic acid N that hydrolyzes at an aspartic acid may also be used as desired. In one embodiment, a trypsin is used.

The non-glycosylation motif employed in the present methods is an amino acid sequence which is not glycosylated and found in the same protein as the glycosylation motif is found. The non-glycosylation motif does not contain NxS/T motif, cysteine as well as methionine. The length of the non-glycosylation motif may vary depending on the detection methods employed. For example, when the mass spectrometry is used, the peptide length of about 5 to about 24 amino acids may be selected and used in consideration of the detection range which is about 15-1400 m/z, average molecular weight and charge of an amino acid, and a minimum length conferring specificity. But the length is not limited thereto.

In one embodiment, the glycosylation and non-glycosylation motifs are selected from the proteins which may be used as a diagnostic marker of liver cancer such as AFP, SERPINF2, A2M, APOB, GLB1, BMP1, SERPINA6, CFH, BCHE, CLU, COL12A1, CPN2, VCAN, ERBB3, F5, F11, AFP, FSTL1, GNS, GPR126, SERPIND1, HYOU1, ITGA2, ITGA3, ITGA6, ITGAM, ITGB2, KLKB1, KTN1, LAMP2, LGALS3BP, PLXNA1, POSTN, PTK7, ROBO4, TNC, or VTN. The de-glycosylated peptide which is generated by the de-glycosylation of glycosylation peptide, and the non-glycosylation motifs are as disclosed in Table 1. More than one peptide may be selected.

TABLE 1

| Protein Marker | De-glycosylated peptide | Non-glycosylation peptide |
|---|---|---|
| AFP | VDFTEIQK (SEQ ID NO: 9) | GYQELLEK (SEQ ID NO: 10) |
| SERPINF2 | NPDPSAPR (SEQ ID NO: 11) | LGNQEPGGQTALK (SEQ ID NO: 12) |
| A2M | VSDQTLSLFFTVLQDVPVR (SEQ ID NO: 13) | AIGYLNTGYQR (SEQ ID NO: 14)<br>FEVQVTVPK (SEQ ID NO: 15)<br>IAQWQSFQLEGGLK (SEQ ID NO: 16)<br>NEDSLVFVQTDK (SEQ ID NO: 17)<br>VSVQLEASPAFLAVPVEK (SEQ ID NO: 18) |
| APOB | FEVDSPVYDATWSASLK (SEQ ID NO: 19) | LSLESLTSYFSIESSTK (SEQ ID NO: 20) |
| GLB1 | NNVITLDITGK (SEQ ID NO: 21) | VNYGAYINDFK (SEQ ID NO: 22) |
| BMP1 | IILDFTSLDLYR (SEQ ID NO: 23) | GIFLDTIVPK (SEQ ID NO: 24) |

TABLE 1-continued

| Protein Marker | De-glycosylated peptide | Non-glycosylation peptide |
|---|---|---|
| SERPINA6 | AQLLQGLGFDLTER (SEQ ID NO: 25) | ITQDAQLK (SEQ ID NO: 26)<br>WSAGLTSSQVDLYIPK (SEQ ID NO: 27) |
| CFH | SPDVIDGSPISQK (SEQ ID NO: 28) | SSIDIENGFISESQYTYALK (SEQ ID NO: 29) |
| BCHE | WSDIWDATK (SEQ ID NO: 30) | AILQSGSFNAPWAVTSLYEAR (SEQ ID NO: 31)<br>IFFPGVSEFGK (SEQ ID NO: 32)<br>YLTLNTESTR (SEQ ID NO: 33) |
| CLU | LADLTQGEDQYYL (SEQ ID NO: 34) | ASSIIDELFQDR (SEQ ID NO: 35)<br>EIQNAVNGVK (SEQ ID NO: 36) |
| COL12A1 | NVQVYDPTPNSLDVR (SEQ ID NO: 37) | ITEVTSEGFR (SEQ ID NO: 38)<br>VQISLVQYSR (SEQ ID NO: 39)<br>VYDPSTSTLNVR (SEQ ID NO: 40) |
| CPN2 | AFGSNPDLTK (SEQ ID NO: 41) | LELLSLSK (SEQ ID NO: 42) |
| VCAN | VVAEDITQTSR (SEQ ID NO: 43) | LLASDAGLYR (SEQ ID NO: 44)<br>TDGQVSGEAIK (SEQ ID NO: 45) |
| ERBB3 | NLDVTSLGFR (SEQ ID NO: 46) | LAEVPDLLEK (SEQ ID NO: 47) |
| F5 | TWDQSIALR (SEQ ID NO: 48) | ASEFLGYWEPR (SEQ ID NO: 49) |
| F11 | LSSDGSPTK (SEQ ID NO: 50) | VVSGFSLK (SEQ ID NO: 51) |
| FSTL1 | GSDYSEILDK (SEQ ID NO: 52) | LSFQEFLK (SEQ ID NO: 53) |
| GNS | YYDYTLSINGK (SEQ ID NO: 54) | AFQNVFAPR (SEQ ID NO: 55) |
| GPR126 | SLSSSSIGSDSTYLTSK (SEQ ID NO: 56) | ISVVIQNILR (SEQ ID NO: 57)<br>VILPQTSDAYQVSVAK (SEQ ID NO: 58) |
| SERPIND1 | DFVDASSK (SEQ ID NO: 59) | EYYFAEAQIADFSDPAFISK (SEQ ID NO: 60)<br>NYNLVESLK (SEQ ID NO: 61)<br>SVNDLYIQK (SEQ ID NO: 62)<br>TLEAQLTPR (SEQ ID NO: 63) |
| HYOU1 | VFGSQDLTTVK (SEQ ID NO: 64)<br>VIDETWAWK (SEQ ID NO: 65) | DEPGEQVELK (SEQ ID NO: 66) |
| ITGA2 | YFFDVSDEAALLEK (SEQ ID NO: 67) | FGIAVLGYLNR (SEQ ID NO: 68) |
| ITGA3 | DITIVTGAPR (SEQ ID NO: 69) | TVEDVGSPLK (SEQ ID NO: 70) |
| ITGA6 | LWDSTFLEEYSK (SEQ ID NO: 71) | LPNAGTQVR (SEQ ID NO: 72) |
| ITGAM | EFDVTVTVR (SEQ ID NO: 73) | ILVVITDGEK (SEQ ID NO: 74) |
| ITGB2 | LTDNSNQFQTEVGK (SEQ ID NO: 75) | ALNEITESGR (SEQ ID NO: 76) |
| KLKB1 | GVNFDVSK (SEQ ID NO: 77) | DSVTGTLPK (SEQ ID NO: 78)<br>IAYGTQGSSGYSLR (SEQ ID NO: 79)<br>YSPGGTPTAIK (SEQ ID NO: 80) |
| KTN1 | TEDSSLTK (SEQ ID NO: 81) | LQTLVSEQPNK (SEQ ID NO: 82) |
| LAMP2 | VQPFDVTQGK (SEQ ID NO: 83) | GILTVDELLAIR (SEQ ID NO: 84) |
| LGALS3BP | ALGFEDATQALGR (SEQ ID NO: 85) | ELSEALGQIFDSQR (SEQ ID NO: 86)<br>SDLAVPSELALLK (SEQ ID NO: 87)<br>YSSDYFQAPSDYR (SEQ ID NO: 88) |
| PLXNA1 | YDYTEDPTILR (SEQ ID NO: 89) | LSLPWLLNK (SEQ ID NO: 90) |
| POSTN | EVDDTLLVNELK (SEQ ID NO: 91) | IIDGVPVEITEK (SEQ ID NO: 92) |
| PTK7 | SADASFNIK (SEQ ID NO: 93) | SSLQPITTLGK (SEQ ID NO: 94) |
| ROBO4 | DLSQSPGAVPQALVAWR (SEQ ID NO: 95) | GPDSNVLLLR (SEQ ID NO: 96) |
| TNC | LLETVEYDISGAER (SEQ ID NO: 97) | APTAQVESFR (SEQ ID NO: 98) |

TABLE 1-continued

| Protein Marker | De-glycosylated peptide | Non-glycosylation peptide |
| --- | --- | --- |
| VTN | DGSLFAFR (SEQ ID NO: 99) | DVWGIEGPIDAAFTR (SEQ ID NO: 100)<br>FEDGVLDPDYPR (SEQ ID NO: 101) |

For the quantification of de-glycosylated and non-glycosylation peptides and the ratio therebetween (the de-glycosylated/non-glycosylation peptide), it is preferred to employ a sensitive process particularly in normal and cancer samples or sample suspected of cancer. For this, abundant proteins which represent about 90% of plasma proteins such as albumin, 1 gG, 1 gA, Transferrin, Haptoglobin), Fibrinogen are removed. Or the proteins may be purified and concentrated using acetone precipitation or MWCO (molecular weight cut-off) methods to remove salts. In one embodiment of the present disclosure, the de-glycosylated peptide fragment in the N-linked glycosylation motif, NxS/T or NxC, is AsnXxxSer (SEQ ID NO: 3)/Thr or AsnXxxSer (SEQ ID NO: 3)/Cys in which asparagine in the motif is changed to aspartic acid by glycosylation. That is, the peptide fragments which are detected as a result of de-glycosylation in N-linked glycosylation motif are AspXxx-Ser (SEQ ID NO: 6)/Thr or AspXxxSer (SEQ ID NO: 6)/Cys.

In one embodiment of the present disclosure, a mass spectrometry is used for detecting the present markers, wherein the proteins are extracted from the appropriate samples and analyzed using the method such as described in the Examples of the present disclosure, or the literatures Kim, et al. 2010 J Proteome Res. 9: 689-99; Anderson, L et al. 2006. Mol Cell Proteomics 5: 573-88 may also be referred. In one embodiment Multiple Reaction Monitoring (MRM) technology utilizing Triple Quadrupole LC-MS/MS and QTRAP and the like may be used. MRM is a method for exactly quantifying multiple markers present in biological samples in minute amount. In MRM, by a first mass filter (Q1), parent or precursor ions are selected from the ion fragments generated in ionization source and transferred to a collision cell. And then the precursor ions arrived at the collision cell collide with internal collision gas, and are fragmented into products or daughter ions and transferred to a second mass filter (Q2), from which only the specific ions are delivered to a detector. In this way only the information of the desired target can be obtained with high selectivity and sensitivity. The literature Gillette et al., 2013, Nature Methods 10:28-34 and the like may be referred.

In other embodiment, liquid chromatography mass spectrometry is used. For example, Selected Ion Monitoring (SIM) or MRM is used, in which the peptides are not labelled and the data generated are analyzed based on the accurate MW of the peptides or proteins and the retention time of the peptides separated from the chromatography. In one embodiment, MRM is employed. In MRM analysis, peptide/transitions are monitored for analysis.

In MRM, a relative analysis without the use of labelling, or an absolute analysis using stable isotope labeled peptide standard which is injected before the analysis are used. Also for a more efficient quantification using multiple reaction monitoring, the database and programs such as TIQAM (targeted identification for quantitative analysis by MRM) may also be employed to select a unique peptide only detected in the candidate proteins and to generate and confirm MRM transition of the peptide (Anderson L, et al., Mol. Cell Proteomics. 2006, 5: 573-588).

In one embodiment, blood is obtained from a patient having a disease or suspected of a disease, which is then analyzed by LC/MS (Liquid Chromatography/Mass Spectrometer) to detect the glycosylation and de-glycosylation levels and the ratio therebetween in the appropriate proteins. The levels and/or ratios determined in the test samples are then compared to that of a control to diagnose and/or for prognosis.

As a way of example, cutoff value of a particular peptide at issue in the normal sample (upper or lower limit depending on increasing or decreasing, respectively) is determined. Then the ratio of de-glycosylation/non-glycosylation level determined in the samples from a patient having a disease or suspected of a disease is changed, i.e., decreased or increased, compared to the cutoff value, the patient is diagnosed to have a disease. The extent of increase or decrease compared to the control and the diagnosis based thereon may vary depending on the factors such as types of disease, disease properties, and types of the sample, sex and age of the patients, analysis methods and/or device. One of ordinary skill in the art would be able to select appropriate ranges or values for the diagnosis. Also the measured values may be monitored for its recovery to a normal level to follow up a therapeutic efficacy of the treatment. The present methods may be used alone or in combination with a conventional method.

In the present methods, de-glycosylation and non-glycosylation of multiple proteins in one sample may be detected simultaneously or individually. For example a maximum of about 1,000 peptides including de-glycosylated and non-glycosylated peptides may be detected at one time, this represents the detection of about 500 glycosylated proteins. When the multiple proteins are analyzed for a particular disease, the data from the analysis are combined and used to create a panel specialized for a particular disease, which increases the accuracy (specificity and sensitivity) of the diagnosis of a disease such as cancer.

In other aspect, the present methods may be used for screening the cancer marker by detecting the various glycoproteins glycosylated and/or de-glycosylated in a particular cancer, which may be more sensitive and specific compared to a conventional marker.

The term biomarker for diagnosing or diagnosis marker as used herein refers to an agent that may discriminate a cancer tissues or cells from normal cells or a treated cancer tissues or cells, and comprises an organic and biological molecule and the like, such as proteins or nucleic acid molecules, lipid, glycolipid, and glycoprotein that has increased or decreased in tissues or cells compared with normal control samples. In the present disclosure, as markers for a hepatocellular cancer, glycoproteins the expression level or the extent of glycosylation of which are decreased or increased are employed and include AFP, Alpha-2-antiplasmin (SERPINF2), Alpha-2-macroglobulin (A2M), Apolipoprotein B-100 (APOB), Beta-galactosidase (GLB1), Bone morphogenetic protein 1 (BMP1), Corticosteroid-binding globulin (SERPINA6), Complement factor H (CFH), Cholinesterase (BCHE), Clusterin (CLU), Collagen alpha-1(XII) chain (COL12A1), Carboxypeptidase N subunit 2 (CPN2), Versican core protein (VCAN), Receptor tyrosine-protein kinase erbB-3 (ERBB3), Coagulation factor V (F5), Coagulation factor XI (F11), Alpha-fetoprotein (AFP), Follistatin-related protein 1 (FSTL1), N-acetylglucosamine-6-sulfatase (GNS), G-protein coupled receptor 126 (GPR126), Heparin cofactor 2 (SERPIND1), Hypoxia up-regulated protein 1 (HYOU1), Integrin alpha-2 (ITGA2), Integrin alpha-3 (ITGA3), Integrin alpha-6 (ITGA6), Integrin alpha-M (ITGAM), Integrin beta-2 (ITGB2), Plasma kallikrein (KLKB1), Kinectin (KTN1), Lysosome-associated membrane glycoprotein 2 (LAMP2), Galectin-3-binding protein (LGALS3BP), Plexin-A1 (PLXNA1), Periostin (POSTN), Inactive tyrosine-protein kinase 7 (PTK7), Roundabout homolog 4 (ROBO4), Tenascin (TNC), Vitronectin (VTN).

In the present disclosure, the present markers may be used in alone or two or more markers may be used in combination to further improve the specificity and/or sensitivity. For example, two, three, four, five, six, seven or more markers may be combined. The person skilled in the art would be able to select the combination of markers that show a desired sensitivity and specificity using the methods such as Logistic regression analysis and/or analysis of the biological samples from the subjects including a normal person and patient using the methods such as described in the examples of the present disclosure.

In other aspect, the present disclosure relates to a method for screening a maker for cancer diagnosis. According to one embodiment, the method comprises steps of providing a protein(s) containing N-linked glycosylation motifs wherein the proteins are glycosylated at all or part of the motif, and the proteins are from a normal control sample and a cancer sample; de-glycosylating the proteins in the sample; fragmenting the de-glycosylated proteins; determining in the fragmented proteins the amount of the de-glycosylated peptide at the N-linked motif and the amount of the non-glycosylated peptide which does not contain the N-linked motif and the ratio therebetween; and selecting the protein as a marker if the ratio is changed in the sample compared to that of a control.

The elements recited in the methods are as described hereinbefore.

The proteins having N-linked glycosylation motif comprise glycoproteins are from a sample such as cancer tissues, cells or from bodily fluids such as blood or from a normal sample or from sample of a cured cancer patient, and the level and/or extent of which change, i.e., are increased or decreased compared to a control sample. These glycoproteins may be screened from the glycoproteins known in the art.

In other aspect, the present disclosure relates to a kit which is used for the present methods. The kit comprises an enzyme(s) for de-glycosylating the proteins or sample comprising NxST motif, an enzyme(s) for fragmenting the proteins and agents for quantifying the de-glycosylated fragments or peptide and the non-glycosylated fragment or peptide. The elements recited in the present kits are as described hereinbefore.

The present disclosure is further explained in more detail with reference to the following examples. These examples, however, should not be interpreted as limiting the scope of the present invention in any manner.

EXAMPLES

Example 1. Analysis of De-Glycosylated/Non-Glycosylated Peptides Using a Standard Glyco Proteins The following experiments was performed using a standard protein to confirm the possibility of discovering or developing markers based on the quantification of glycosylated peptides and de-glycosylated peptides using MRM technology and its use in diagnostics.

As shown in FIG. 1, MRM is a technology to quantify a relative or an absolute amount of proteins in biological fluids using Triple quadrupole as a mass spectrometry. MRM includes a first mass filter Quadruple 1 (Q1) filtering only the peptides with a specific m/z (mass/charge), Quadruple 2 (a collision cell) in which the peptides from Q1 are fragmented by electric energy and Quadruple 3 (Q3) which transmits only particular fragmented peptide ions. Then the ions transmitted through Q3 are shown as a peak of chromatogram at the detector. The area of the peak is calculated for the absolute or relative quantification of peptides. In case of glycosylated peptides, there are changes in the original mass of the peptide due to the glycan present in the glycosylated peptides. As a result, the glycosylated peptides cannot pass through a Q1 filter at the m/z value of the corresponding peptide and fails to enter into Q2 collision cell. Thus, the glycosylated peptides are not detected. In contrast, when the glycosylated peptides are de-glycosylated by treating them with a de-glycosylating enzyme such as PNGase-F, the glycans are removed at the N-glycosylation site (NxS/T) by which Asn (Asparagine, N) is changed to a deaminated form, i.e., Asp (Aspartic acid, D). The de-glycosylated peptides can thus be detected as a deaminated form of the peptide based on such principle.

Example 1-1 Standard Glycoproteins

Among the commercially available proteins which are purified and lyophilized, a protein in which both the glycosylated peptide having NxS/T motif and the non-glycosylated peptide without the motif are selected as predictable transitions in Skyline has been used as a standard.

In the present example, Invertase-1protein was used as a standard and the sequence is as shown in FIG. 2 in which the green indicates the sequence used in the analysis. The sequence of the standard glycosylated peptides 1 and 2 employed are NPVLAANSTQFR (SEQ ID NO: 104) and FATNTTLTK (SEQ ID NO: 106), respectively. When the peptides are de-glycosylated, Asn residues are converted to Asp resulting in the peptide sequence of NPVLAADSTQFR (SEQ ID NO: 105) and FATDTTLTK (SEQ ID NO: 107), respectively. The standard non-glycosylated peptides 1 and 2 employed are IEIYSSDDLK (SEQ ID NO: 108) and VVDFGK (SEQ ID NO: 109), respectively.

Example 1-2 Selection of the Theoretical Transition (Q1/Q3) of the Standard Protein The native form of the sequence of the standard protein and the conversion form thereof in which N is changed to D at NxS/T motif were imported into Skyline (https://brendanx-uw1.gs.washington.edu/labkey/project/home/software/Skyline/begin.view) program to select a theoretical transition value. At the same time, synthetic peptides with the same sequence except that $^{12}C$ and $^{14}N$ atoms in Arg (R) and Lys (K) residues at the C-terminal region were heavy labelled with $^{13}$C and $^{15}$N were used to confirm that the peptides detected are actually from the peptides of interest to be detected.

That is, the heavy labelled peptide and the endogenous peptide share the same sequence and have the identical hydrophobicity. Thus they can be detected on LC-column (C18) since they are eluted at the same retention time.

As a result of the selection, Q1 difference of 0.49 Da and Q3 difference of 0.98 Da between the native and conversion sequence have been found. The difference between the endogenous peptide and the heavy labelled peptide were found to be 4.00 Da (5.00 Da) in Q1 and 8.01 Da (10.01 Da) in Q3. The transition analysis results are as below in Table 2.

(dithiothreitol) in Tris pH 8.0 and reduced at 37° C. for 60 min. Then the product was alkylated with IAA (iodoacetamide) at the final concentration of 50 mM at RT for 30 min. Then the product was diluted with 100 mM Tris pH 8.0 to bring the concentration of Urea not more than 0.6M. Then the de-glycosylated peptides were treated with 2 μl (500,000 units/ml) of PNGase-F (Peptide N Glycosidase) (NEW ENGLAND BioLabs Inc. P0704L) and incubated at 37° C. for 16 hrs, which were then treated with trypsin at a ratio of 1:50 (w/w) trypsin to peptides and incubated at 37° C. for 12 hrs. Then the resulting products were treated with a formic acid solution at the final concentration of 5%. And as a

TABLE 2

| | | | Native sequence | | | | | | Conversion sequence | |
|---|---|---|---|---|---|---|---|---|---|---|
| Peptide sequence | Isotype | Ion Name | Precursor Ion (Q1) | Product Ion (Q2) | Peptide sequence | Isotype | Ion Name | Precursor Ion (Q1) | Product Ion (Q2) | |
| NPVLAAASTQFR (SEQ ID NO: 104) | light | y9 | 699.349125 | 10077.526869 | NPVLAADSTQFR (SEQ ID NO: 105) | light | y9 | 659.841133 | 1008.510885 | |
| | light | y8 | 699.349125 | 894.442805 | | light | y8 | 699.841133 | 899.426821 | |
| | light | y7 | 699.349125 | 823.405691 | | light | y7 | 659.841133 | 824.382707 | |
| | light | y6 | 699.349125 | 752.368578 | | light | y6 | 699.841133 | 753.352593 | |
| | light | y5 | 699.349125 | 638.32565 | | light | y5 | 659.841133 | 638.32565 | |
| NPVLAAASTQFR (SEQ ID NO: 104) | heavy | y9 | 664.35326 | 1017.535138 | NPVLAADSTQFR (SEQ ID NO: 105) | heavy | y9 | 664.845268 | 1018.519154 | |
| | heavy | y8 | 664.35326 | 904.453074 | | heavy | y8 | 664.845268 | 905.43903 | |
| | heavy | y7 | 664.35326 | 833.41396 | | heavy | y7 | 664.845268 | 834.397976 | |
| | heavy | y6 | 664.35326 | 762.376847 | | heavy | y6 | 664.845268 | 763.360862 | |
| | heavy | y5 | 664.35326 | 628.333919 | | heavy | y5 | 664.845268 | 648.333919 | |
| IEIYSSDDLK (SEQ ID NO: 108) | light | y9 | 591.798068 | 1069.904798 | IEIYSSDDLK (SEQ ID NO: 108) | light | y9 | 591.798068 | 1069.504796 | |
| | light | y8 | 591.798068 | 941.462203 | | light | y8 | 591.798068 | 941.462203 | |
| | light | y7 | 591.799068 | 827.378139 | | light | y7 | 591.798068 | 827.378139 | |
| | light | y6 | 591.799068 | 664.314811 | | light | y6 | 591.798068 | 664.314811 | |
| | light | b3 | 591.798068 | 356.217997 | | light | b3 | 591.798068 | 356.217997 | |
| IEIYSSDDLK (SEQ ID NO: 108) | heavy | y9 | 595.995168 | 1077.518995 | IEIYSSDDLK (SEQ ID NO: 108) | heavy | y9 | 595.805168 | 1077.518995 | |
| | heavy | y8 | 595.805168 | 948.476402 | | heavy | y8 | 595.905168 | 948.876422 | |
| | heavy | y7 | 595.805168 | 835.792328 | | heavy | y7 | 595.805168 | 835.392338 | |
| | heavy | y6 | 595.805168 | 672.32901 | | heavy | y6 | 595.805168 | 672.32901 | |
| | heavy | b3 | 595.805168 | 355.217997 | | heavy | b3 | 595.805168 | 356.217997 | |
| VVDFGK (SEQ ID NO: 109) | light | y5 | 332.686864 | 565.298038 | WDFGK (SEQ ID NO: 109) | light | y5 | 332.686854 | 565.299038 | |
| | light | y4 | 322.686864 | 466.229624 | | light | y4 | 332.686854 | 466.243823 | |
| | light | y3 | 322.686864 | 351.302681 | | light | y3 | 332.686854 | 351.202681 | |
| | light | y2 | 322.686864 | 204.134257 | | light | y2 | 332.686854 | 204.134267 | |
| | light | b2 | 332.686864 | 199.144104 | | light | b2 | 332.686854 | 199.144104 | |
| VVDFGK (SEQ ID NO: 109) | heavy | y5 | 336.699964 | 573.312237 | VVDFGK (SEQ ID NO: 109) | heavy | y5 | 336.693364 | 573.312237 | |
| | heavy | y4 | 336.699964 | 474.243823 | | heavy | y4 | 336.693364 | 474.243823 | |
| | heavy | y3 | 336.699964 | 393.21589 | | heavy | y3 | 336.693964 | 399.21688 | |
| | heavy | y2 | 336.699964 | 212.3484688 | | heavy | y2 | 336.693964 | 212.148666 | |
| | heavy | b2 | 336.699964 | 199.144104 | | heavy | b2 | 338.693964 | 199.144104 | |
| FATDTTLTK (SEQ ID NO: 106) | light | y8 | 498.771657 | 849.467623 | FATDTTLTK (SEQ ID NO: 107) | light | y8 | 499.263664 | 890.451639 | |
| | light | y7 | 498.771657 | 778.430509 | | light | y7 | 499.263664 | 779.414525 | |
| | light | y6 | 498.771657 | 677.382831 | | light | y6 | 499.263664 | 678.366845 | |
| | light | y5 | 498.771657 | 593.339903 | | light | y5 | 499.263664 | 563.339903 | |
| | light | y4 | 498.771657 | 462.292225 | | light | y4 | 499.263664 | 462.292225 | |
| FATATTLTK (SEQ ID NO: 106) | heavy | y8 | 502.778756 | 857.481822 | FATATTLTK (SEQ ID NO: 107) | heavy | y8 | 503.270764 | 858.465838 | |
| | heavy | y7 | 502.778756 | 785.444708 | | heavy | y7 | 503.270764 | 787.428724 | |
| | heavy | y6 | 502.778756 | 655.39703 | | heavy | y6 | 503.270764 | 686.381045 | |
| | heavy | y5 | 502.778756 | 571.354102 | | heavy | y5 | 503.270764 | 571.354102 | |
| | heavy | y4 | 502.778756 | 470.306424 | | heavy | y4 | 503.270764 | 470.306424 | |

Example 1-3 MRM Analysis of the Standard Glycosylated Protein 1-3-1 Preparation of the Standard Glycoprotein Hundred μg of standard protein was treated with urea and DTT at the final concentration of 6M urea/20 mM DTT control the glycosylated peptides was treated with 2 μl of water under the same condition. Then desalting reaction was performed as follows using OASIS cartridge (Waters, USA) as suggested by the manufacturer's instruction. The desalted peptides were dissolved in Sol A buffer (97% D.W, 3% ACN, 0.1% formic acid) followed by a centrifugation at 15,000 rpm for 60 min, and then used for MRM analysis.

1-3-2 Preparation of Sample for MRM Analysis

To confirm the possibility of the quantification, experiments to confirm the linearity of the heavy labelled synthetic peptide to the target peptide as follows. For this, a serious dilution of 0, 4, 13, 40, 120, 370 fmol of the heavy labelled synthetic peptide was prepared, to which a 370 nmol of the target peptide corresponding to the standard glycosylated protein was added for the analysis. For the glycosylated standard glycoprotein sample, heavy labelled synthetic peptide of N-form having Asn residue was used. For the de-glycosylated standard glycoprotein sample, heavy labelled synthetic peptide of D-form having Asp residue was used. All the experiments were repeated 3 times.

1-3-3 Condition for MRM Analysis

Liquid chromatography (LC) 1260 capillary LC system from Agilent was used. For the peptide separation, Capillary RR 0.3×150, 3.5 μm (Cat.N 5064-8261) was used. Five microliter of peptide sample was directly injected into the column without passing through a trap column and eluted at a flow rate of 20 L/min, Column was equilibrated with SolA (97% Distilled Water, 3% acetonitrile, 0.1% formic acid) for 10 min and eluted with SolB (3% Distilled Water, 97% acetonitrile, 0.1% formic acid) in 45 min and then on a linear gradient of 5% to 60% and of 85% in 5 min.

Mass spectrometry 6490-Triple quadrupole (QQQ) from Agilent technology was used to monitor the transition of the selected protein under MRM mode. The settings were as follows: gas temperature of 200° C., gas flow of 14 L/min, nebulizer at 20 psi, sheath gas temperature of 250° C. and sheath gas flow of 11 L/min. The voltage applied for the capillary and nozzle was 3000V.

The unit resolution of 0.7 Da was used for Quadruple 1(Q1) and Quadruple 3 (Q3). The dwell time was set to 2 sec for a total cycle in an unscheduled MRM mode. Then the retention time was selected after the analysis for all the target peptides were completed, based on which the analysis were repeated 3 times at the window size 3 min.

1-3-4 MRM Analysis Results

The results of MRM analysis for the standard glycoprotein are shown in FIGS. 3 to 7.

Figure 3A:
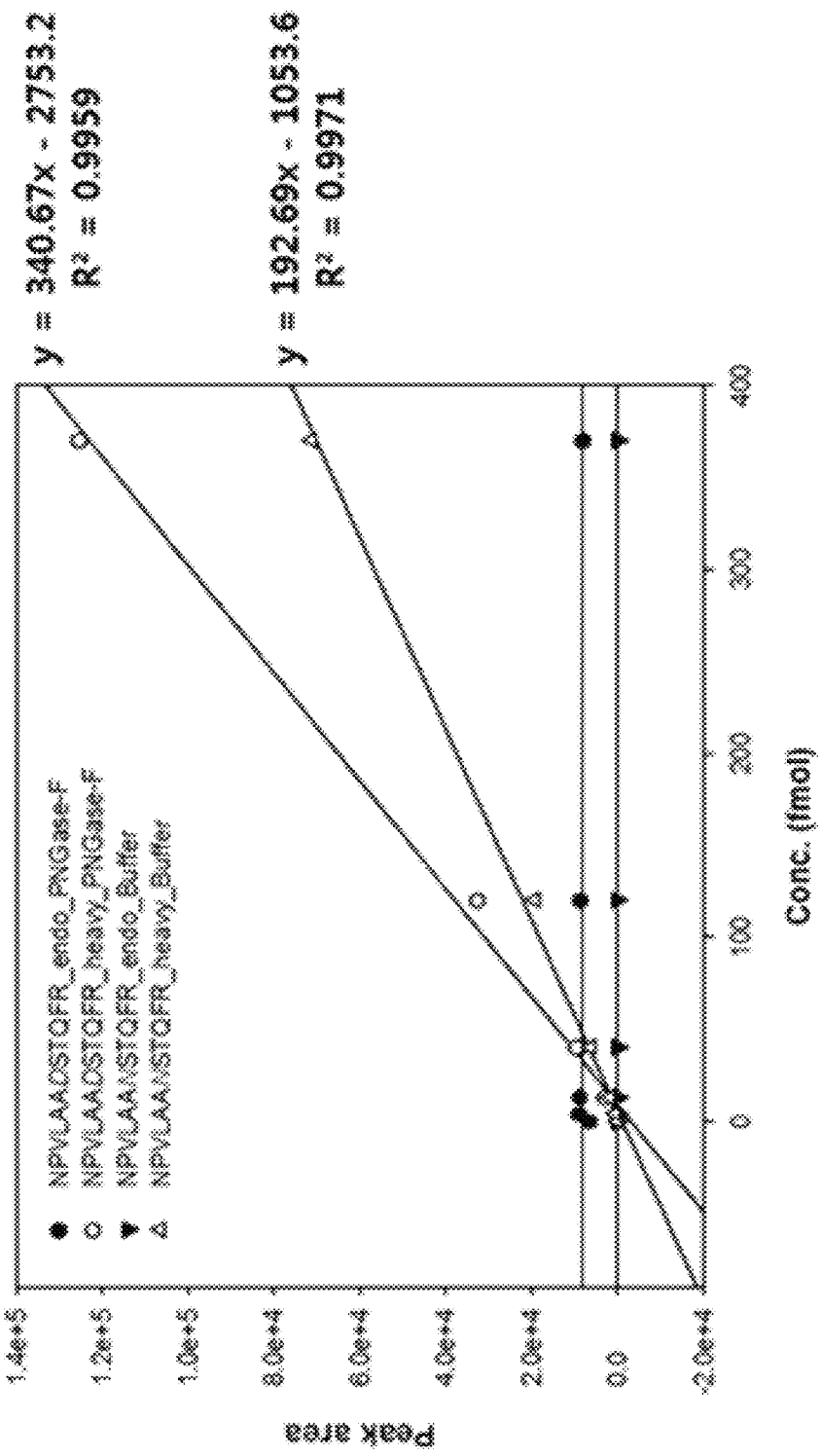
FIGS. 3a to 3c are graphs showing the results of MRM analysis of the glycosylated peptide 1 (NPVLAANSTQFR) (SEQ ID NO: 104) of the glycosylated standard protein, in which the peak area according to the concentrations are represented.
Figure 3B:
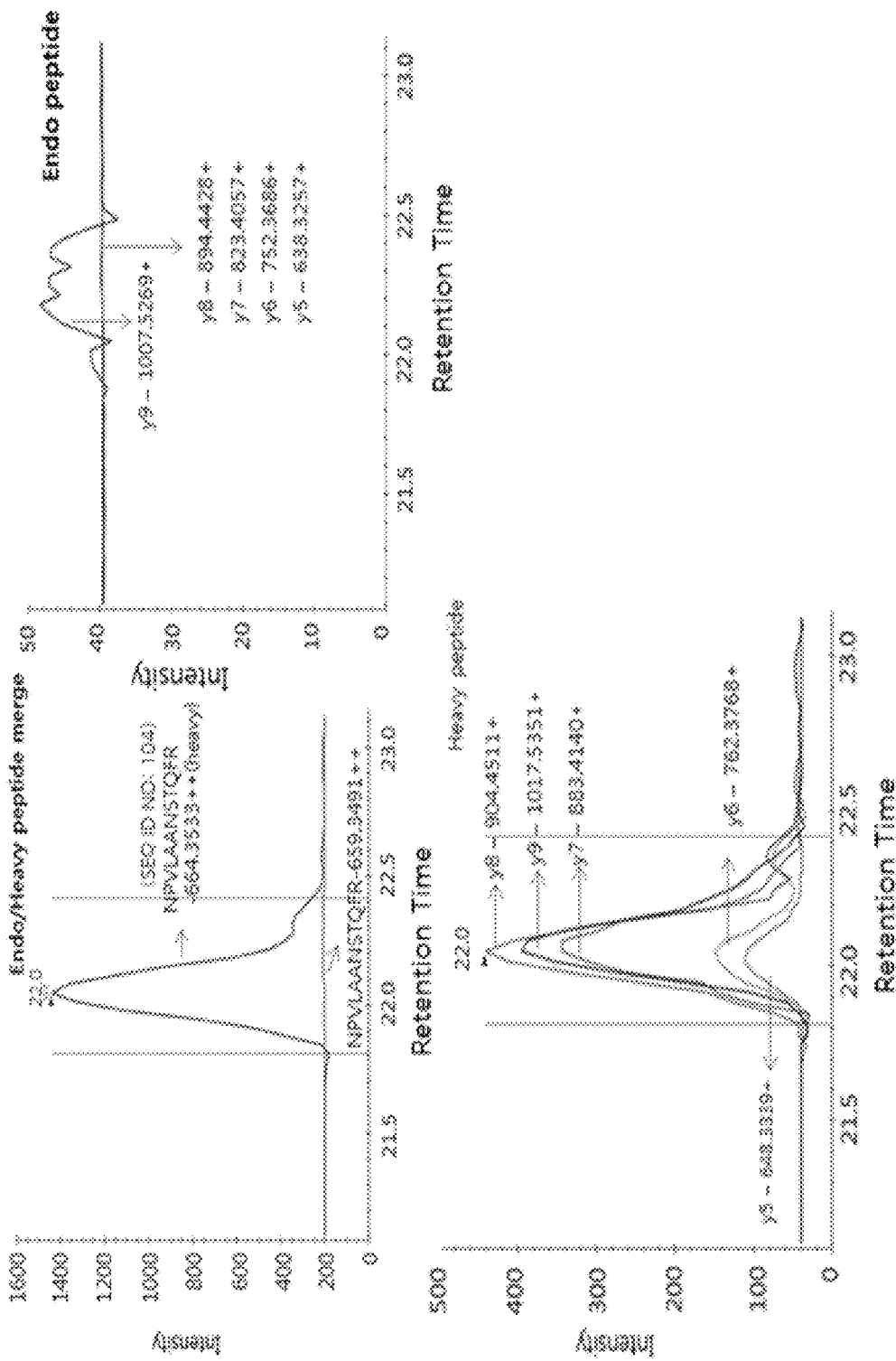
Figure 3C:
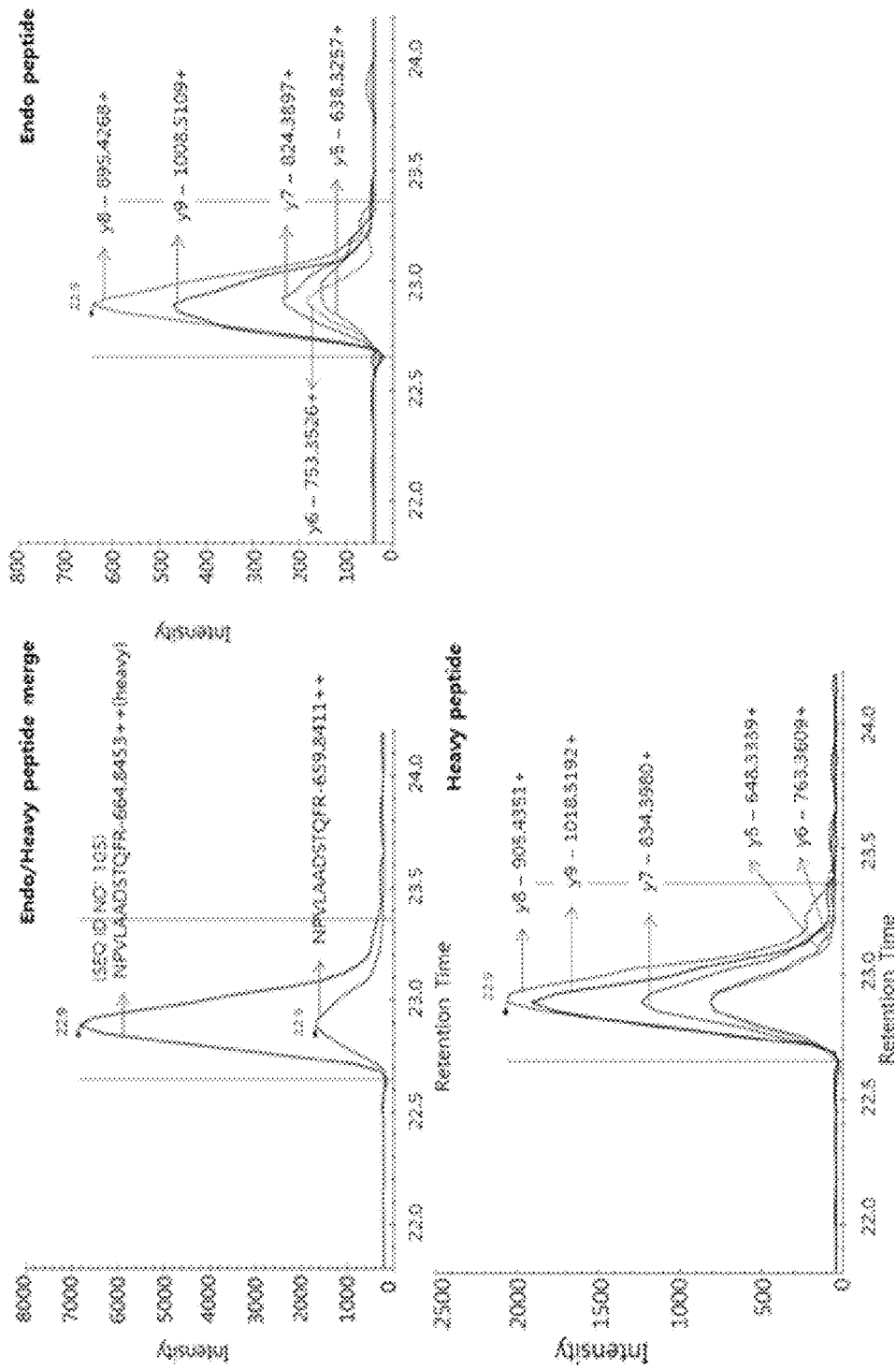
Figure 4B:
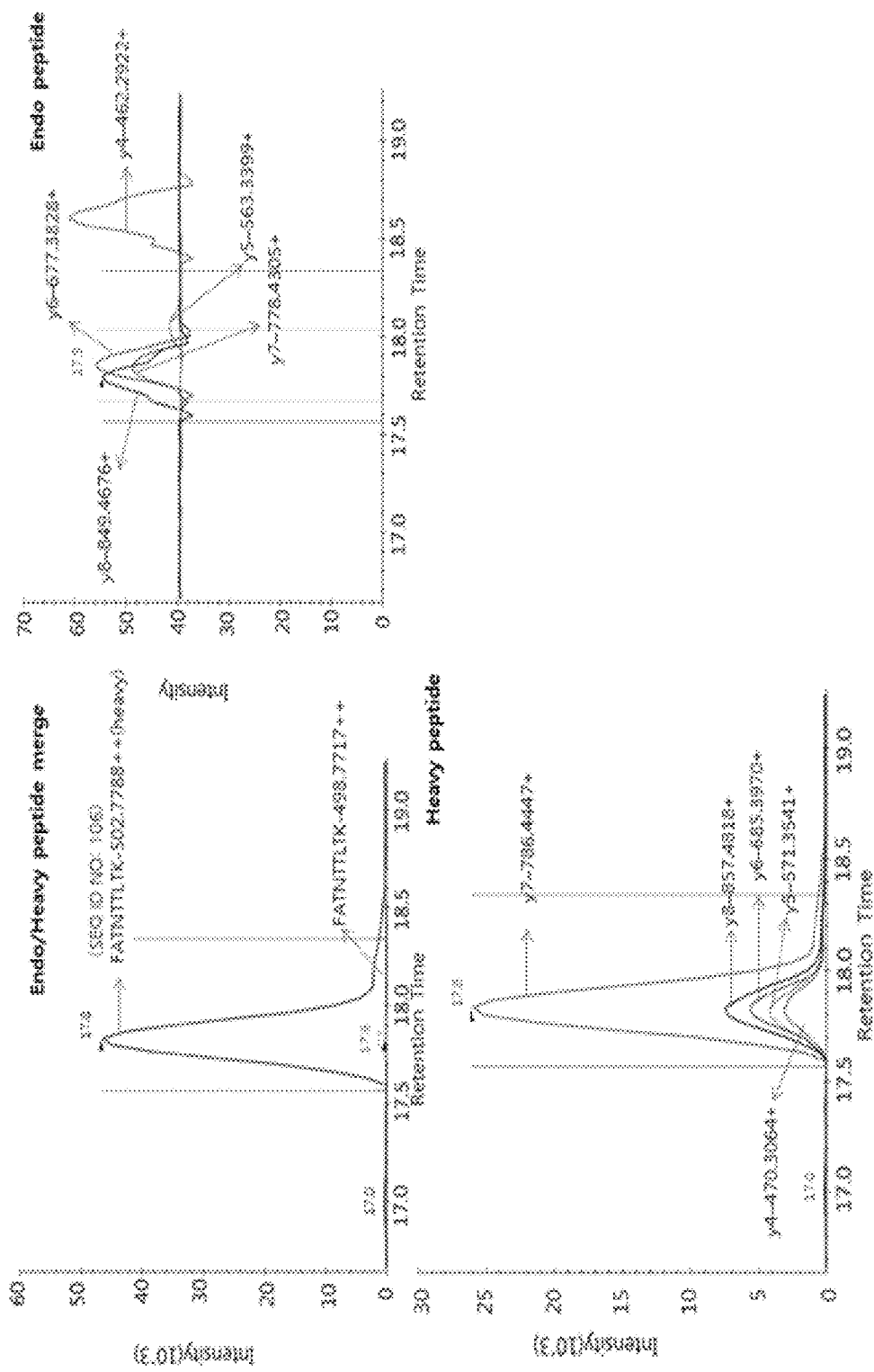
Figure 4C:
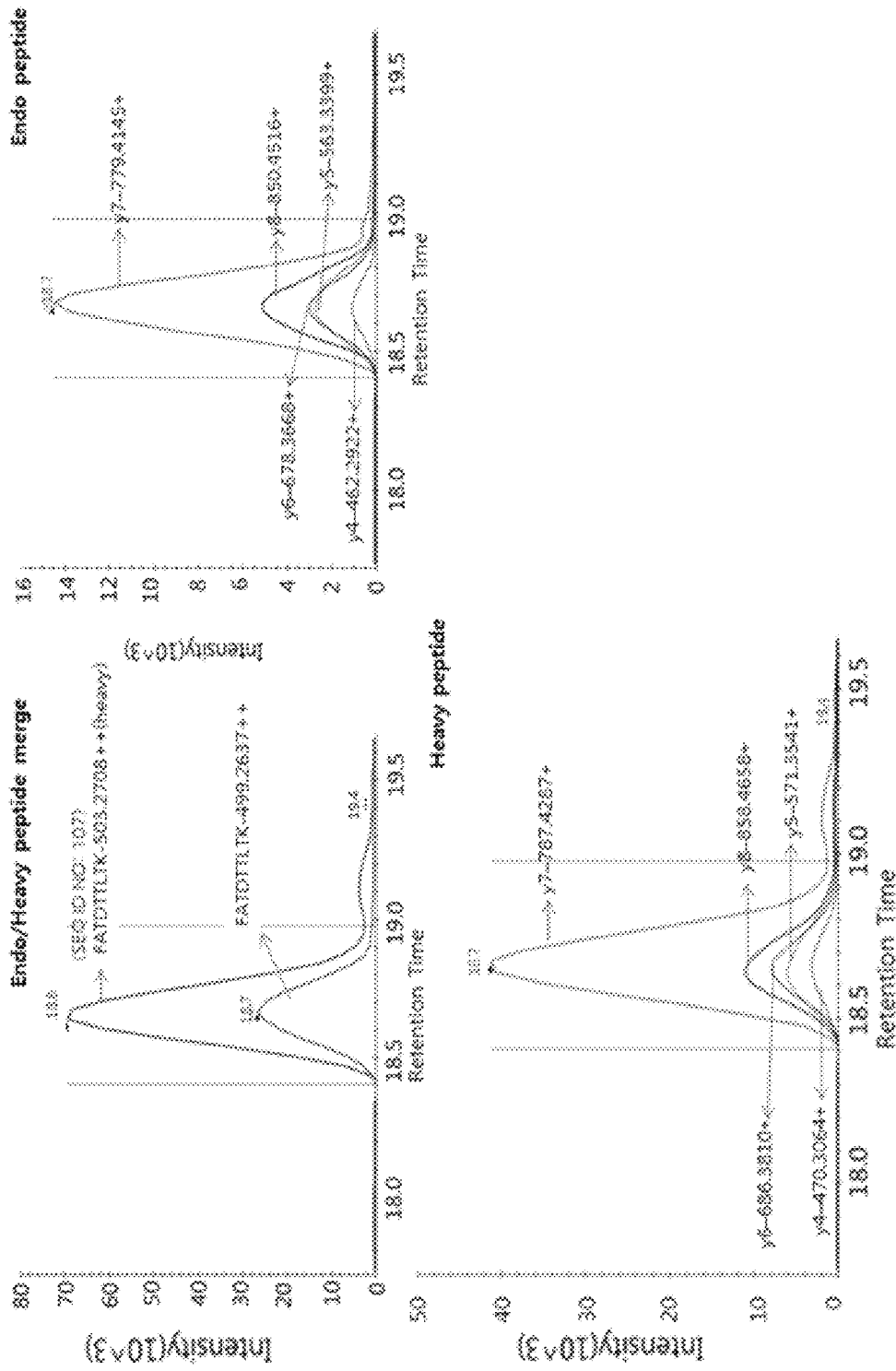

Results of the analysis performed on NPVLAANSTQFR (SEQ ID NO: 104) (the glycosylated peptide 1)/FATNTTLTK (SEQ ID NO: 106) (the glycosylated peptide 2) are shown in FIGS. 3 and 4, Tables 3-1 and 3-2 and Tables 4-1 and 4-2. When the serially diluted heavy labelled synthetic peptide in D-form was added to the de-glycosylated sample, it was confirmed that the endogenous peptide from the standard glycoprotein and the heavy labelled peptide were co-eluted at the identical time. Also the strength of five product ion type was confirmed to be identical. And the linearity ($R^2=0.9959$, $0.9994$) of the heavy labelled synthetic peptide was confirmed. When the serially diluted heavy labelled synthetic peptide in N-form was added to the glycosylated sample, the endogenous peptide from the standard glycoprotein was not observed and only the heavy labelled peptide was detected. The linearity of $R^2=0.9971$, $0.9958$ was found.

TABLE 3-1

NPVLAANSTQFR (SEQ ID NO: 104)_endo_Buffer

| Heavy conc. (fmol) | Peak area | | | Endo conc. (nmol) | Peak area | | |
|---|---|---|---|---|---|---|---|
| | Average | STDEV | CV (%) | | Average | STDEV | CV (%) |
| 0.0 | 0.0 | 0.0 | 0.0 | 370.0 | 0.0 | 0.0 | 0.0 |
| 4.0 | 567.0 | 140.5 | 24.8 | 370.0 | 0.0 | 0.0 | 0.0 |
| 13.0 | 1803.0 | 439.7 | 24.4 | 370.0 | 0.0 | 0.0 | 0.0 |
| 40.0 | 6312.7 | 985.4 | 15.6 | 370.0 | 0.0 | 0.0 | 0.0 |
| 120.0 | 19215.0 | 2691.7 | 14.0 | 370.0 | 0.0 | 0.0 | 0.0 |
| 370.0 | 71184.7 | 2395.1 | 3.4 | 370.0 | 0.0 | 0.0 | 0.0 |

TABLE 3-2

NPVLAADSTQFR (SEQ ID NO: 105)_heavy_PNGase-F

| Heavy conc. (fmol) | Peak area | | | Endo conc. (nmol) | Peak area | | |
|---|---|---|---|---|---|---|---|
| | Average | STDEV | CV (%) | | Average | STDEV | CV (%) |
| 0 | 0.0 | 0.0 | 0.0 | 370.0 | 6543.0 | 535.2 | 8.2 |
| 4 | 0.0 | 0.0 | 0.0 | 370.0 | 8770.7 | 1578.1 | 18.0 |
| 13 | 2745.0 | 992.7 | 36.2 | 370.0 | 8679.7 | 1077.0 | 12.4 |
| 40 | 9385.0 | 1541.2 | 16.4 | 370.0 | 8590.7 | 921.5 | 10.7 |
| 120 | 32455.0 | 757.8 | 2.3 | 370.0 | 8466.7 | 546.7 | 6.5 |
| 370 | 125243.3 | 4397.1 | 3.5 | 370.0 | 8050.0 | 1124.4 | 14.0 |

TABLE 4-1

FATNTTLTK (SEQ ID NO: 106)_endo_Buffer

| Heavy conc. (fmol) | Peak area | | | Endo conc. (nmol) | Peak area | | |
|---|---|---|---|---|---|---|---|
| | Average | STDEV | CV (%) | | Average | STDEV | CV (%) |
| 0.0 | 0.0 | 0.0 | 0.0 | 370.0 | 0.0 | 0.0 | 0.0 |
| 4.0 | 3251.7 | 377.5 | 11.6 | 370.0 | 0.0 | 0.0 | 0.0 |
| 13.0 | 8573.7 | 828.6 | 9.7 | 370.0 | 0.0 | 0.0 | 0.0 |
| 40.0 | 29945.7 | 2731.4 | 9.1 | 370.0 | 0.0 | 0.0 | 0.0 |
| 120.0 | 90011.0 | 8249.9 | 9.2 | 370.0 | 0.0 | 0.0 | 0.0 |
| 370.0 | 347197.7 | 38220.6 | 11.0 | 370.0 | 0.0 | 0.0 | 0.0 |

TABLE 4-2

FATDTTLTK (SEQ ID NO: 107)_heavy_PNGase-F

| Heavy conc. (fmol) | Peak area | | | Endo conc. (nmol) | Peak area | | |
|---|---|---|---|---|---|---|---|
| | Average | STDEV | CV (%) | | Average | STDEV | CV (%) |
| 0 | 0.0 | 0.0 | 0.0 | 370.0 | 211051.0 | 11726.5 | 5.6 |
| 4 | 5316.0 | 329.5 | 6.2 | 370.0 | 221477.7 | 10614.3 | 4.8 |
| 13 | 15605.3 | 1789.6 | 11.5 | 370.0 | 224643.3 | 3350.8 | 1.5 |
| 40 | 51313.7 | 3243.6 | 6.3 | 370.0 | 231082.7 | 12938.0 | 5.6 |
| 120 | 178115.7 | 6992.8 | 3.9 | 370.0 | 212931.0 | 19169.8 | 9.0 |
| 370 | 585547.3 | 24593.9 | 4.2 | 370.0 | 221705.7 | 19232.9 | 8.7 |

Figure 5A:
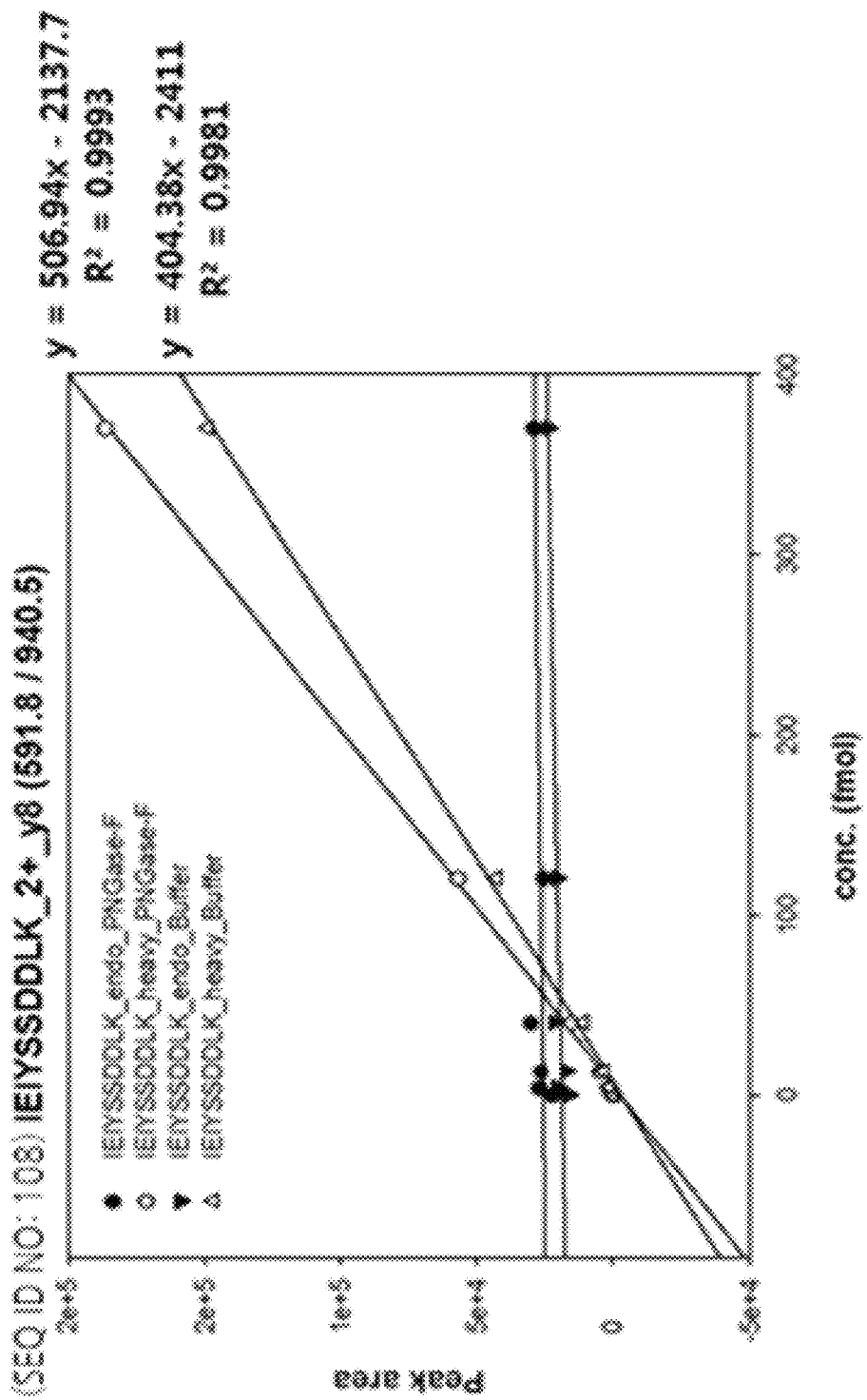
Figure 5C:
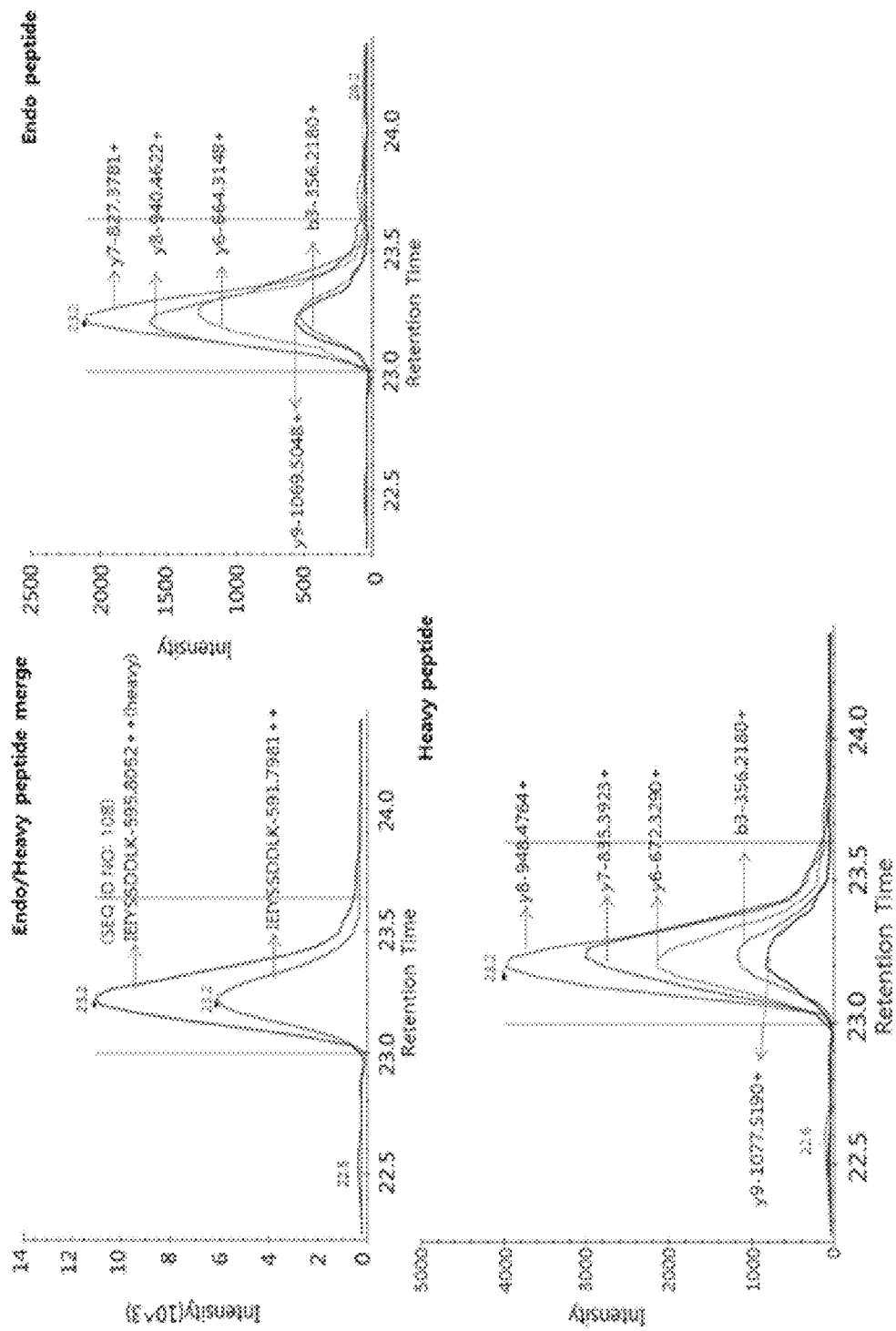
Figure 6A:
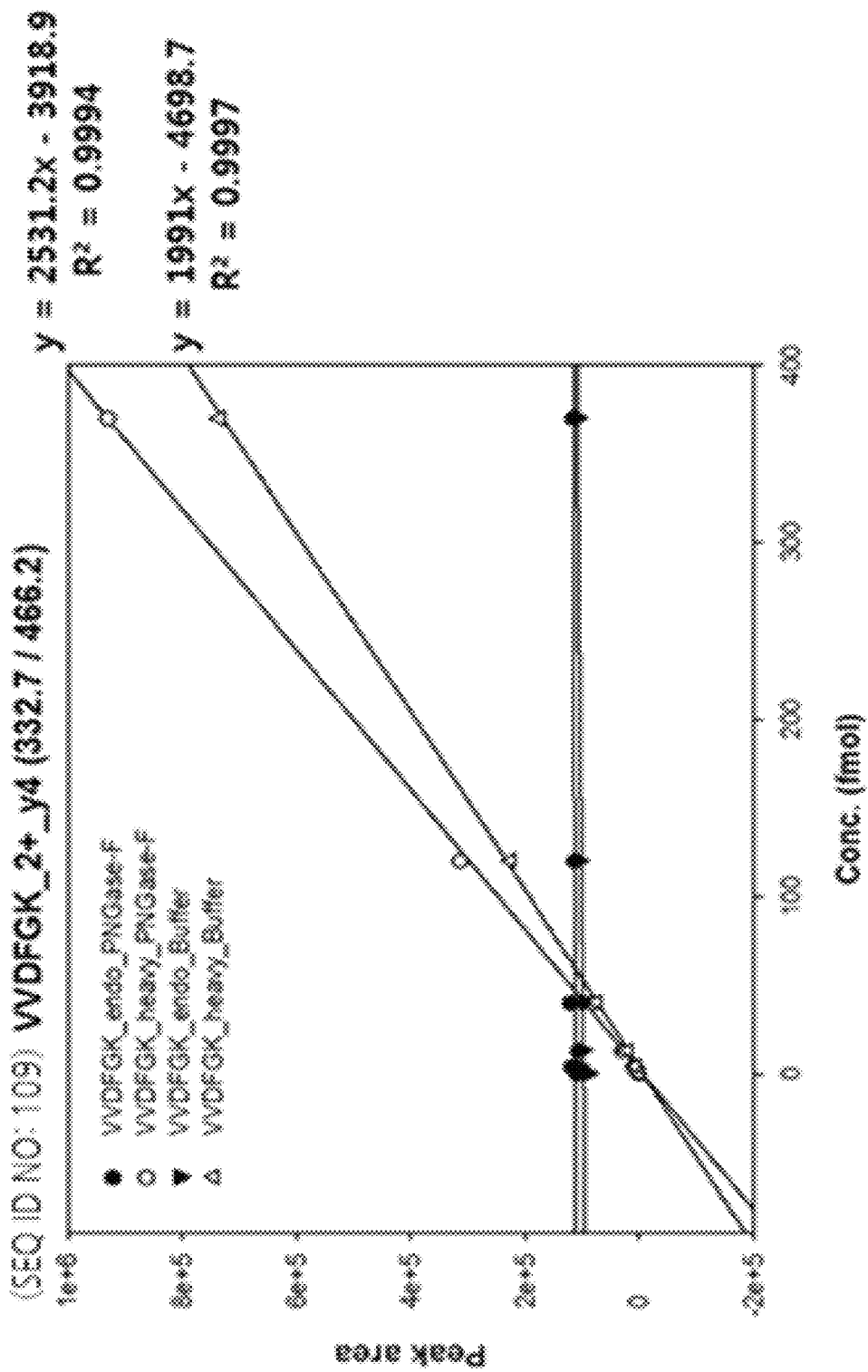
FIGS. 6a to 6c are graphs showing the results of MRM analysis of the non-glycosylated peptide 2 (VVDFGK) (SEQ ID NO: 109) of the glycosylated standard protein, in which the peak area according to the concentrations are represented.
Figure 6B:
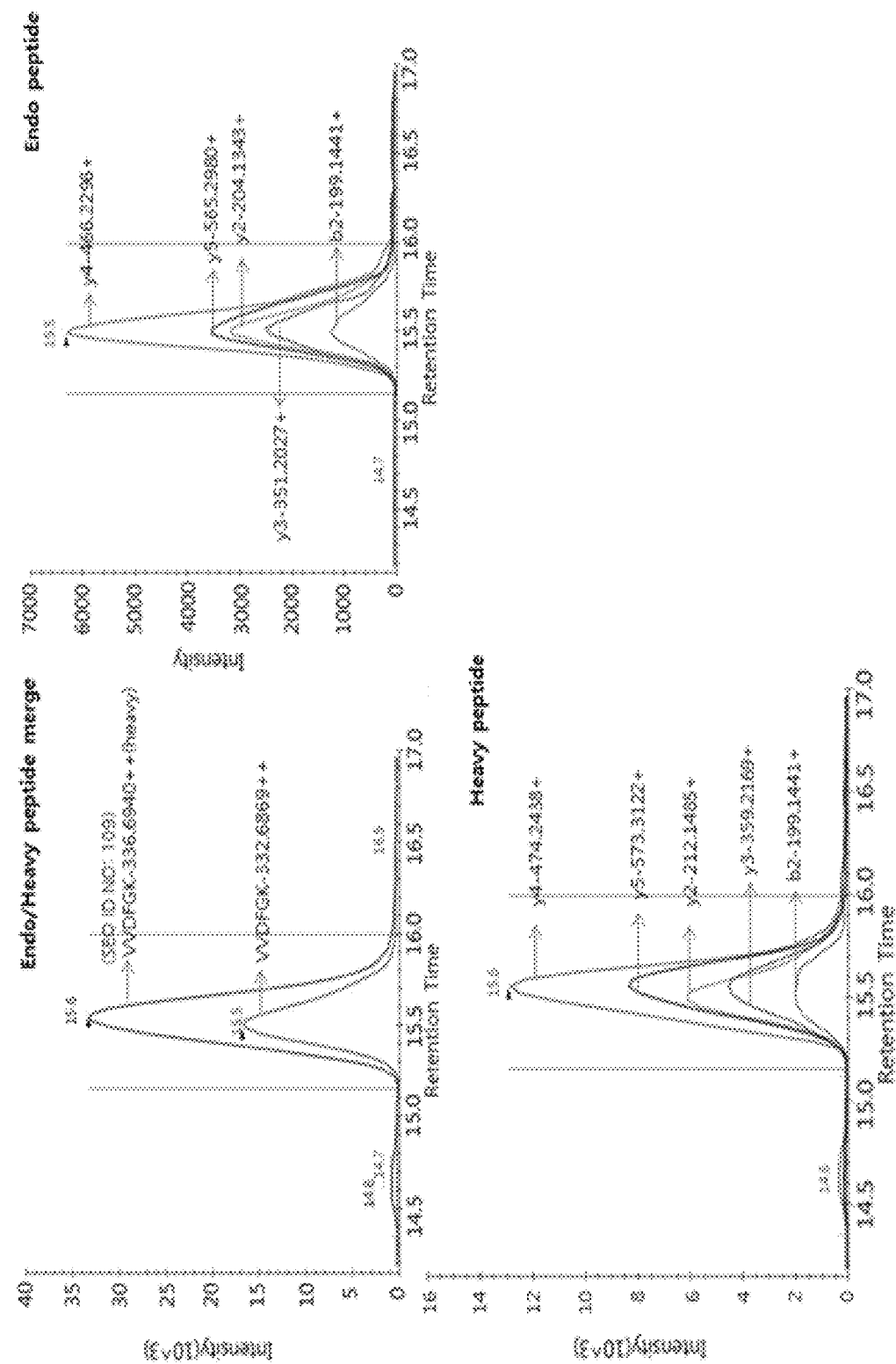
Figure 6C:
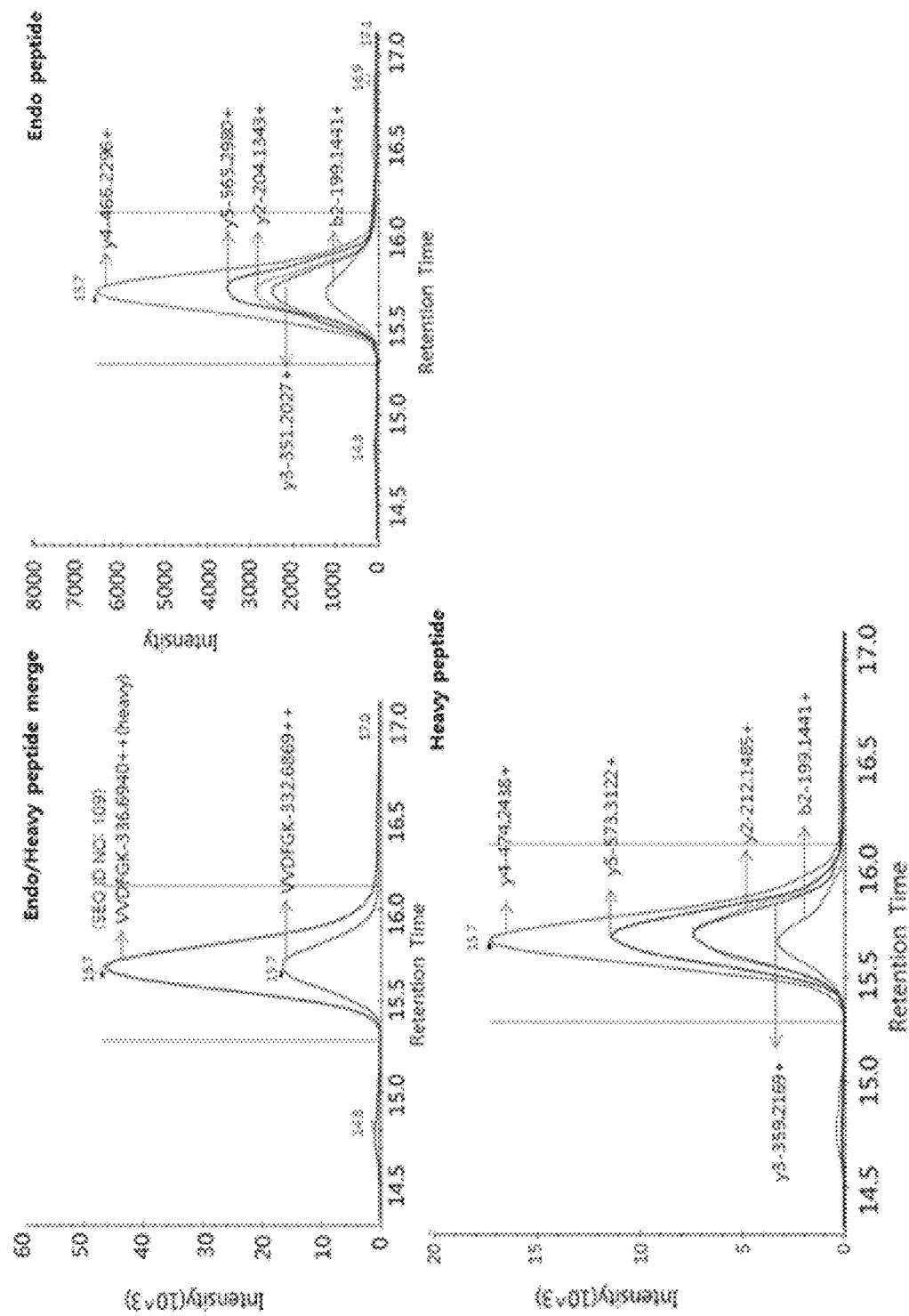

Results of the analysis performed on the non-glycosylated peptides IEIYSSDDLK (SEQ ID NO: 108)/VVDFGK (SEQ ID NO: 109) are shown in FIG. 5 and Tables 5-1 and 5-2, and Tables 6-1 and 6-2.

When the serially diluted heavy labelled peptide was added to the de-glycosylated and the glycosylated samples, the endogenous peptide from the standard glycoprotein and the heavy labelled peptide were co-eluted at the identical time. Also the strength of five product ion type was confirmed to be identical. The linearity of the heavy labelled synthetic peptide was confirmed to be $R^2=0.9993$, $0.9994$/$R^2=0.9981$, $0.9997$. Further the endogenous peptides were found to have a strength that is lower than the de-glycosylated sample treated with PNGase-F.

TABLE 5-1

| VVDFGK (SEQ ID NO: 109)_heavy_PNGase-F | | | | | | | |
|---|---|---|---|---|---|---|---|
| Heavy conc. | Peak area | | | Endo conc. | Peak area | | |
| (fmol) | Average | STDEV | CV (%) | (nmol) | Average | STDEV | CV (%) |
| 0 | 0.0 | 0.0 | 0.0 | 370.0 | 108440.0 | 6087.6 | 5.6 |
| 4 | 8115.3 | 419.8 | 5.2 | 370.0 | 117271.7 | 3679.3 | 3.1 |
| 13 | 28533.7 | 1532.7 | 5.4 | 370.0 | 105682.0 | 5422.9 | 5.1 |
| 40 | 81770.0 | 3646.6 | 4.5 | 370.0 | 118207.0 | 4490.0 | 3.8 |
| 120 | 312418.0 | 7315.0 | 2.3 | 370.0 | 113168.7 | 466.2 | 0.4 |
| 370 | 930225.7 | 11860.0 | 1.3 | 370.0 | 113721.0 | 7408.0 | 6.5 |

TABLE 5-2

| IEIYSSDDLK (SEQ ID NO: 107)_endo_Buffer | | | | | | | |
|---|---|---|---|---|---|---|---|
| Heavy conc. | Peak area | | | Endo conc. | Peak area | | |
| (fmol) | Average | STDEV | CV (%) | (nmol) | Average | STDEV | CV (%) |
| 0.0 | 0.0 | 0.0 | 0.0 | 370.0 | 16515.0 | 907.5 | 5.5 |
| 4.0 | 1265.7 | 405.5 | 32.0 | 370.0 | 20640.7 | 1143.2 | 5.5 |
| 13.0 | 3385.3 | 302.5 | 8.9 | 370.0 | 17470.3 | 2239.6 | 12.8 |
| 40.0 | 10699.0 | 2104.3 | 19.7 | 370.0 | 21598.0 | 910.4 | 4.2 |
| 120.0 | 42808.7 | 3793.7 | 8.9 | 370.0 | 20738.0 | 1253.4 | 6.0 |
| 370.0 | 148574.0 | 2126.4 | 1.4 | 370.0 | 23795.3 | 838.5 | 3.5 |

TABLE 6-1

| IEIYSSDDLK (SEQ ID NO: 108)_heavy_PNGase-F | | | | | | | |
|---|---|---|---|---|---|---|---|
| Heavy conc. | Peak area | | | Endo conc. | Peak area | | |
| (fmol) | Average | STDEV | CV (%) | (nmol) | Average | STDEV | CV (%) |
| 0 | 0.0 | 0.0 | 0.0 | 370.0 | 22047.3 | 342.0 | 1.6 |
| 4 | 1457.0 | 534.5 | 36.7 | 370.0 | 27167.3 | 1216.9 | 4.5 |
| 13 | 4585.0 | 237.8 | 5.2 | 370.0 | 26529.3 | 3219.1 | 12.1 |
| 40 | 15154.0 | 1538.5 | 10.2 | 370.0 | 30355.7 | 1660.5 | 5.5 |
| 120 | 56990.0 | 3247.2 | 5.7 | 370.0 | 25508.3 | 1855.0 | 7.3 |
| 370 | 186285.0 | 10110.8 | 5.4 | 370.0 | 29249.3 | 2171.6 | 7.4 |

TABLE 6-2

| VVDFGK (SEQ ID NO: 109)_heavy_PNGase-F | | | | | | | |
|---|---|---|---|---|---|---|---|
| Heavy conc. | Peak area | | | Endo conc. | Peak area | | |
| (fmol) | Average | STDEV | CV (%) | (nmol) | Average | STDEV | CV (%) |
| 0 | 0.0 | 0.0 | 0.0 | 370.0 | 108440.0 | 6087.6 | 5.6 |
| 4 | 8115.3 | 419.8 | 5.2 | 370.0 | 117271.7 | 3679.3 | 3.1 |
| 13 | 28533.7 | 1532.7 | 5.4 | 370.0 | 105682.0 | 5422.9 | 5.1 |
| 40 | 81770.0 | 3646.6 | 4.5 | 370.0 | 118207.0 | 4490.0 | 3.8 |
| 120 | 312418.0 | 7315.0 | 2.3 | 370.0 | 113168.7 | 466.2 | 0.4 |
| 370 | 930225.7 | 11860.0 | 1.3 | 370.0 | 113721.0 | 7408.0 | 6.5 |

Figure 7:
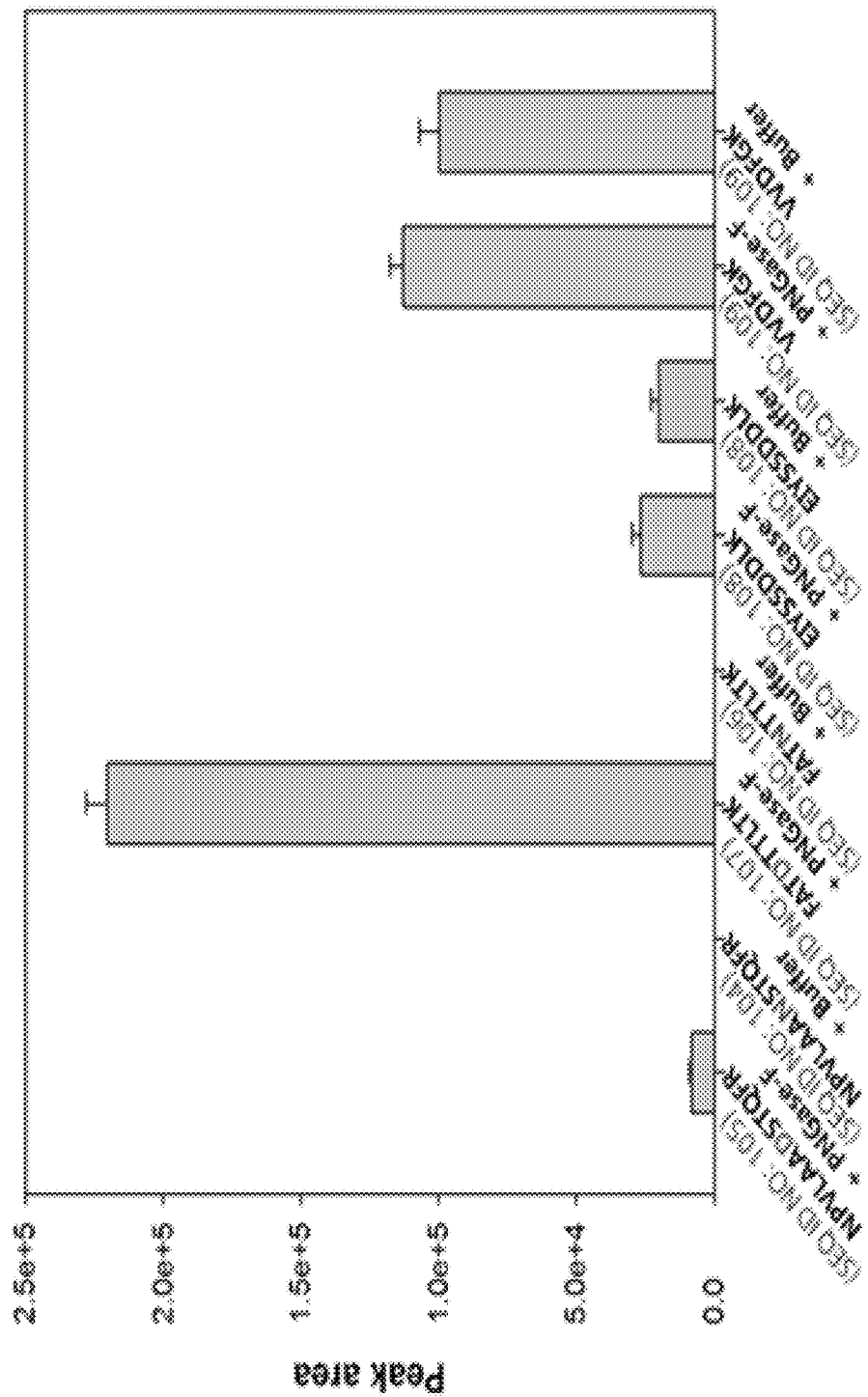
FIG. 7 is a graph showing the peak area obtained from MRM analysis of the endogenous peptides corresponding to each target peptide as in FIGS. 3 to 6.
Figure 9A:
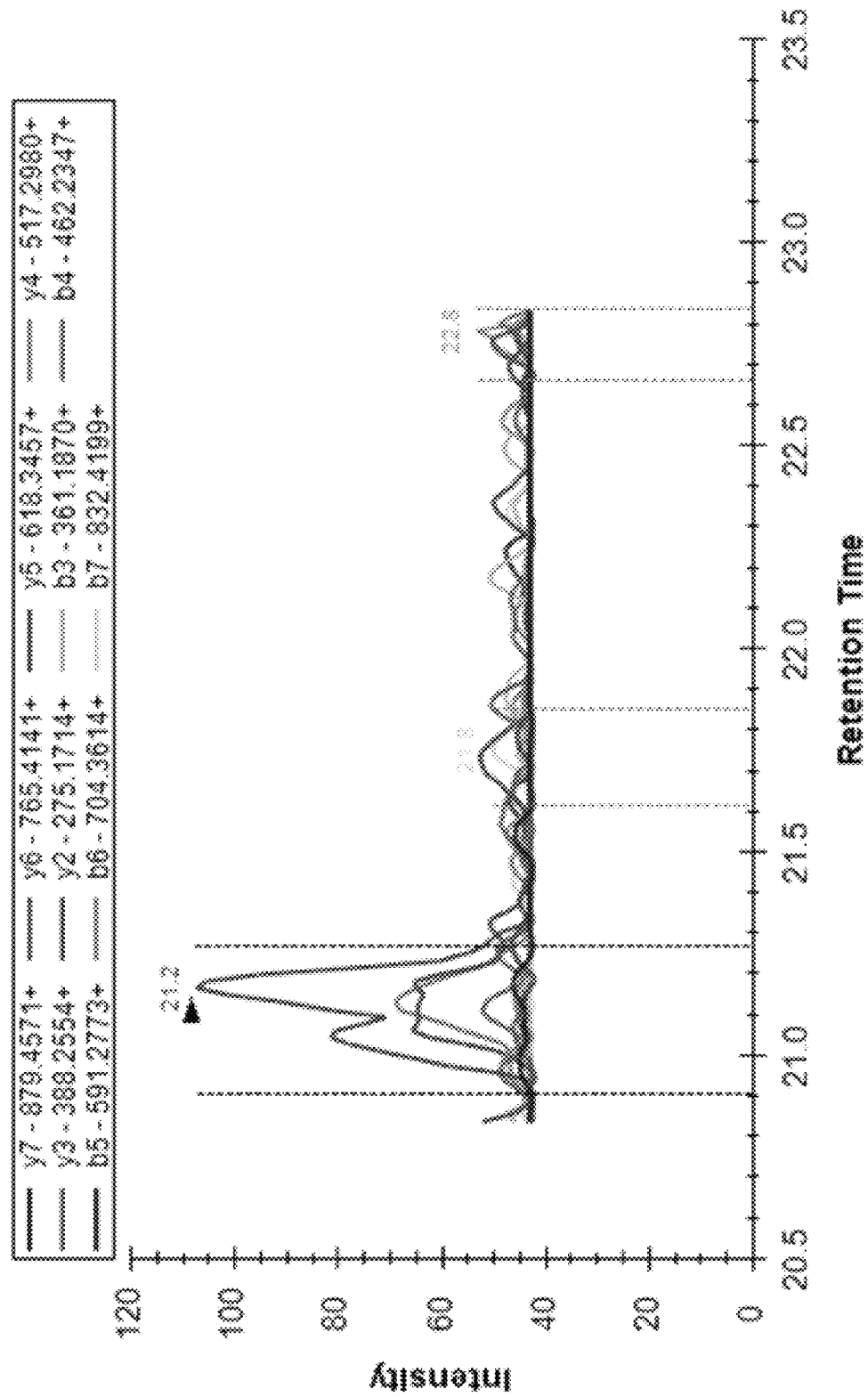
Figure 10A:
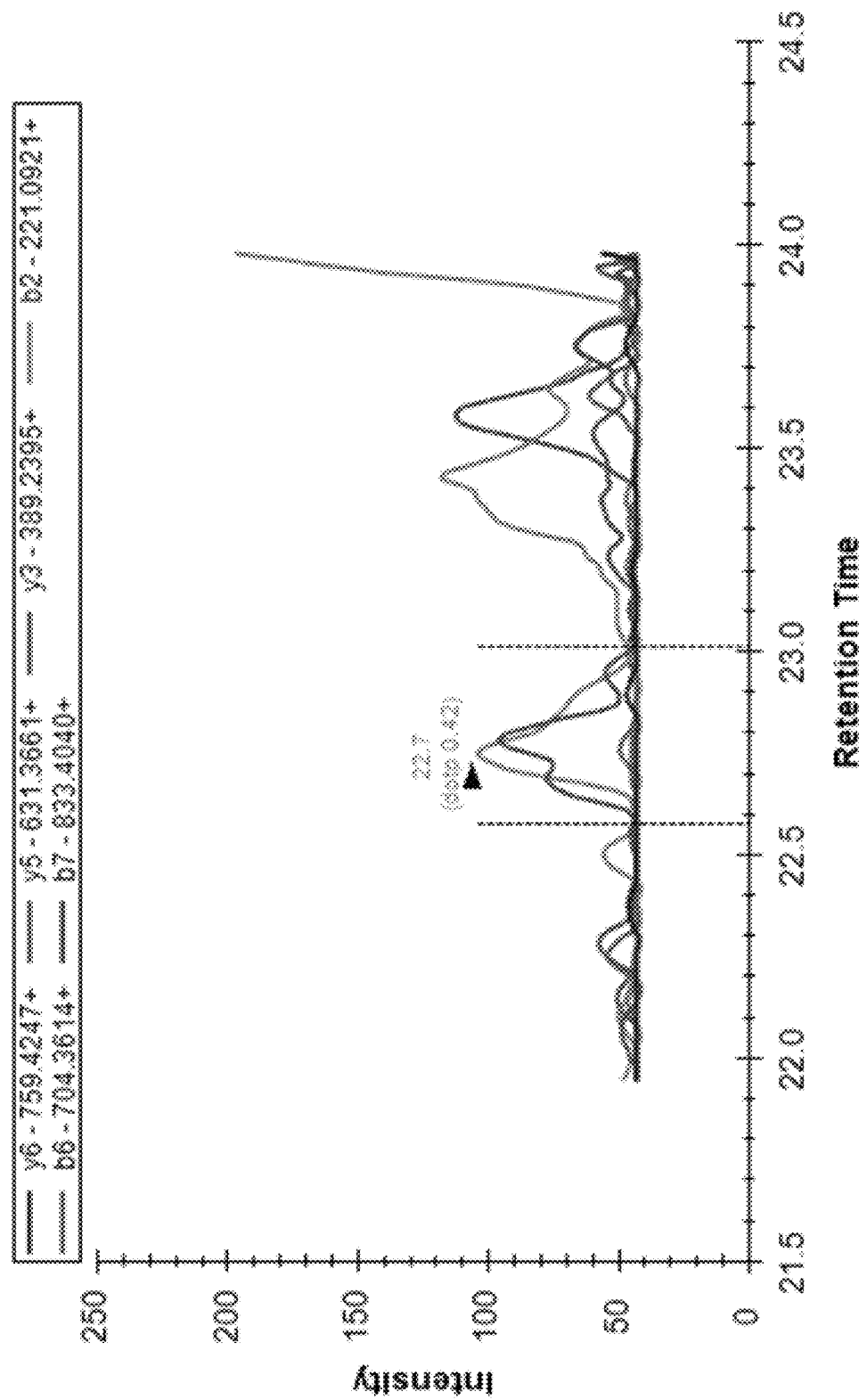
FIGS. 10a and 10b are results of MRM analysis of non-glycosylated peptide (GYQELLEK) (SEQ ID NO: 10) and de-glycosylated peptide (GYQELLEK) (SEQ ID NO: 10) of AFP, respectively using the pooled normal control sample.
Figure 10B:
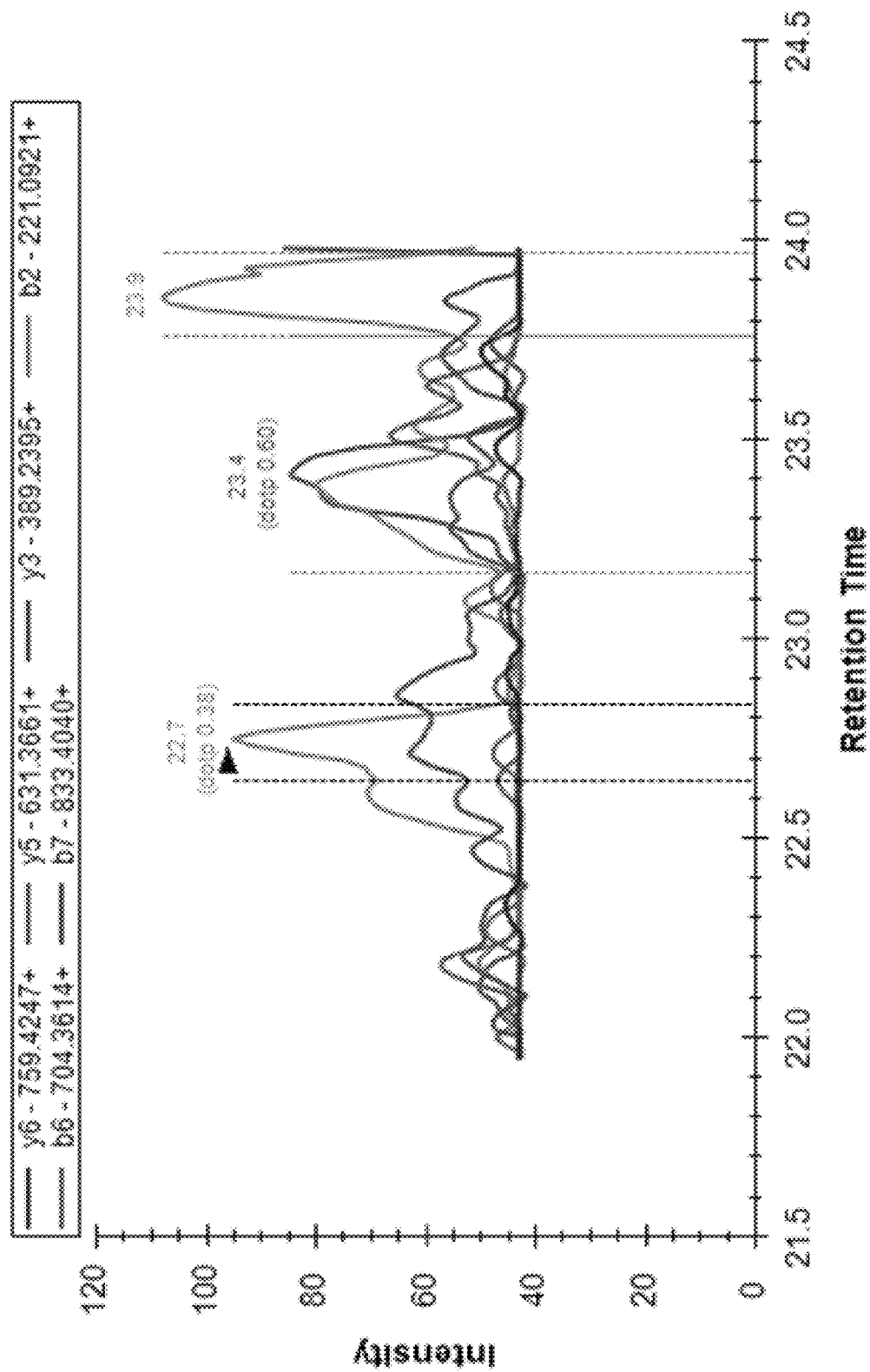
Figure 10C:
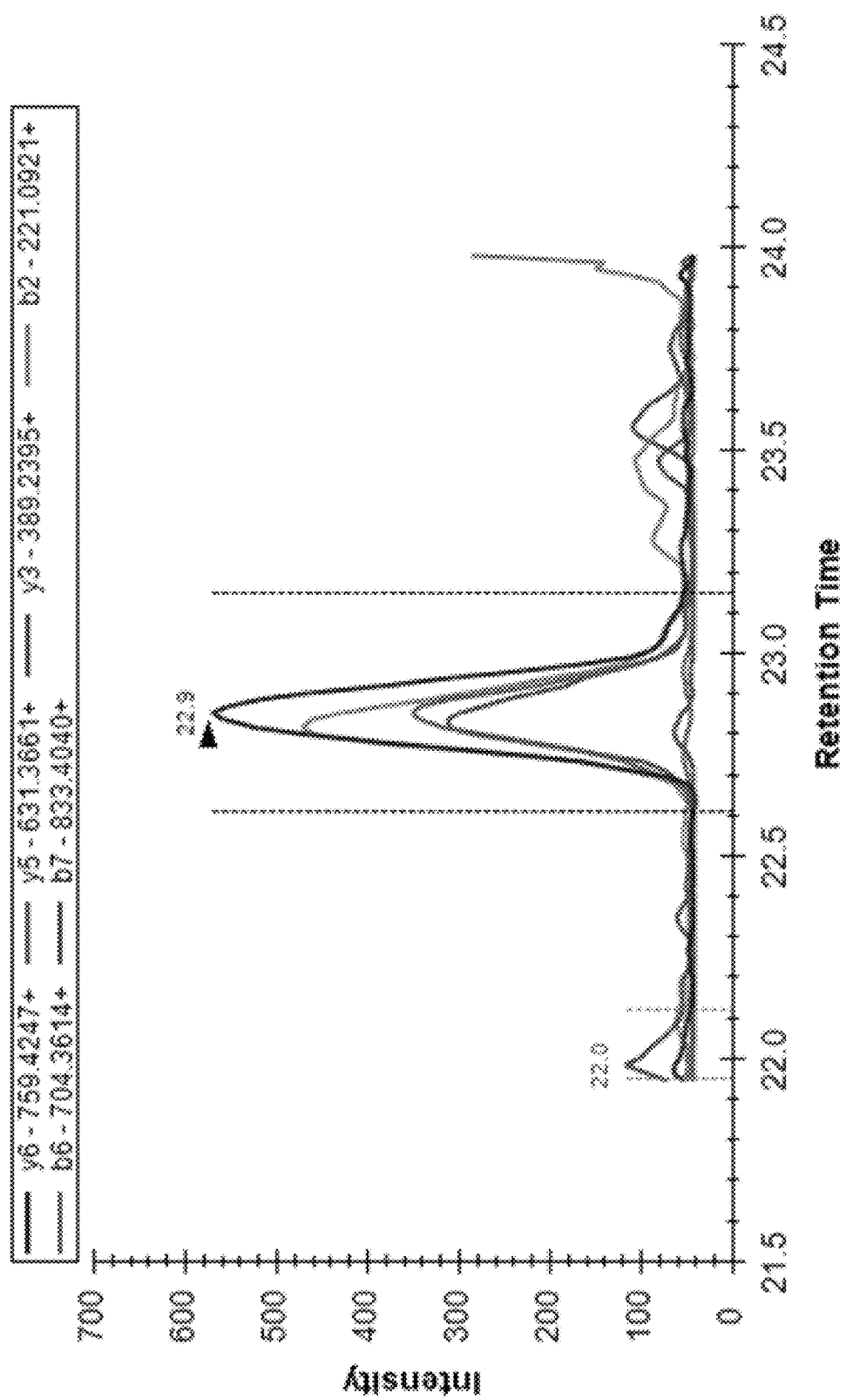
FIGS. 10c and 10d are results of MRM analysis of non-glycosylated peptide (GYQELLEK) (SEQ ID NO: 10) and de-glycosylated peptide (GYQELLEK) (SEQ ID NO: 10) of AFP, respectively using the pooled liver cancer patient sample.
Figure 10D:
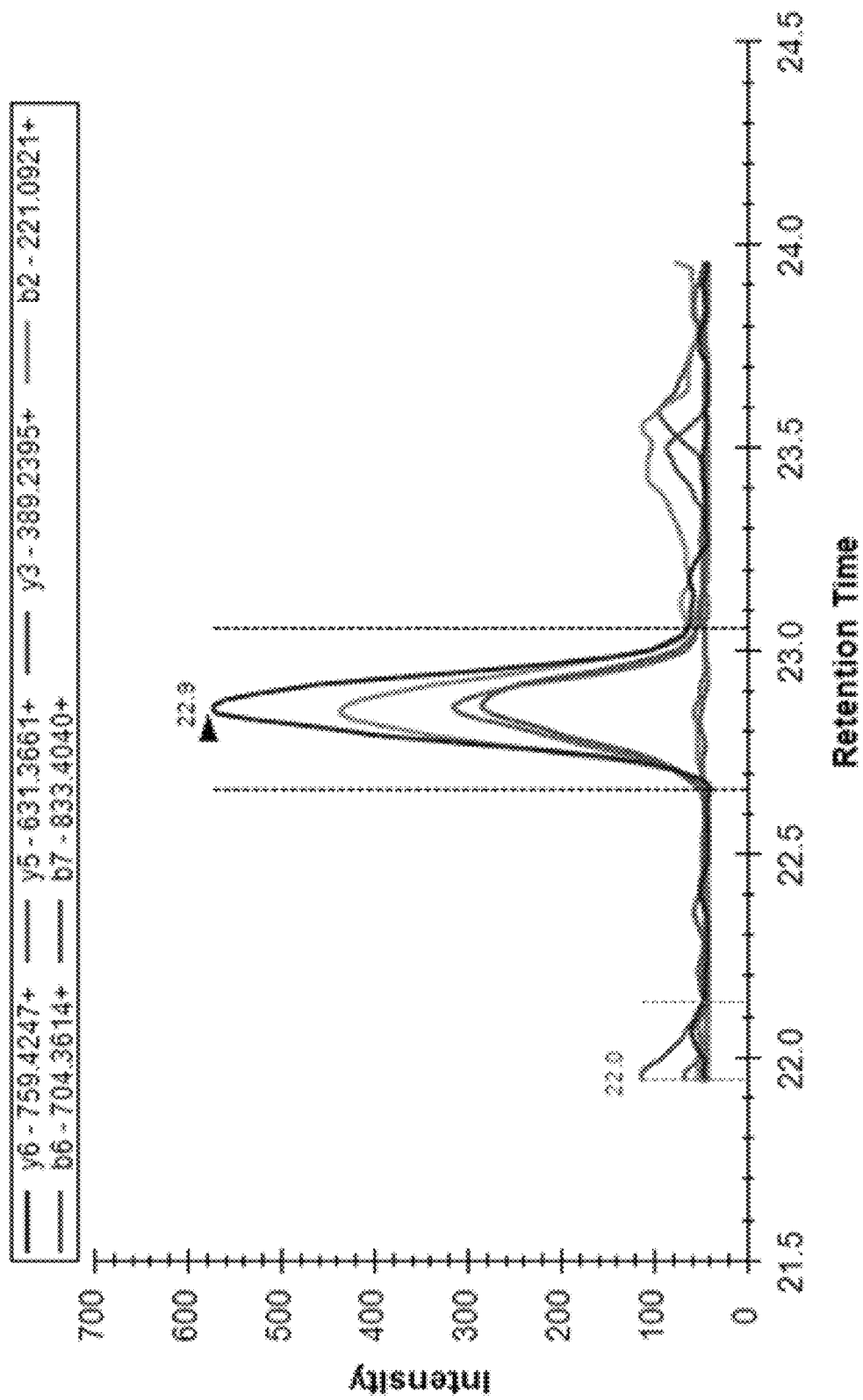

Summarizing the results of the experiments using the standard glycoprotein, the de-glycosylated peptide in D-form was detected in MRM analysis as shown in FIG. 7; however the glycosylated peptide in a native N-form was not detected because of the mass changed due to the presence of glycan. This indicates that the glycosylated peptides can be successfully used to quantify the glycoproteins in biological samples. In case of the non-glycosylated peptides, the peak intensity was found to be increased in the de-glycosylated sample treated with PNGase-F compared to the glycosylated sample. This is due to that the steric hindrance by the glycans was disappeared by PNGase-F which removes the glycan from the peptide thus facilitating the excess of trypsin to the target peptide.

Example 2. MRM Analysis of the Glycoproteins in Liver Cancer Sample

Example 2-1 Clinical Information of the Sample

The institutional review board of Seoul National University Hospital approved the protocol of the present invention, and the written informed consent was obtained from each patient or their legally authorized representative. The clinical characteristics of the patients are as in Table 7.

In the present examples, 60 normal and 60 liver cancer samples were used. The samples were selected to include more sample from men than women in consideration of the higher ratio of liver cancer found in men than women. Although liver cancers are classified into virus origin (HBV, HCV) and alcoholic origin, only the liver cancer samples of HBV origin were selected in consideration of the fact that HBV is the highest cause of liver cancer in Asia and Africa.

TABLE 7

|  | MRM analysis | |
| --- | --- | --- |
|  | HCC Group | Healthy group |
| Total patient number | 60 | 60 |
| Gender (Male/Female) | 42/18 | 41/19 |
| Age (Mean, Range) | 58 (38-76) | 53 (32-74) |
| Etiology of liver disease | HBV, 60 (100%) |  |
| Locoregional modality |  |  |
| TACE | 30 |  |
| PEIT | 22 |  |
| TACE & PEIT | 4 |  |
| RFA | 3 |  |
| Operation | 1 |  |
| APP value (Mean, Range) | 12174 (3-283000) |  |
| <20 ng/ml | 26 |  |
| 20-200 ng/ml | 11 |  |
| 200-1000 ng/ml | 11 |  |
| >1000 ng/ml | 12 |  |
| PIVKA value (Mean, Range)* | 993 (3-13641) |  |
| <40 ng/ml | 26 |  |
| 40-400 ng/ml | 13 |  |
| 400-1000 ng/ml | 5 |  |
| >1000 ng/ml | 13 |  |

*PIVKA values were provided for 58(M40F18) among a total of 60 HCC group
Abbreviations
AFP: Alpha-Fetoprotein
PIVKA: Proteins induced by vitamin K absence or antagonist
TACE: Transcatheter arterial chemoembolition
PEIT: Percutanious ethanol injection therapy
RFA: Radiofrequency ablation

Example 2-2 Selection of the Glycosylated Proteins Used in the Analysis of Clinical Samples In case of alpha-fetoprotein (AFP) known as a biomarker for liver cancer, the peptide sequence in which the NxS/T motif is glycosylated is VNFTEIQ (SEQ ID NO: 9). The glycosylated peptide comprising NxS/T motif and the non-glycosylated peptide without the motif were analyzed using Skyline program to determine the possible transition (refer to Example 2-3). The sequence of the full-length is shown in FIG. 8, in which the green indicates the sequence used in the analysis.

To further discover the potential glycosylated protein markers specific for liver cancer, 495 glycosylated proteins which contain NxS/T motif(s) and are known to be N-glycosylated at the motif were selected from Plasma Proteome Database (PPD). The transition was determined using Skyline program for the peptides containing the motif and being glycosylated and for the non-glycosylated peptide without the motif. Through this process, a total of 406 proteins, 1637 peptides, and 9821 transitions (Q1/Q3) were selected for the non-glycosylated peptides. For the glycosylated peptides, a total of 240 proteins, 363 peptides, and 4111 transitions (Q1/Q3) were selected.

Example 2-3 Determination of Theoretical Transition (Q1/Q3) of the Glycosylated Proteins Including AFP from Liver Cancer As described in Example 1 for the analysis of standard protein, AFP protein in a native form and conversion form in which N is substituted with D was imported into Skyline program to determine the theoretical transition (in silico prediction). As a result, Q1 and Q3 differences between the two types of peptides were found to be 0.49 Da and 0.98 Da, respectively. Results are shown in Table 8. Other proteins in Example 2-2 from liver cancer were analyzed in the same way.

TABLE 8

| | | | Native sequence | |
| --- | --- | --- | --- | --- |
| Peptide sequence | Isotype | Ion name | Precursor Ion (Q1) | Product Ion (Q3) |
| VNFTEIQK | light | y7 | 489.766374 | 879.457058 |
| (SEQ ID | light | y6 | 489.766374 | 765.414131 |
| NO: 9) | light | y5 | 489.766374 | 618.345717 |
|  | light | y4 | 489.766374 | 517.298038 |
|  | light | y2 | 489.766374 | 275.171381 |
| GYQELLEK | light | y6 | 490.258382 | 759.424696 |
| (SEQ ID | light | y5 | 490.258382 | 631.366118 |
| NO: 10) | light | y3 | 490.258382 | 389.239461 |
|  | light | b2 | 490.258382 | 221.092068 |
|  | light | b6 | 490.258382 | 704.361367 |
| VDFTEIQK | light | y7 | 490.258382 | 880.441074 |
| (SEQ ID | light | y6 | 490.258382 | 765.414131 |
| NO: 9) | light | y5 | 490.258382 | 618.345717 |
|  | light | y4 | 490.258382 | 517.298038 |
|  | light | y2 | 490.258382 | 275.171381 |
| GYQELLEK | light | y6 | 490.258382 | 759.424696 |
| (SEQ ID | light | y5 | 490.258382 | 631.366118 |
| NO: 10) | light | y3 | 490.258382 | 389.239461 |
|  | light | b2 | 490.258382 | 221.092068 |
|  | light | b6 | 490.258382 | 704.361367 |

Example 2-4 Preparation of Pooled Clinical Samples and MRM Analysis

Each of sixty normal control and HCC patient samples were pooled into three groups by twenty samples. Major six proteins in serum (albumin, 1 gG, 1 gA, transferrin, haptoglobin, alpha-1-antitrypsin) were removed using MARS (Part #5185-5984, multiple affinity removal system, Agilent Technologies, USA) according to the manufacturer's instruction.

Then the serum proteins were concentrated using a filter (3K Amicon, USA) and quantified using BCA (bicinchoninic acid (BCA) assay, Sigma-Aldrich, USA) kit according to the manufacturer's instruction. Then 100 μg of the protein was treated either with water (control) or PNGase-F followed by treatment with trypsin to de-glycosylate the protein.

For quality control of the data obtained and the stability confirmation of the instrument, peptides in which C and N atoms of arginines are heavy labelled were used as an internal standard. The peptide sequence used is LNVENPK from E. coli and thus not present in human serum, which was used at the concentration of 5 fmol per analysis.

Experiments were repeated 3 times per group and then the data obtained were imported into Skyline and converted into the transition area for each peptide. Then the peak area obtained from the AFP target peptide were normalized by the peak area obtained from the heavy labelled internal standard.

Example 2-5 Results of MRM Analysis of Pooled Clinical Samples

2-5-1 AFP Peptide (GYQELLEK (SEQ ID NO: 10)/VDFTEIQK (SEQ ID NO: 9)) and Results of Analysis for Discovering Potential Liver Specific Glycosylated Protein Markers Results from the experiments in which the control glycosylated sample treated only with water (control) and the de-glycosylated sample treated with PNGase-F were analyzed for VNFTEIQK (VDFTEIQK (SEQ ID NO: 9)) peptides are shown in FIGS. 9a to 9d. In the pooled normal control samples, both N-form VNFTEIQK (VDFTEIQK (SEQ ID NO: 9)) used for the glycosylated samples and D-form VDFTEIQK (SEQ ID NO: 9) used for the de-glycosylated samples were not detected.

In contrast, with HCC samples, when N-form VNFTEIQK (VDFTEIQK (SEQ ID NO: 9)) was used for the glycosylated samples and D-form VDFTEIQK (SEQ ID NO: 9) was used for the de-glycosylated samples, the de-glycosylated samples analyzed for D-form were only detected.

This is due to the fact that the expression level of AFP is increased in HCC samples compared to the control and thus comes within the level to be detected by Mass spectrometry in contrast to the glycosylated samples in which case the mass of the peptide is changed due to the glycosylation and thus the peptide is not detected and only the de-glycosylated samples are detected.

Results from the experiments in which the control glycosylated sample treated only with water (control) and the de-glycosylated sample treated with PNGase-F were analyzed for the non-glycosylated GYQELLEK (SEQ ID NO: 10) peptide are shown in FIGS. 10a to 10d. When the glycosylated and de-glycosylated samples were analyzed in the pooled normal control sample, none were detected. When the glycosylated and de-glycosylated samples were analyzed in the pooled HCC sample, both were detected. That is, the level of AFP protein was increased in HCC samples compared to the normal sample and thus comes within the level to be detected by Mass spectrometry.

Figure 11:
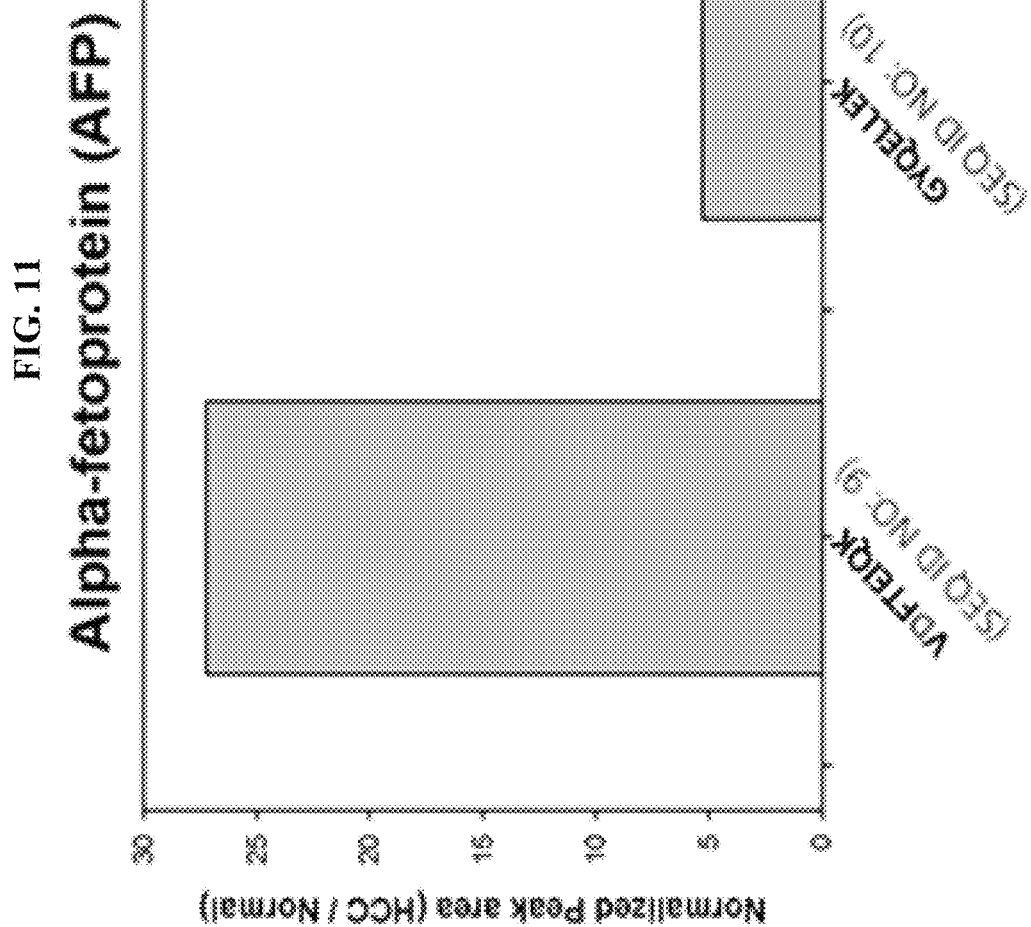
FIG. 11 is a graph showing the difference in the peak area between the normal sample and liver cancer sample obtained from MRM analysis for AFP target peptides.

In summary, when the serum from the pooled normal control sample and HCC sample were treated with PNGase-F/trypsin and the de-glycosylated samples were analyzed for the de-glycosylated peptide VDFTEIQK (SEQ ID NO: 9) and the non-glycosylated peptide GYQELLEK (SEQ ID NO: 10), a 27.3 fold difference was found between HCC group and the normal group when analyzed for VDFTEIQK (SEQ ID NO: 9) in comparison to a 5.3 fold difference when analyzed for GYQELLEK (SEQ ID NO: 10) as shown in Tables 9 and 10, and FIG. 11. This indicates that the glycosylation analysis is far superior in detecting the difference to the protein expression analysis.

TABLE 9

| Set | Normal group | | | Cancer group | | |
|---|---|---|---|---|---|---|
| | Average | STDEV | CV (%) | Average | STDEV | CV (%) |
| 1 | 0.0011 | 0.0004 | 38.5054 | 0.0731 | 0.0054 | 7.3393 |
| 2 | 0.0030 | 0.0012 | 40.6544 | 0.0124 | 0.0011 | 8.9907 |
| 3 | 0.0015 | 0.0015 | 104.7847 | 0.0652 | 0.0076 | 11.7206 |

TABLE 10

| Set | Normal group | | | Cancer group | | |
|---|---|---|---|---|---|---|
| | Average | STDEV | CV (%) | Average | STDEV | CV (%) |
| 1 | 0.0158 | 0.0035 | 22.3136 | 0.1020 | 0.0051 | 5.0402 |
| 2 | 0.0129 | 0.0065 | 50.2251 | 0.0077 | 0.0034 | 44.6222 |
| 3 | 0.0093 | 0.0031 | 32.9208 | 0.0907 | 0.0037 | 4.0869 |

In addition to AFP, further analysis have been done to further discover the candidates of glycosylated protein markers, as a result, a total of 354 proteins and 1000 peptides therefrom were detected in the liver cancer in comparison to the normal sample. From them, 145 proteins as glycoproteins with NxS/T motif, and 182 peptides therefrom as the de-glycosylated peptide after being treated with PNGase-F were determined. The de-glycosylated peptides and glycosylated peptides used for the detection are listed in Table 16.

Example 3. MRM Analysis of an Individual Sample

Example 3-1 Preparation of Individual Clinical Sample and MRM Analysis

The preparation and MRM analysis of the individual samples from 60 normal samples and 60 HCC samples were prepared as described in Example 2.

For normalization, the synthetic heavy labelled peptide for the de-glycosylated peptide and the non-glycosylated peptide were used at the concentration of 7.3 fmol and 10.3 fmol, respectively.

All the individual samples were analyzed once and the data were imported into Skyline and converted into the area of the peptide transition. The peak area to AFP target peptide was normalized to the peak area value of the corresponding heavy labelled synthetic peptide.

In addition to AFP, the peptides or proteins which have shown at least 3 times signal to noise (S/N) ratio in the pooled clinical sample and which have been confirmed to flow in at least 3 product ions at the same retention time.

Example 3-2 AFP Target Peptide and Optimization of Collision Energy

The present Example was performed to optimize the collision energy to improve the degree of detection.

As a result of selecting the transition (Q1/Q3) of the target peptide, the difference between the endogenous peptide and the heavy labelled peptide difference was found to be 4.00 Da (5.00 Da) for Q1 and 8.01 Da (10.01 Da) for Q3.

Figure 12A:
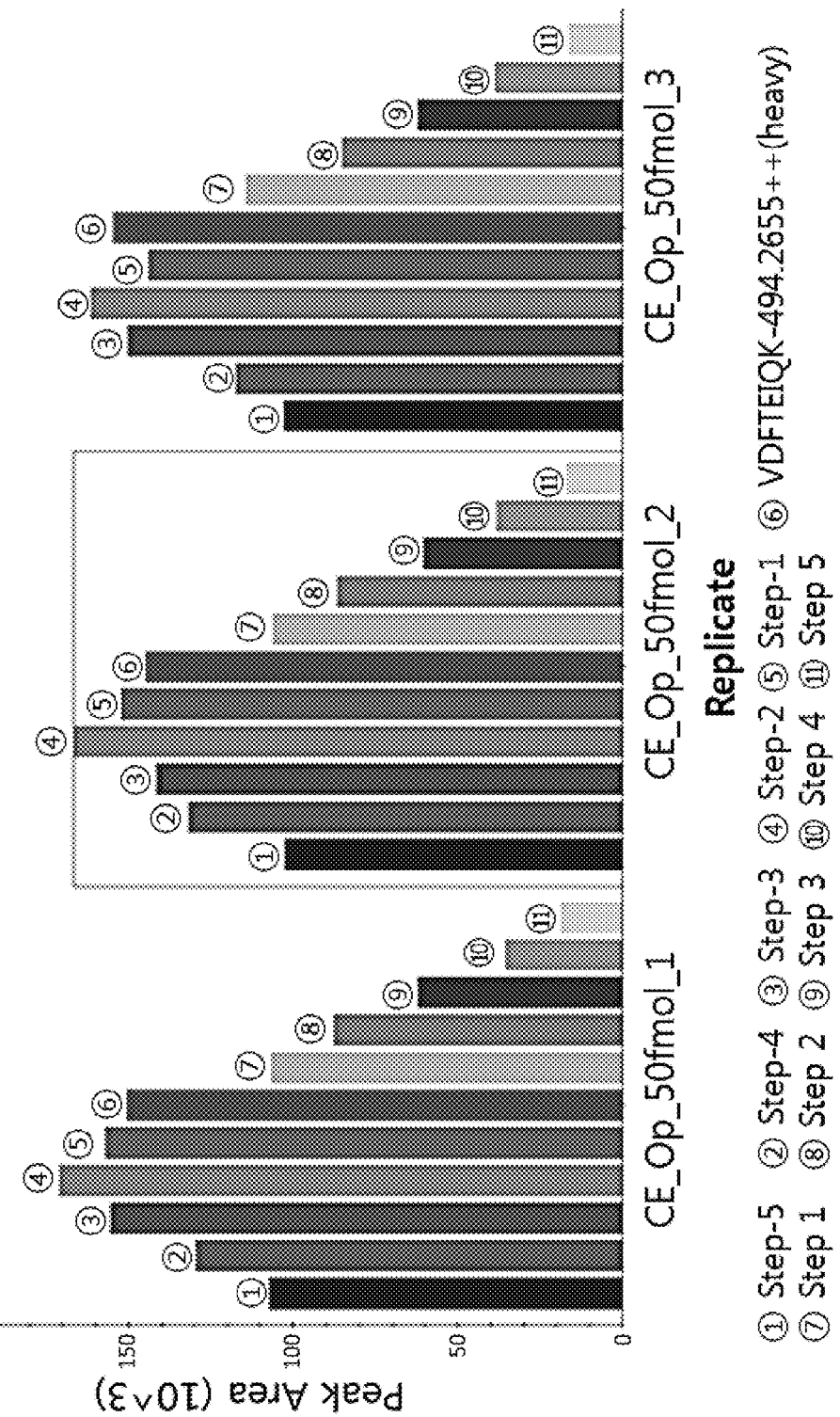
FIG. 12 is a CE optimization result for AFP target peptide using MRM analysis.
Figure 13A:
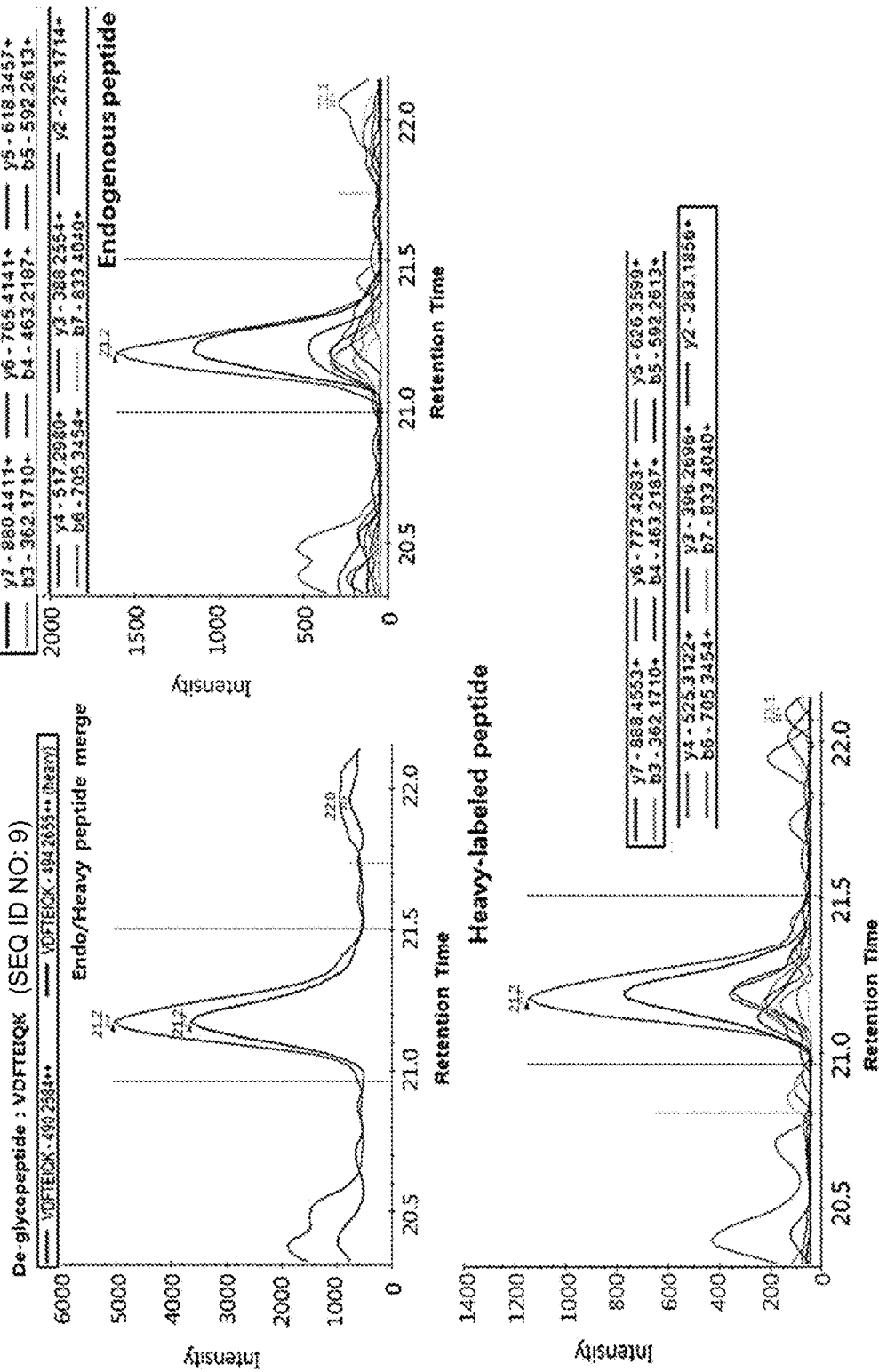
FIG. 13a is a result of MRM analysis of the endogenous AFP de-glycosylated target peptide (SEQ ID NO: 9).
Figure 13B:
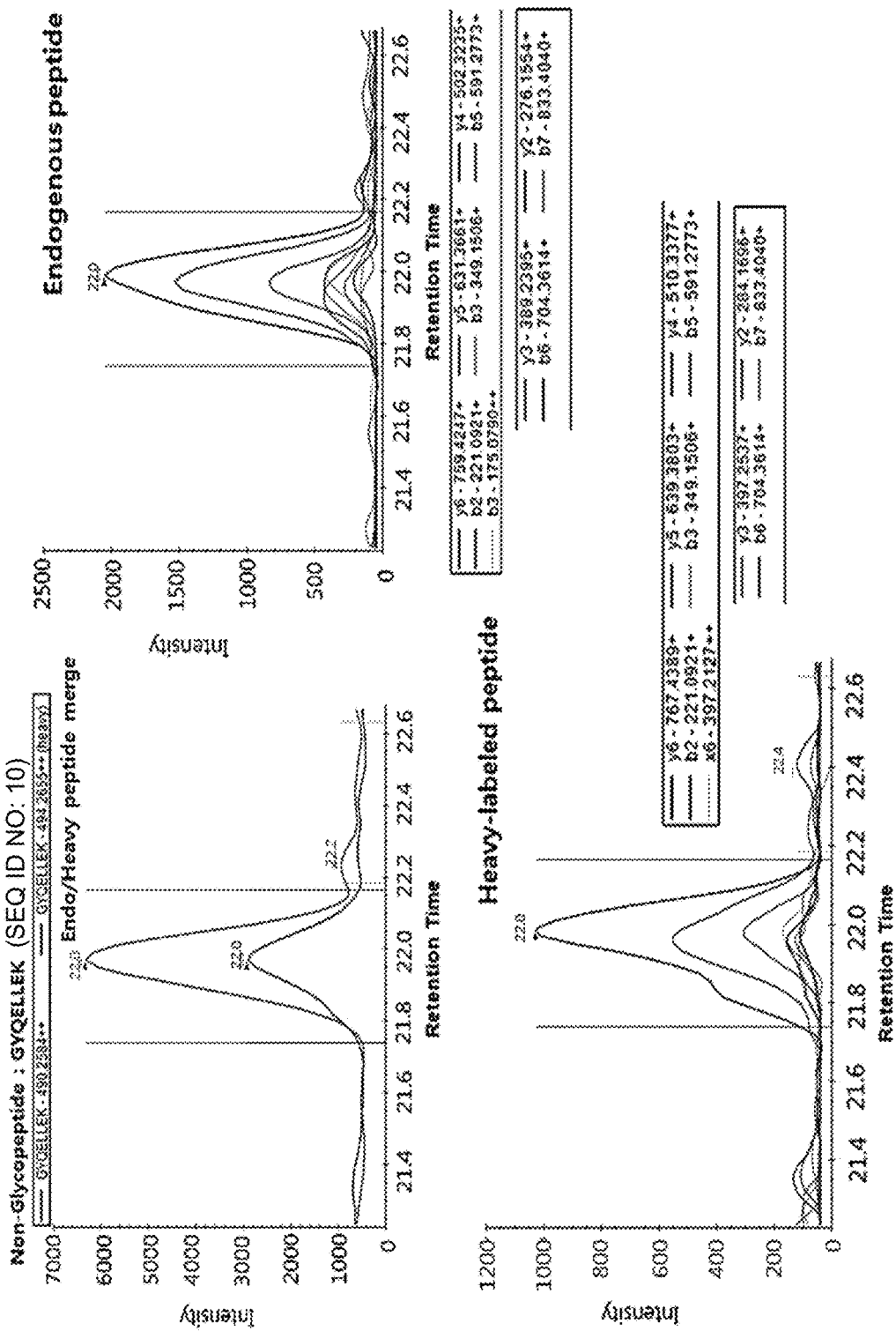
FIG. 13b is a result of MRM analysis of the endogenous AFP non-glycosylated target peptide (GYQELLEK) (SEQ ID NO: 10).
Figure 16:
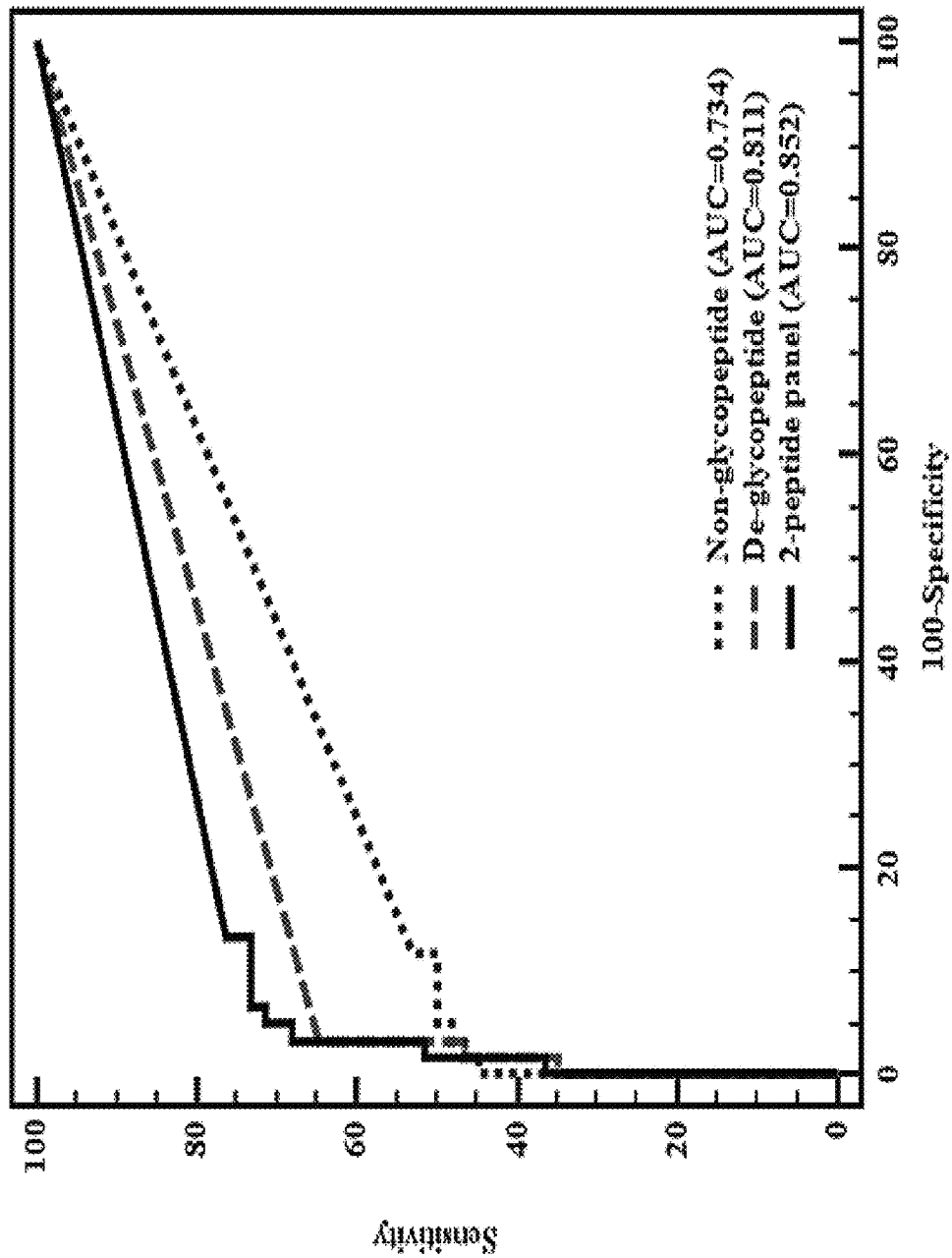
FIG. 16 is a result comparing AUC values of AFP target peptide and 2-peptides (de-glycosylated and non-glycosylated peptides) panel.
Figure 17B:
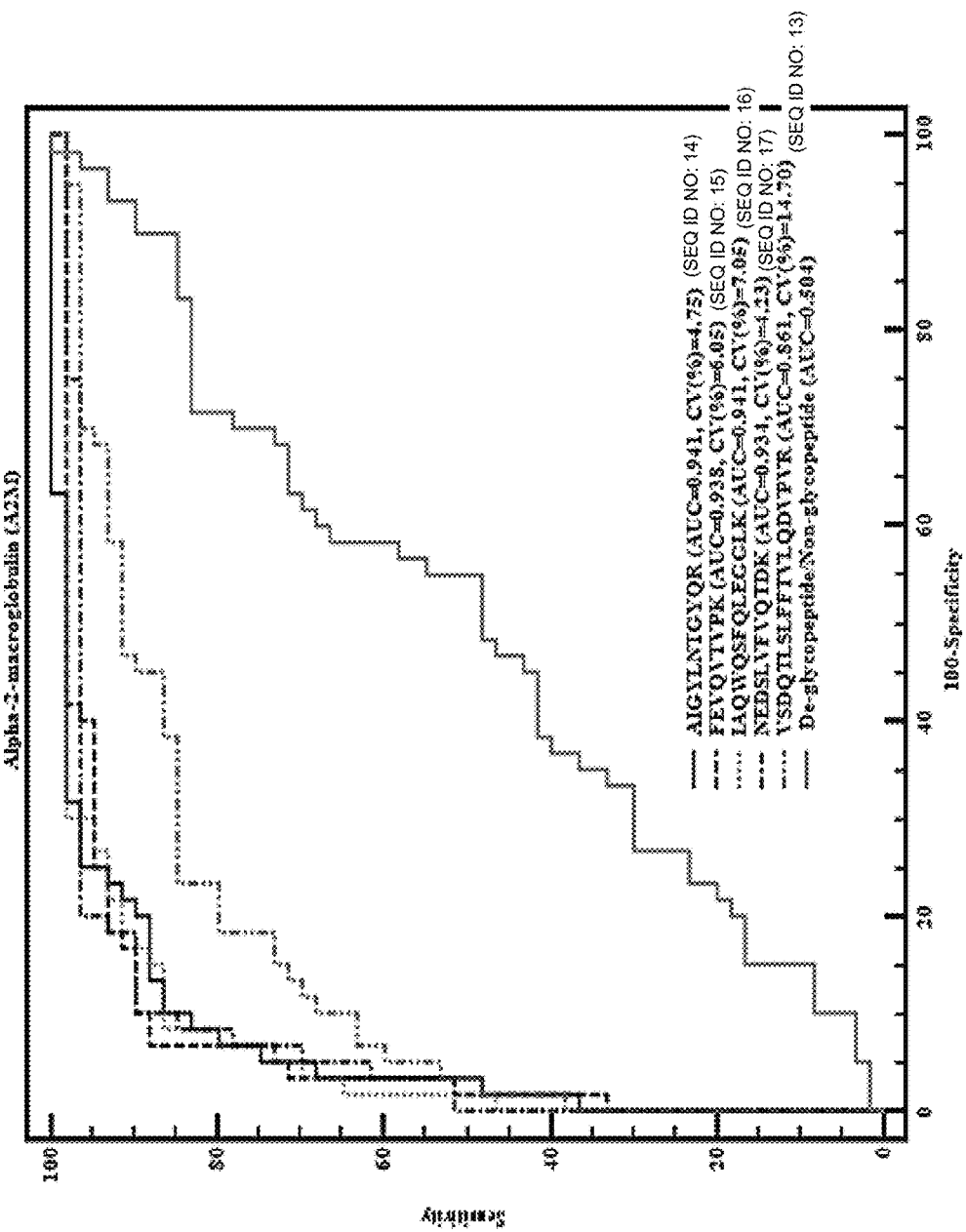
FIGS. 17a to 17z are results showing AUC values of standardized de-glycosylated peptide and standardized non-glycosylated peptide and the ratio thereof of various selected proteins to discover the potential glycosylated markers.
Figure 17D:
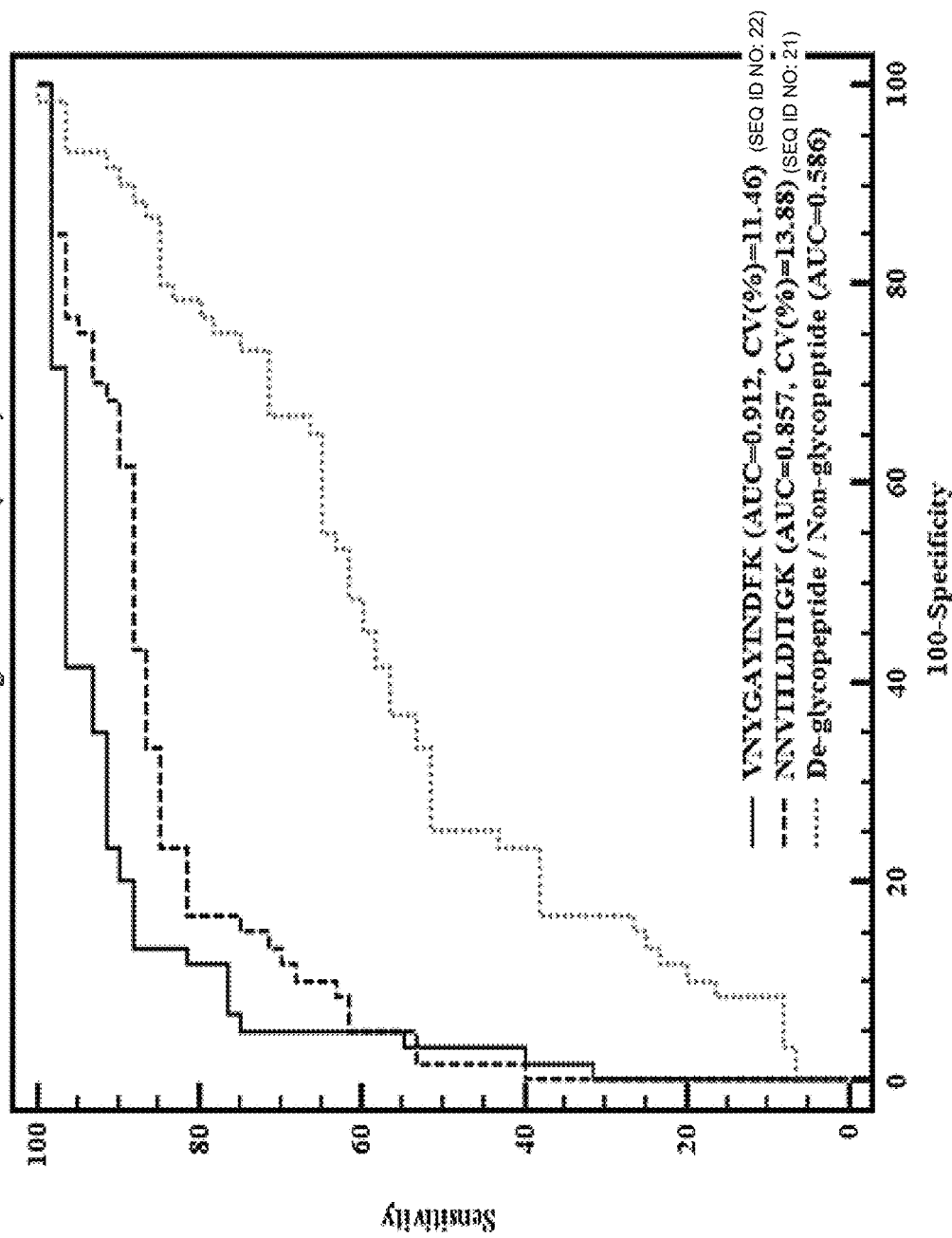
Figure 17E:
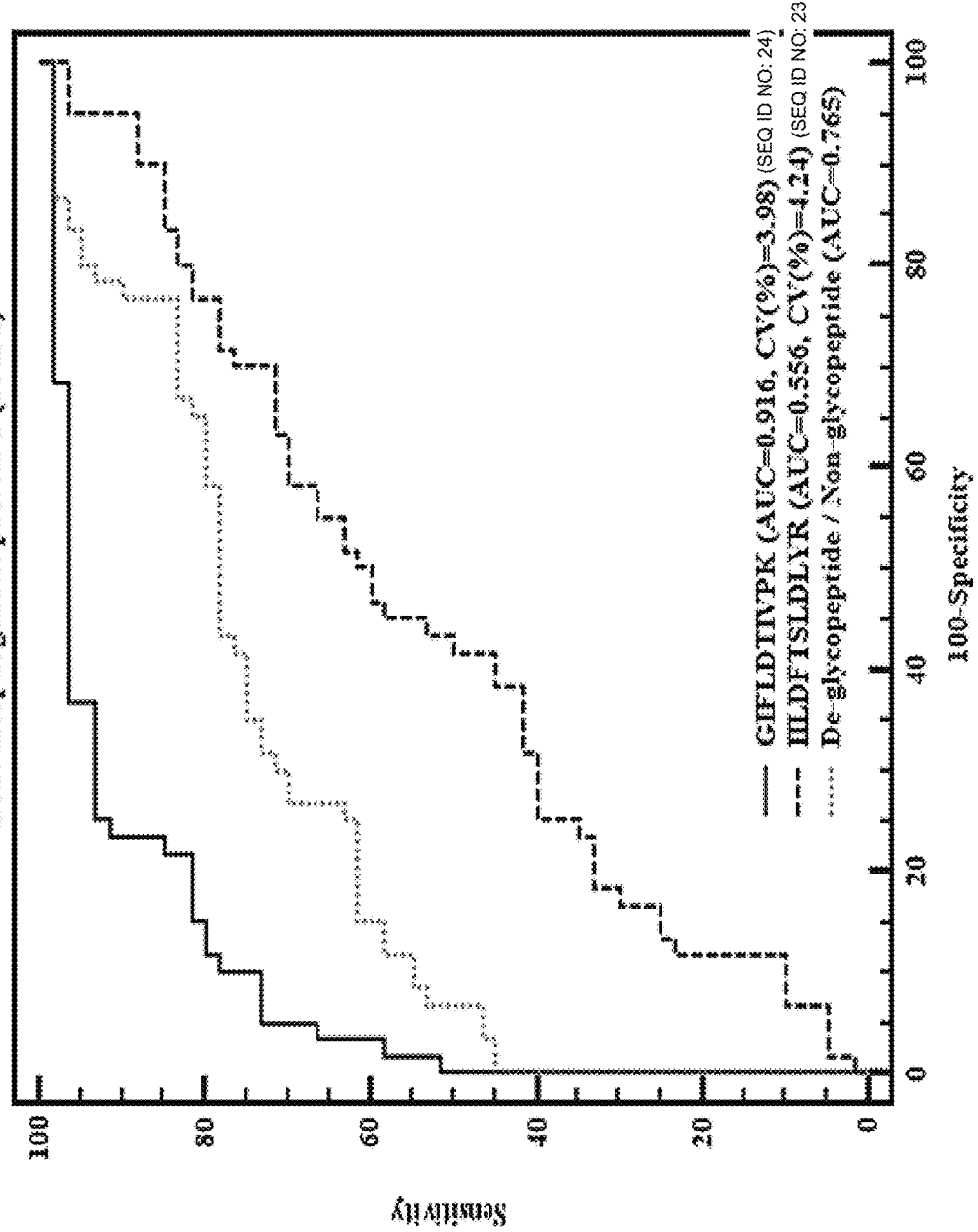
Figure 17G:
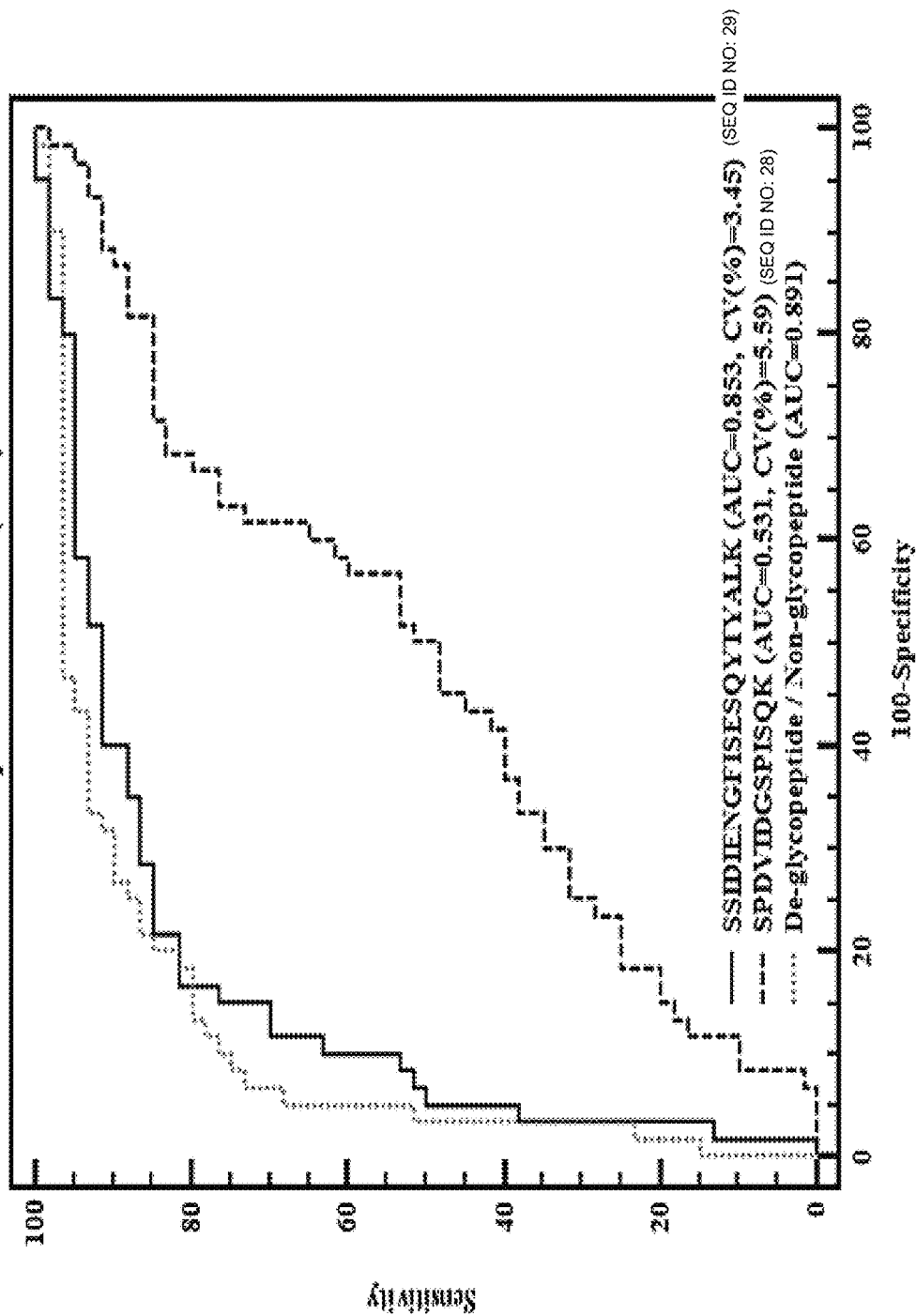
Figure 17H:
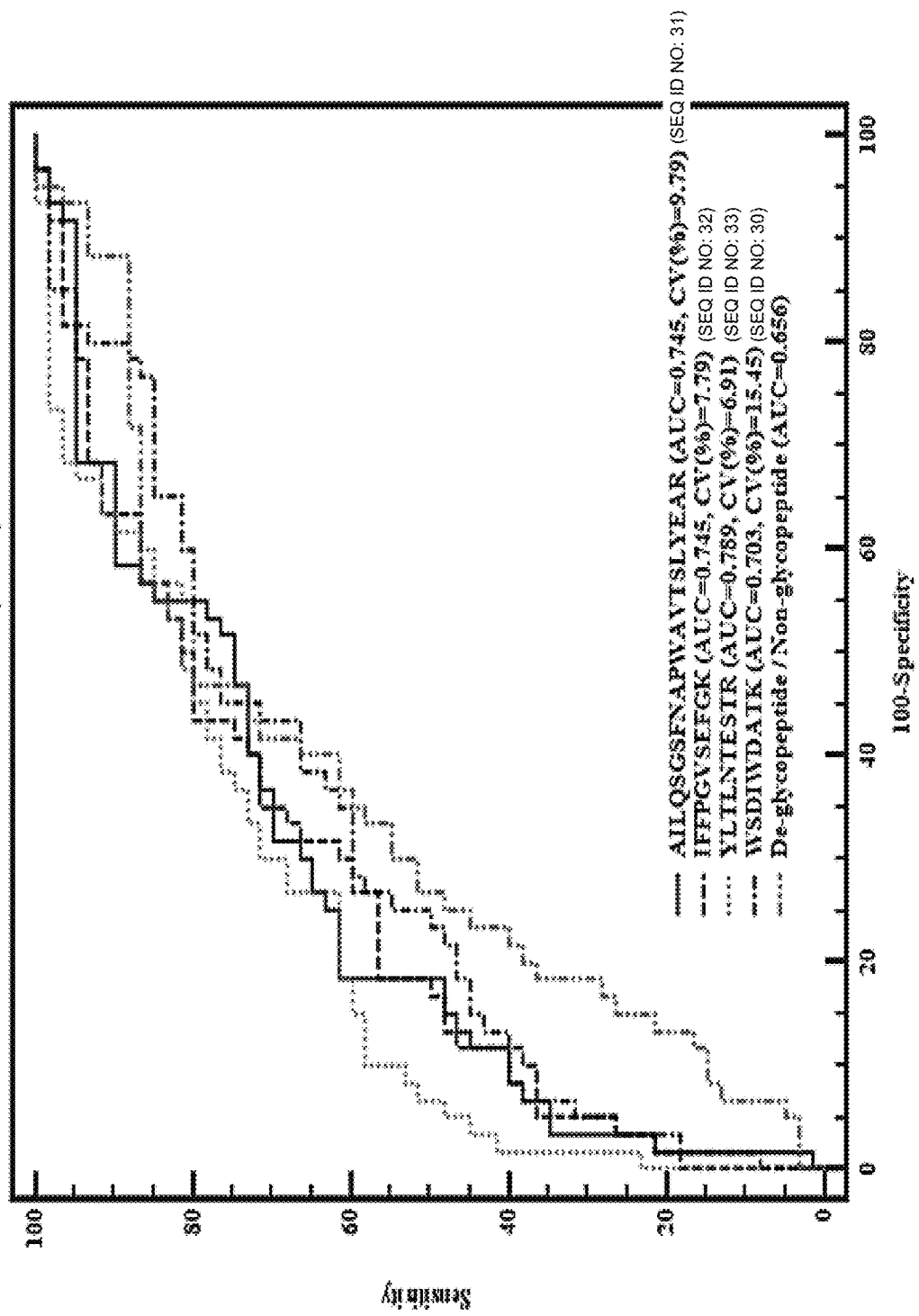
Figure 17I:
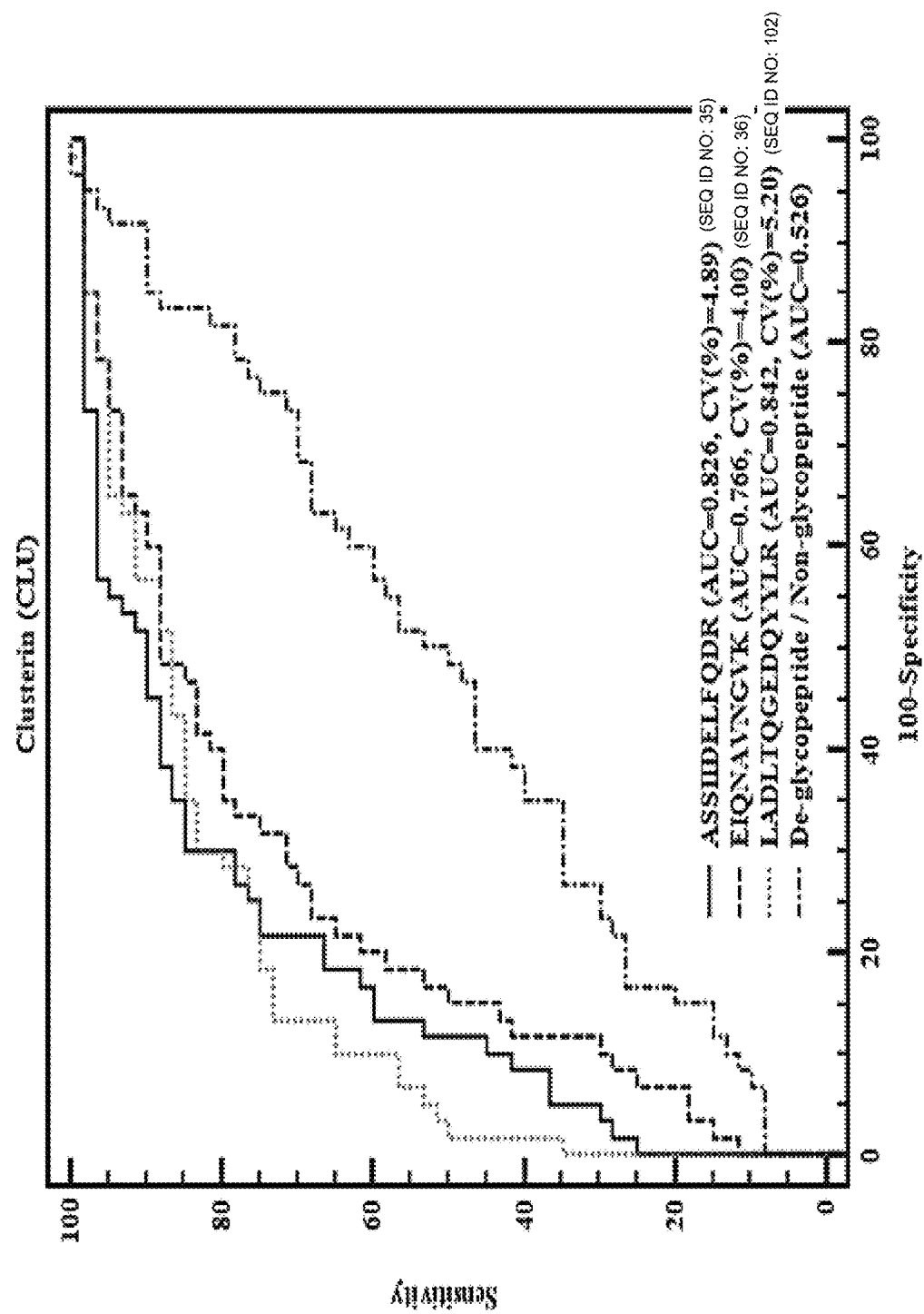
Figure 17J:
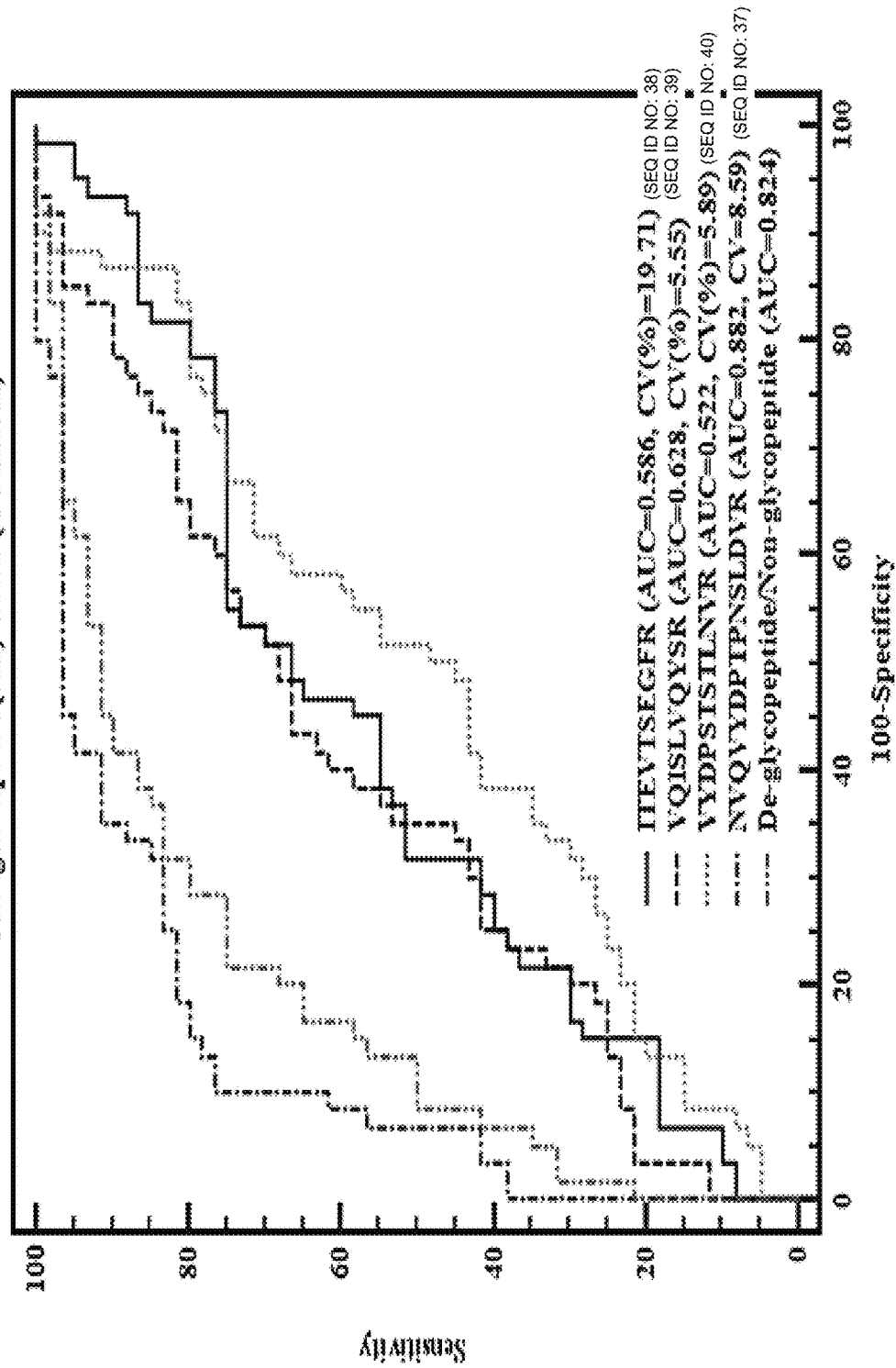
Figure 17M:
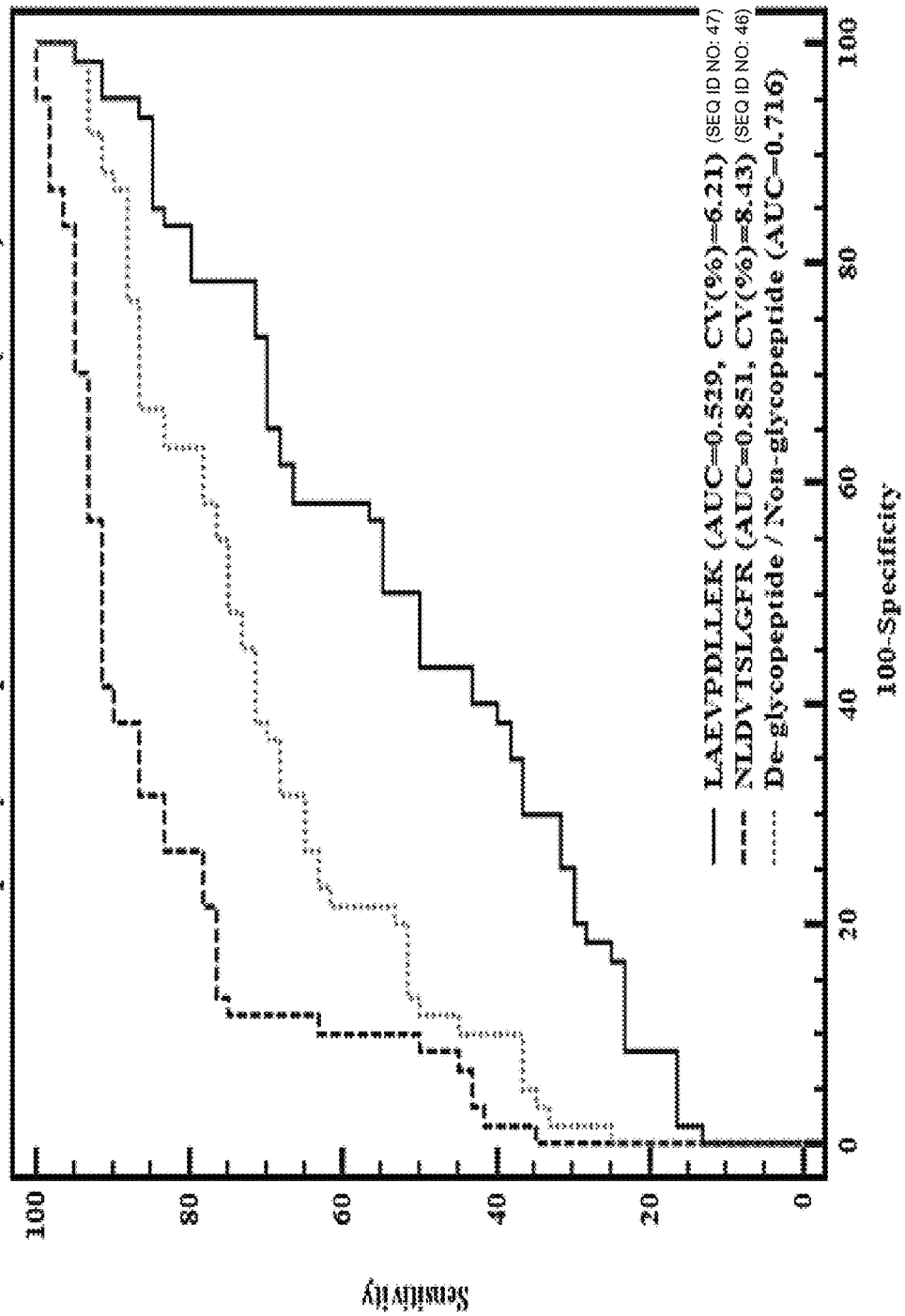
Figure 17N:
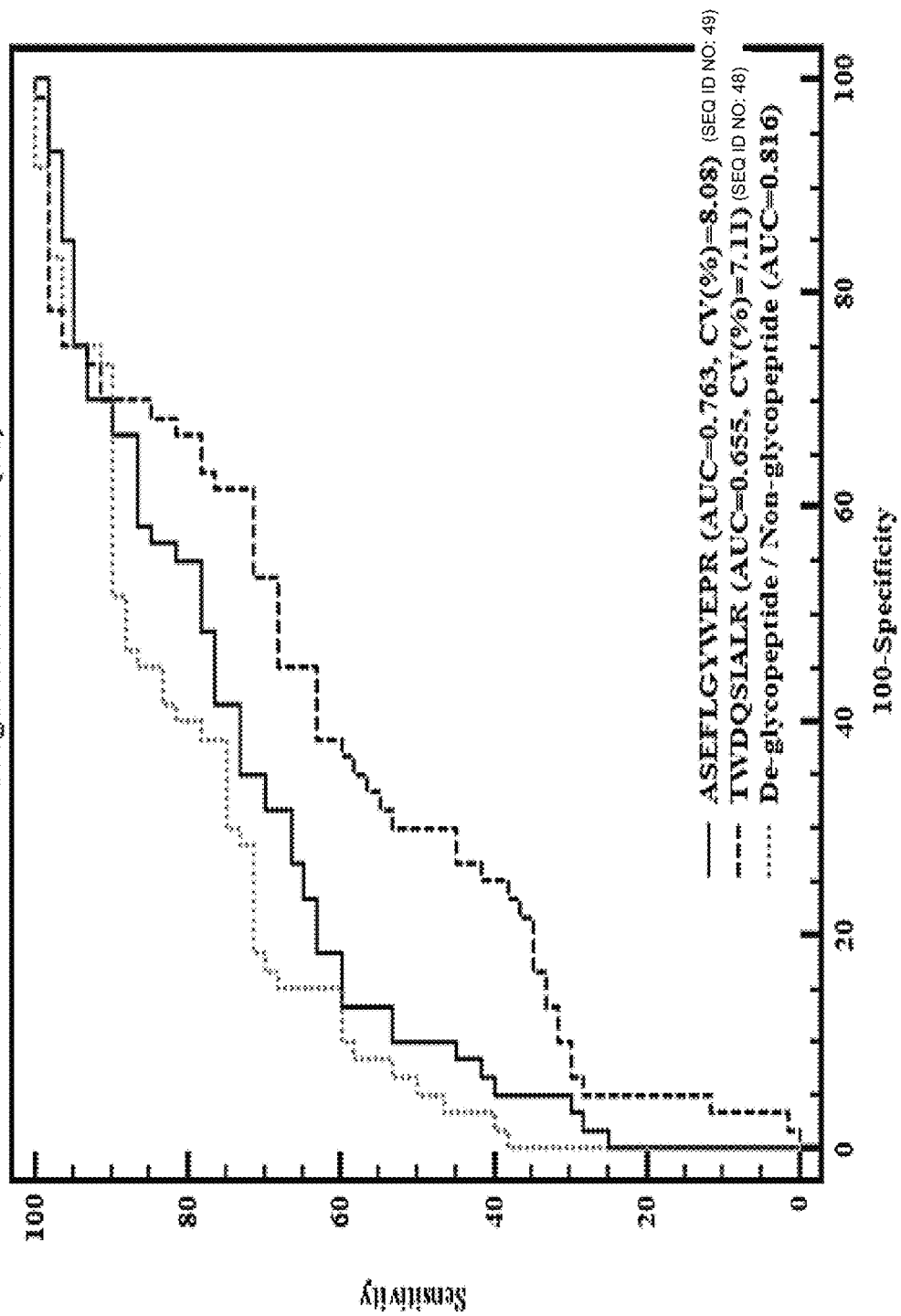
Figure 17O:
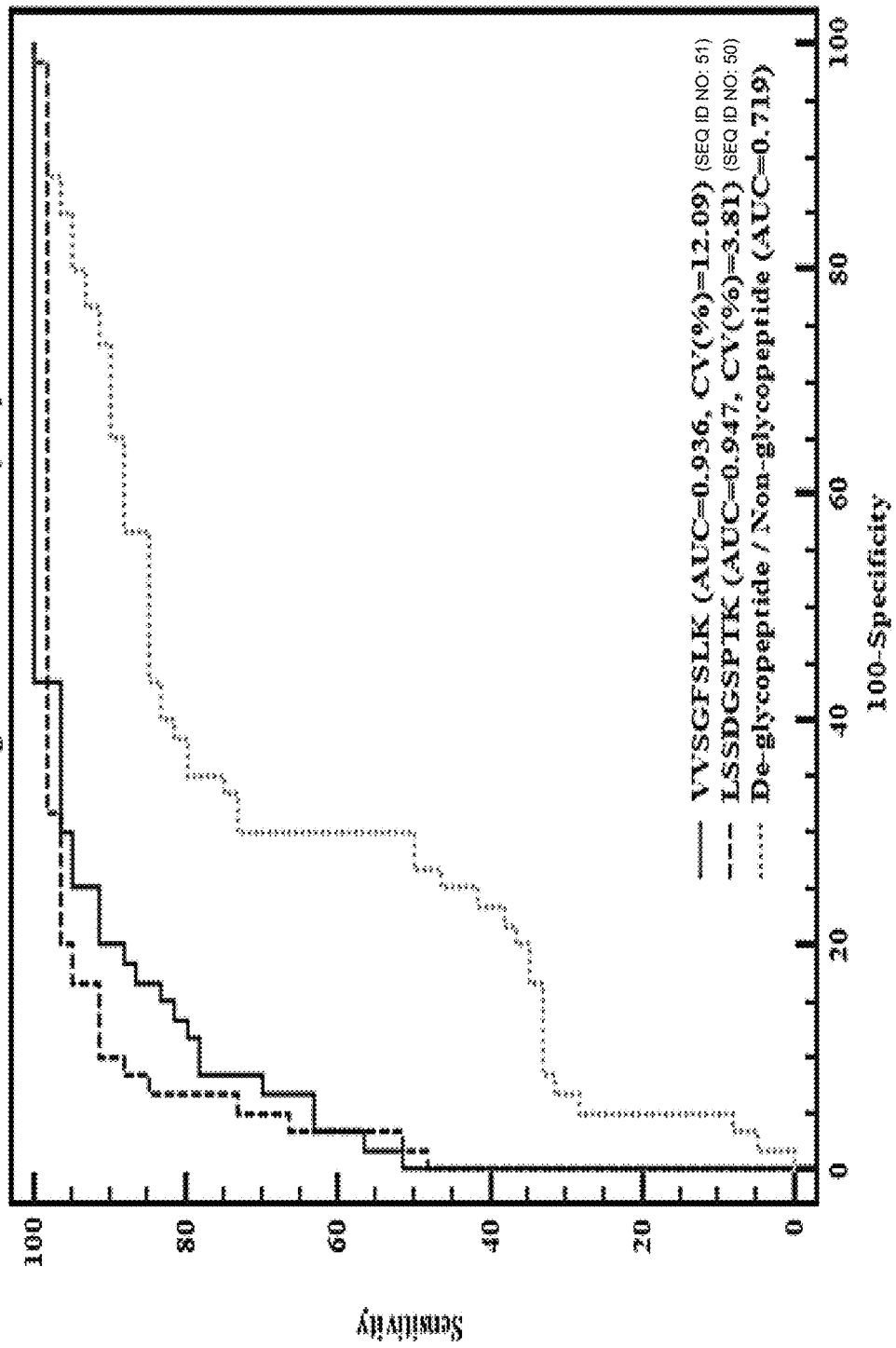
Figure 17P:
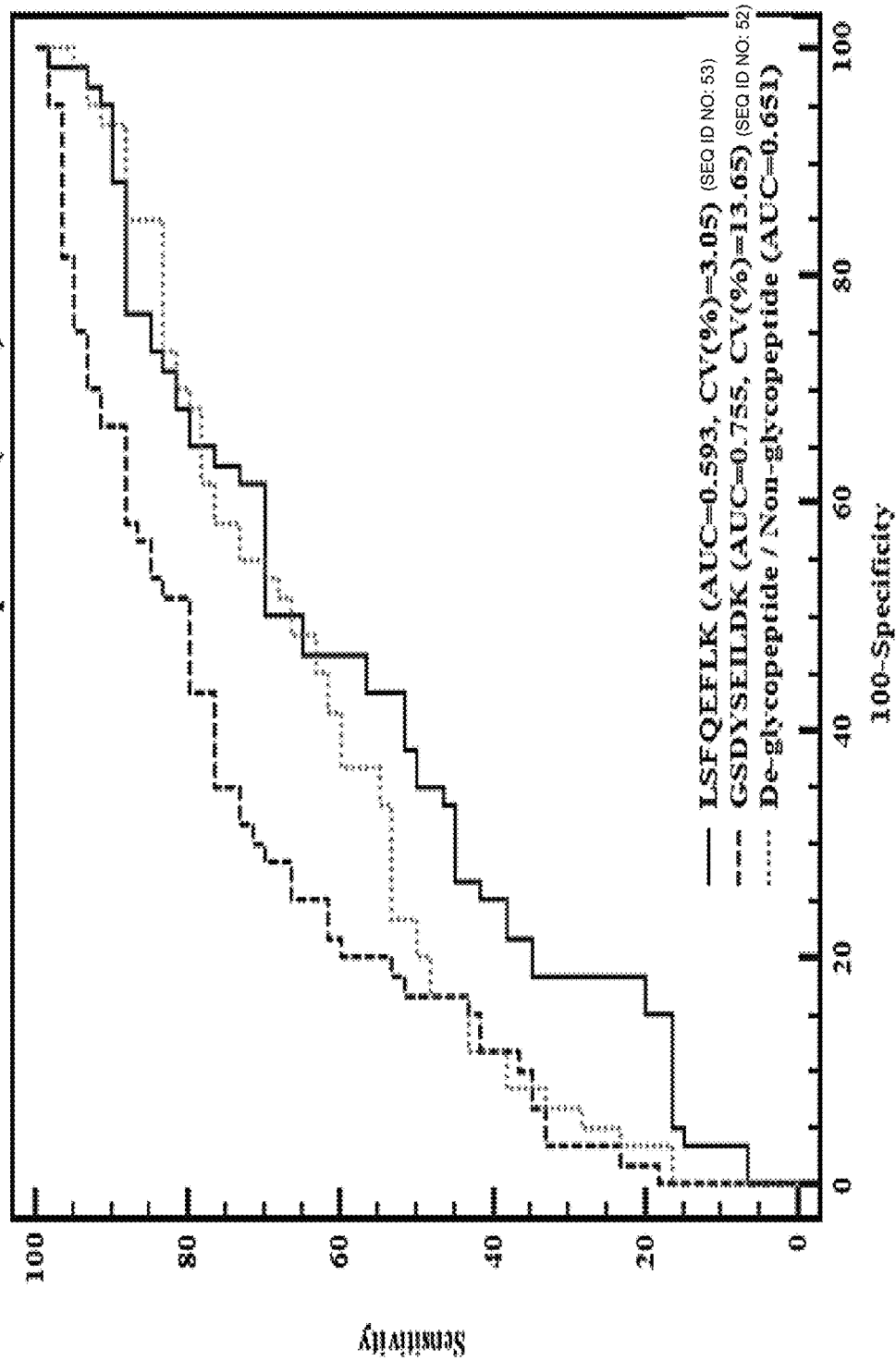
Figure 17R:
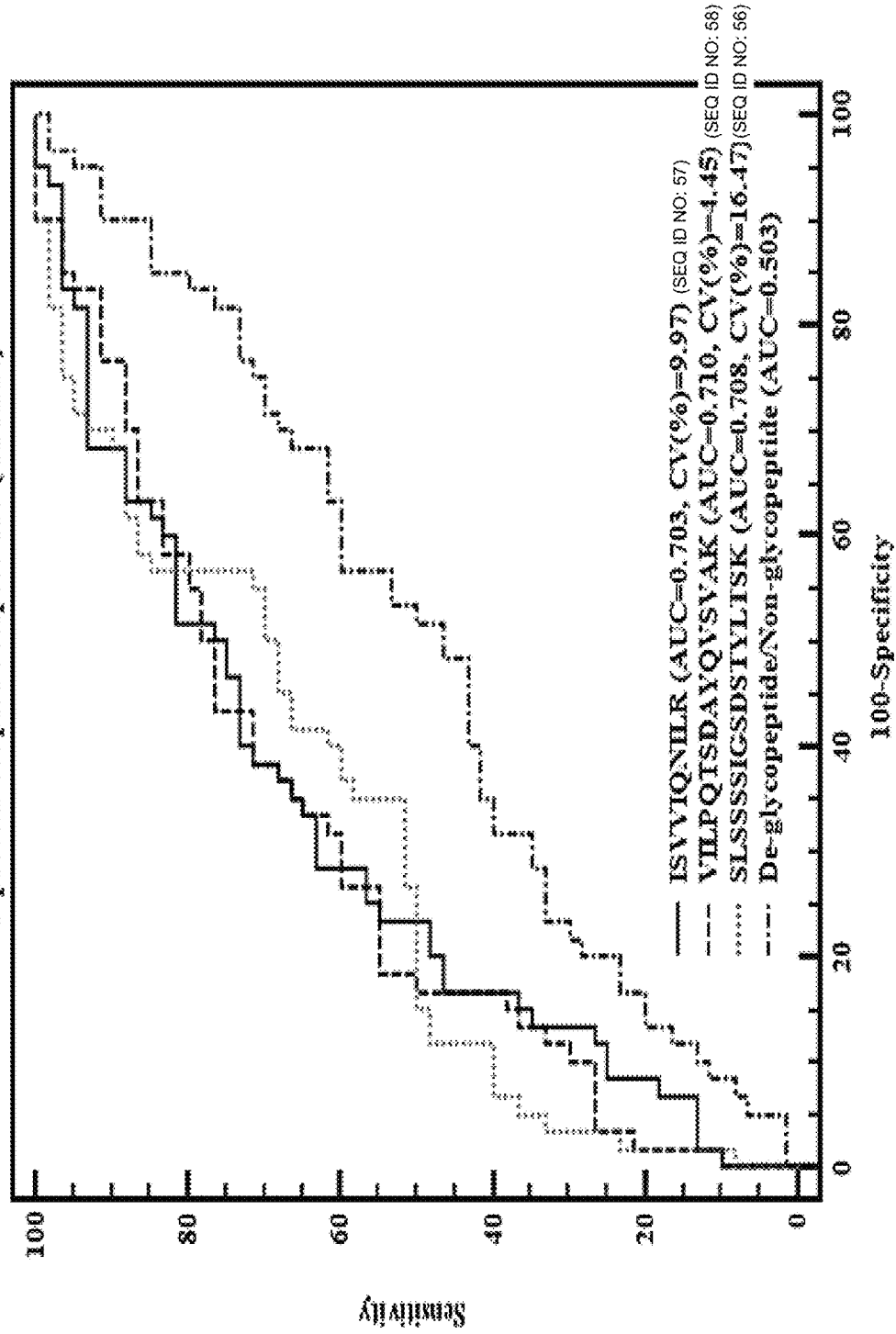
Figure 17T:
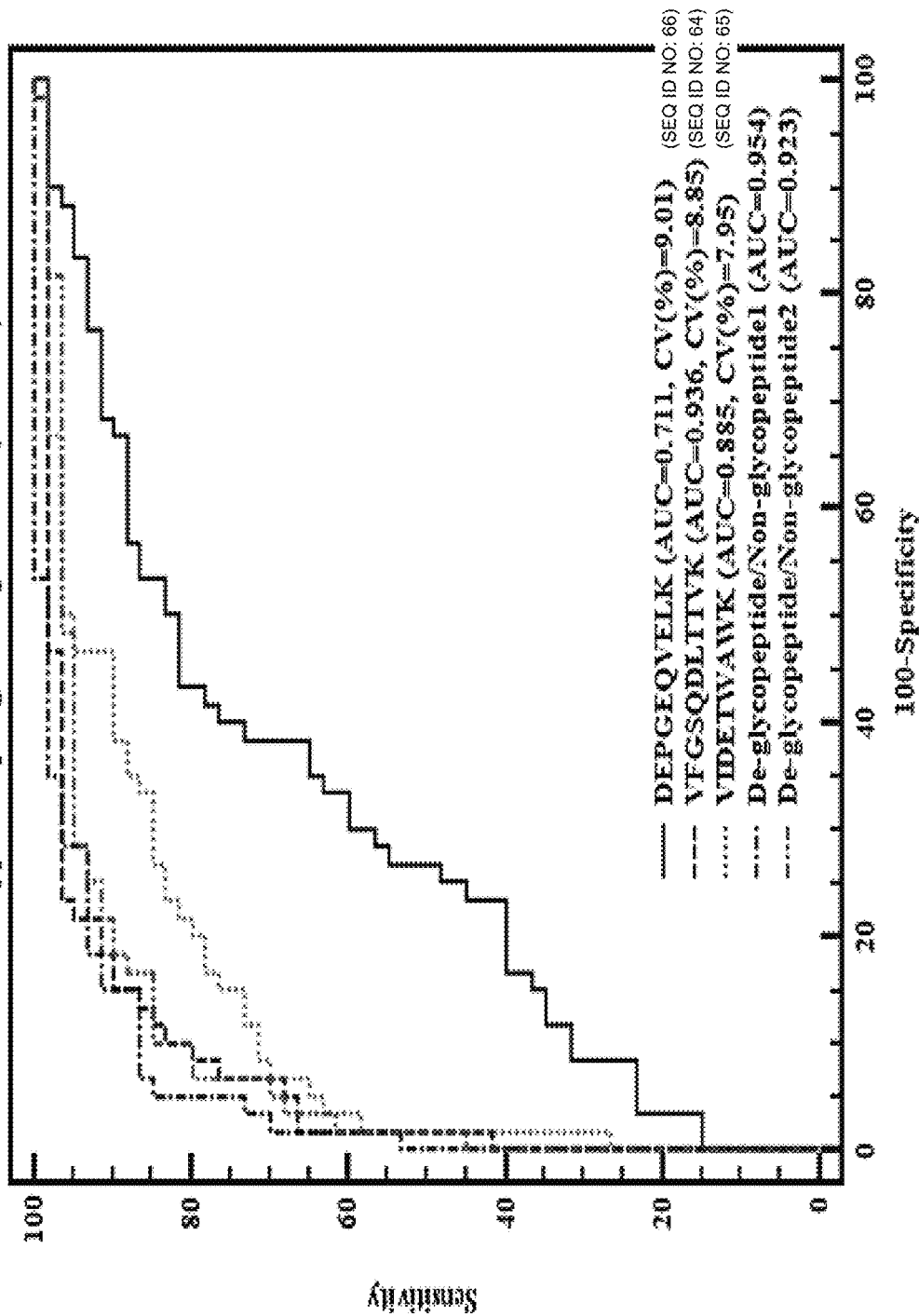
Figure 17U:
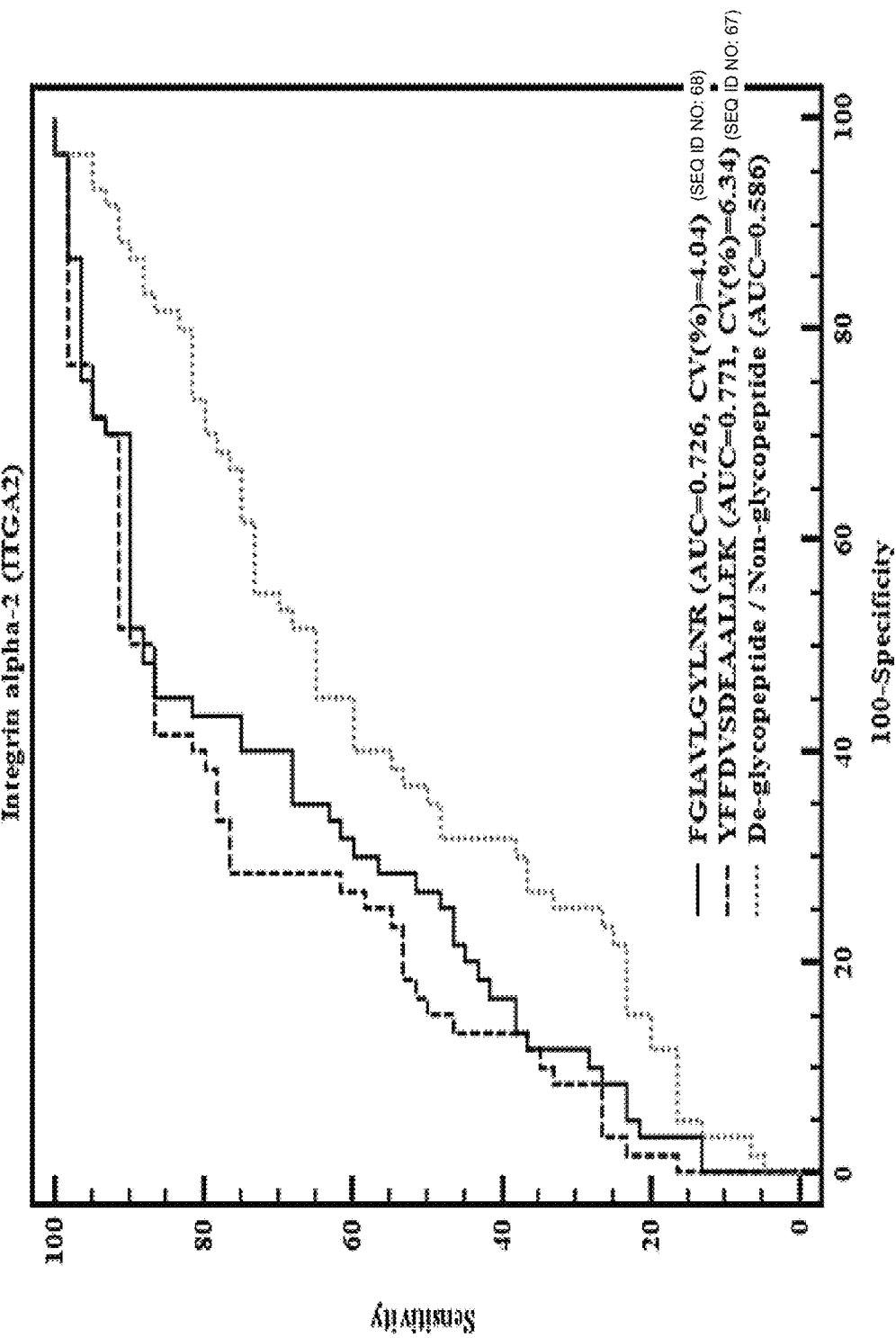
Figure 17V:
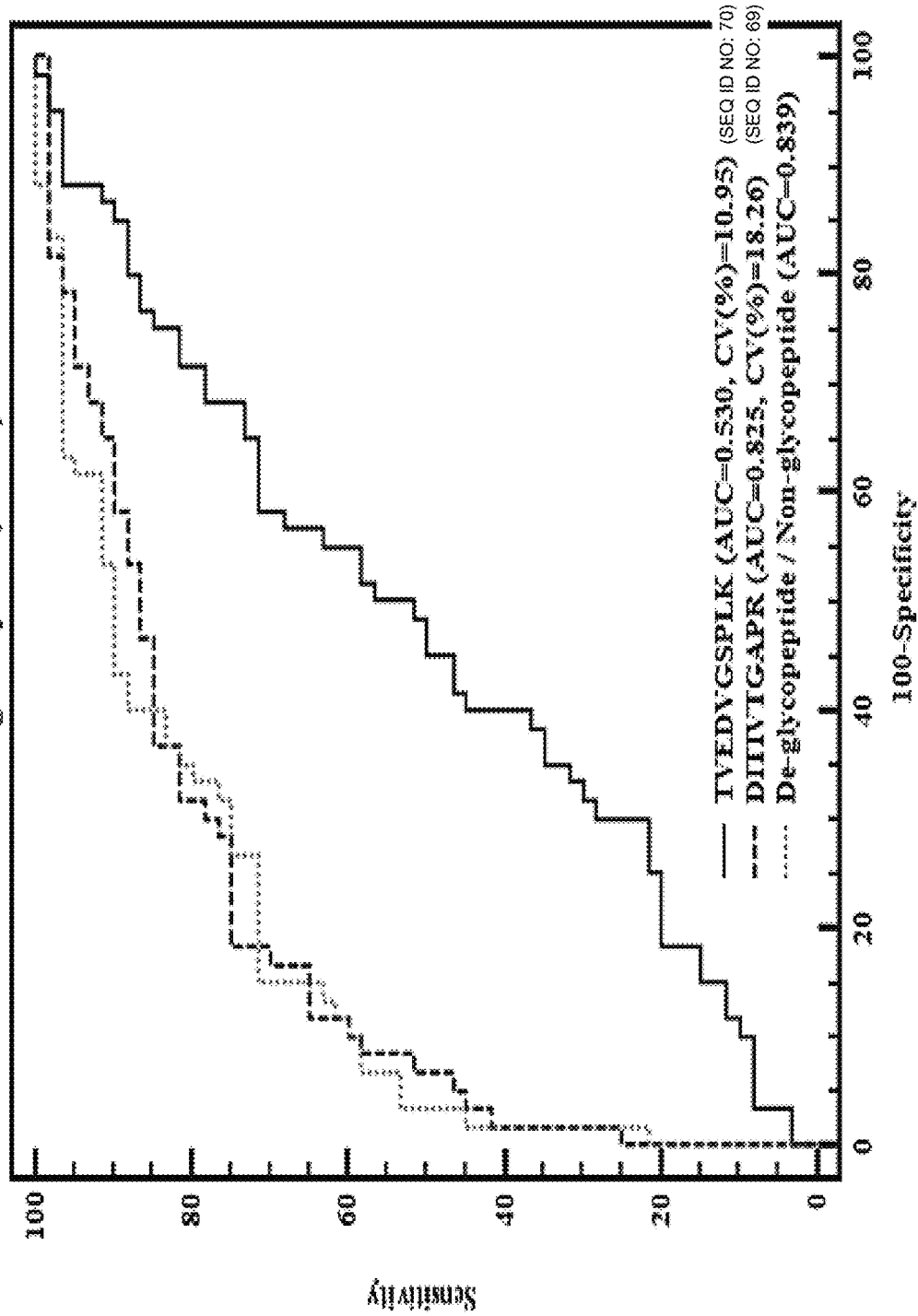
Figure 17W:
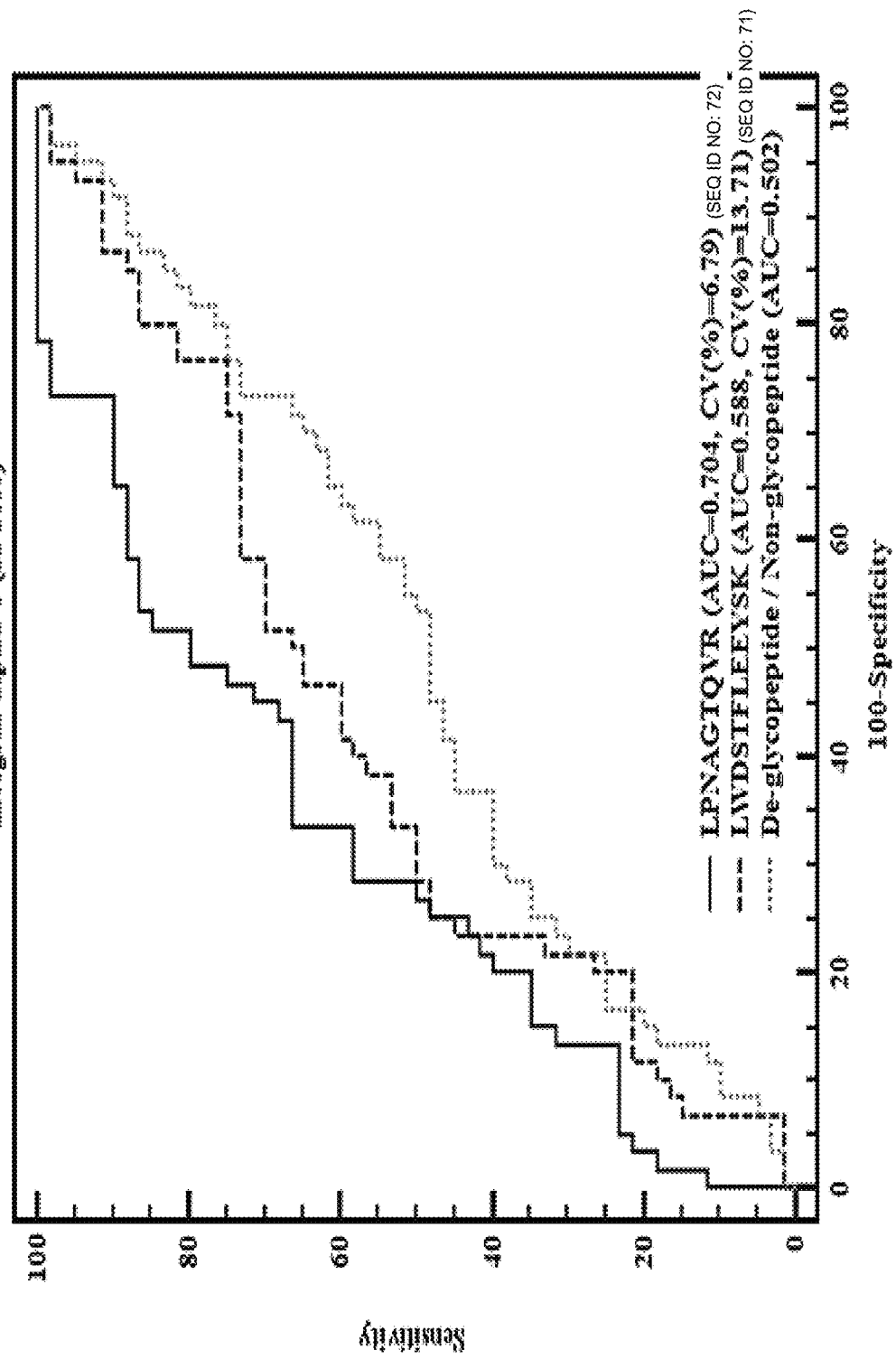
Figure 17X:
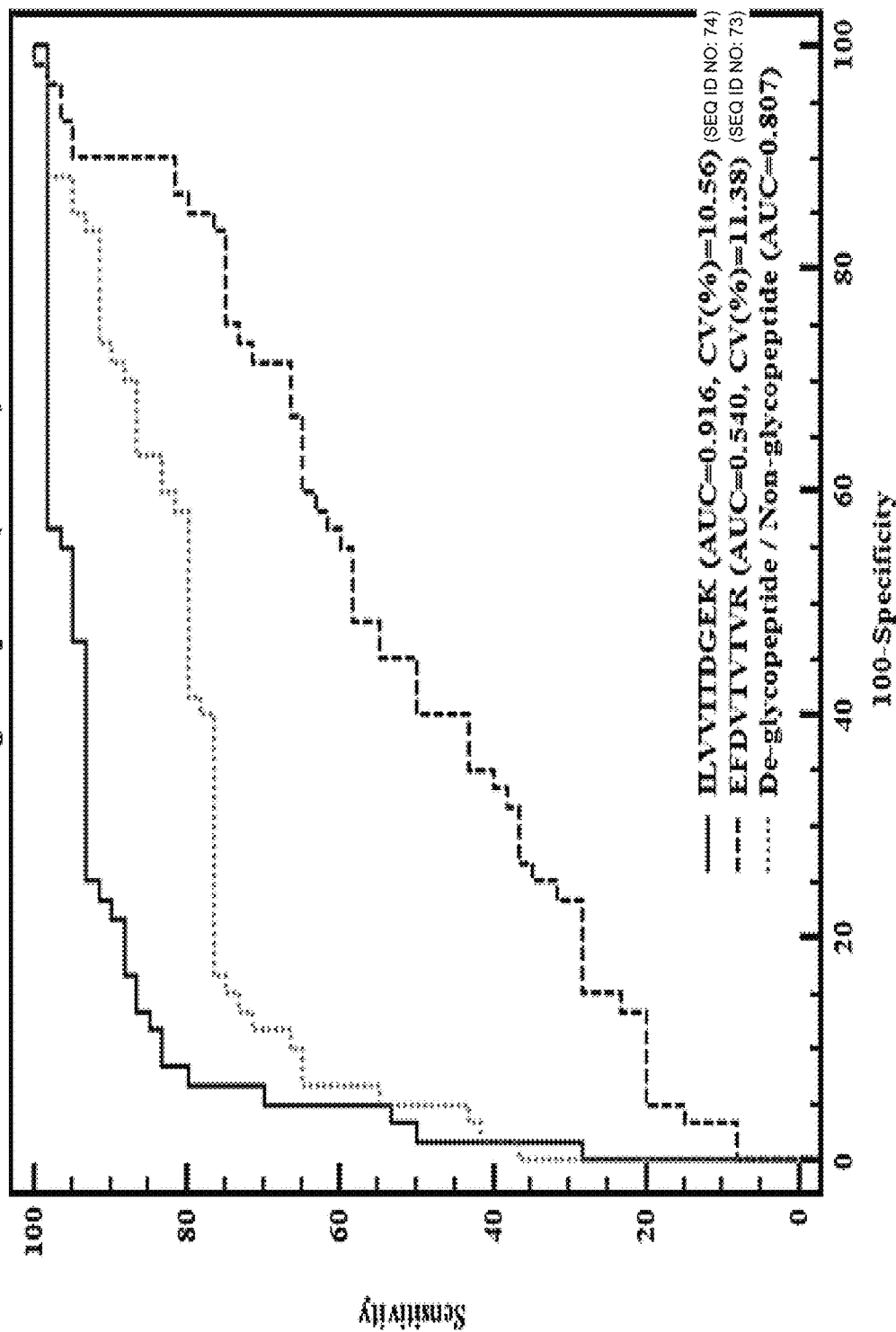
Figure 17Y:
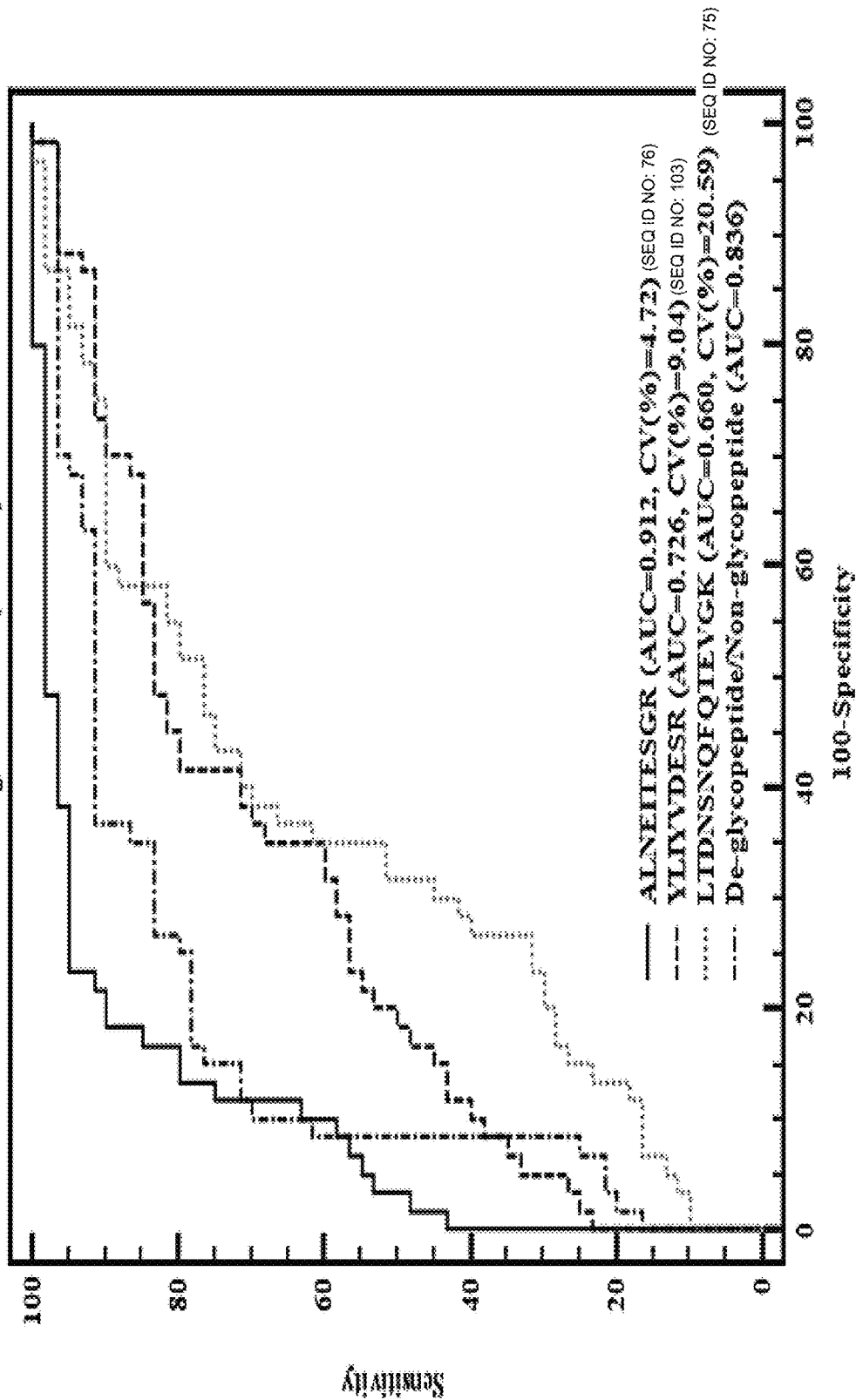
Figure 18D:
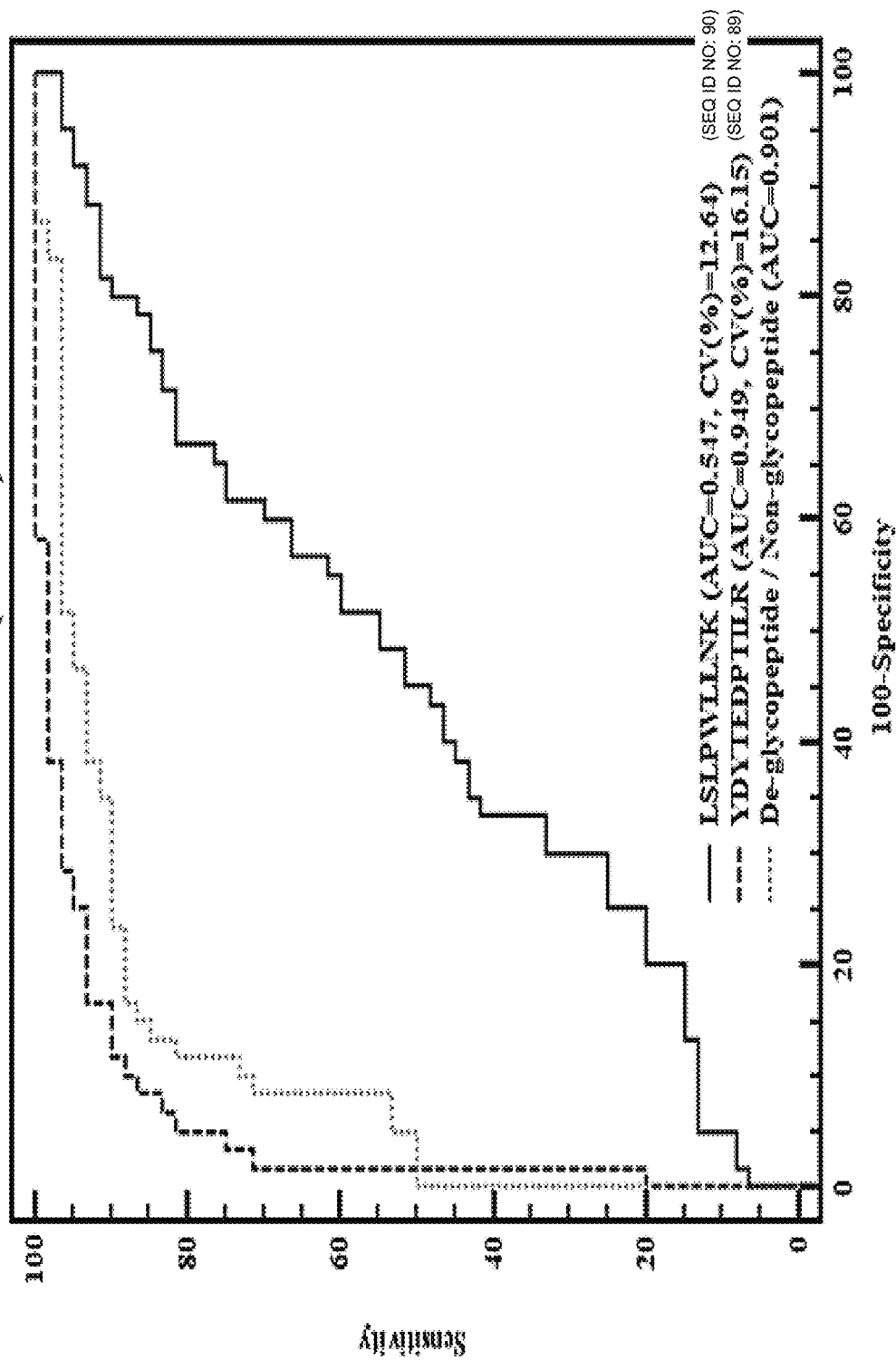
Figure 18F:
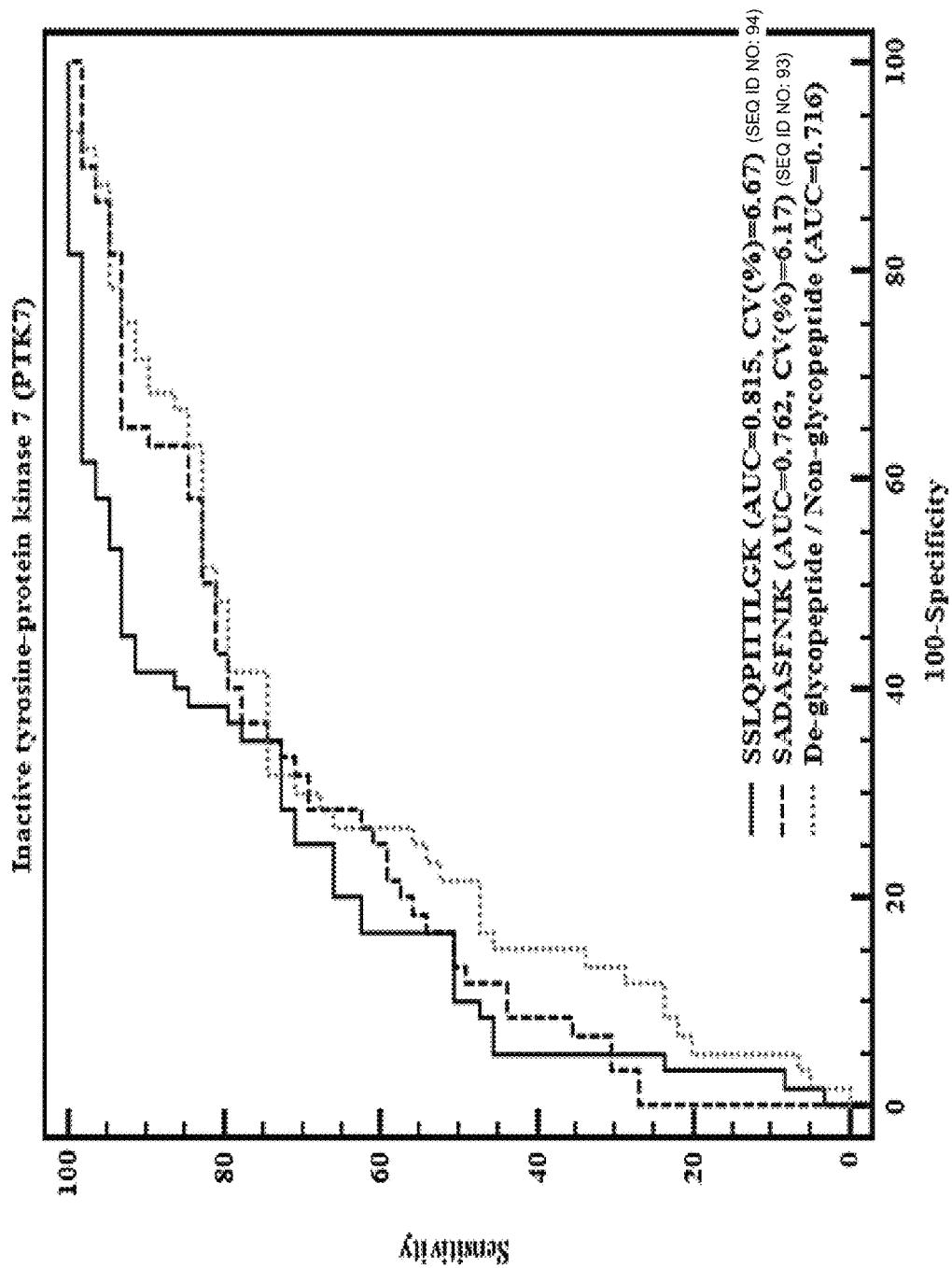
Figure 18H:
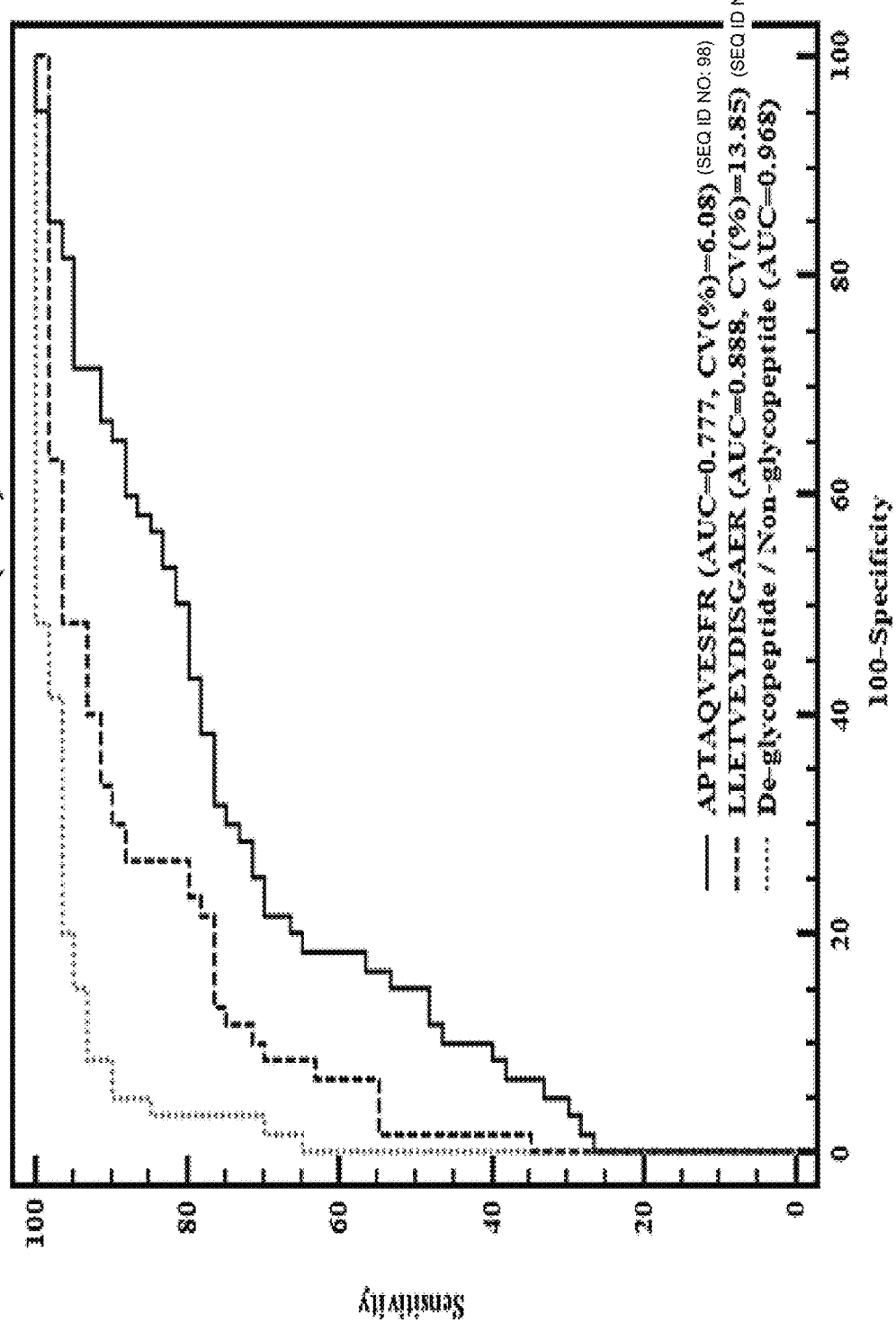
Figure 18I:
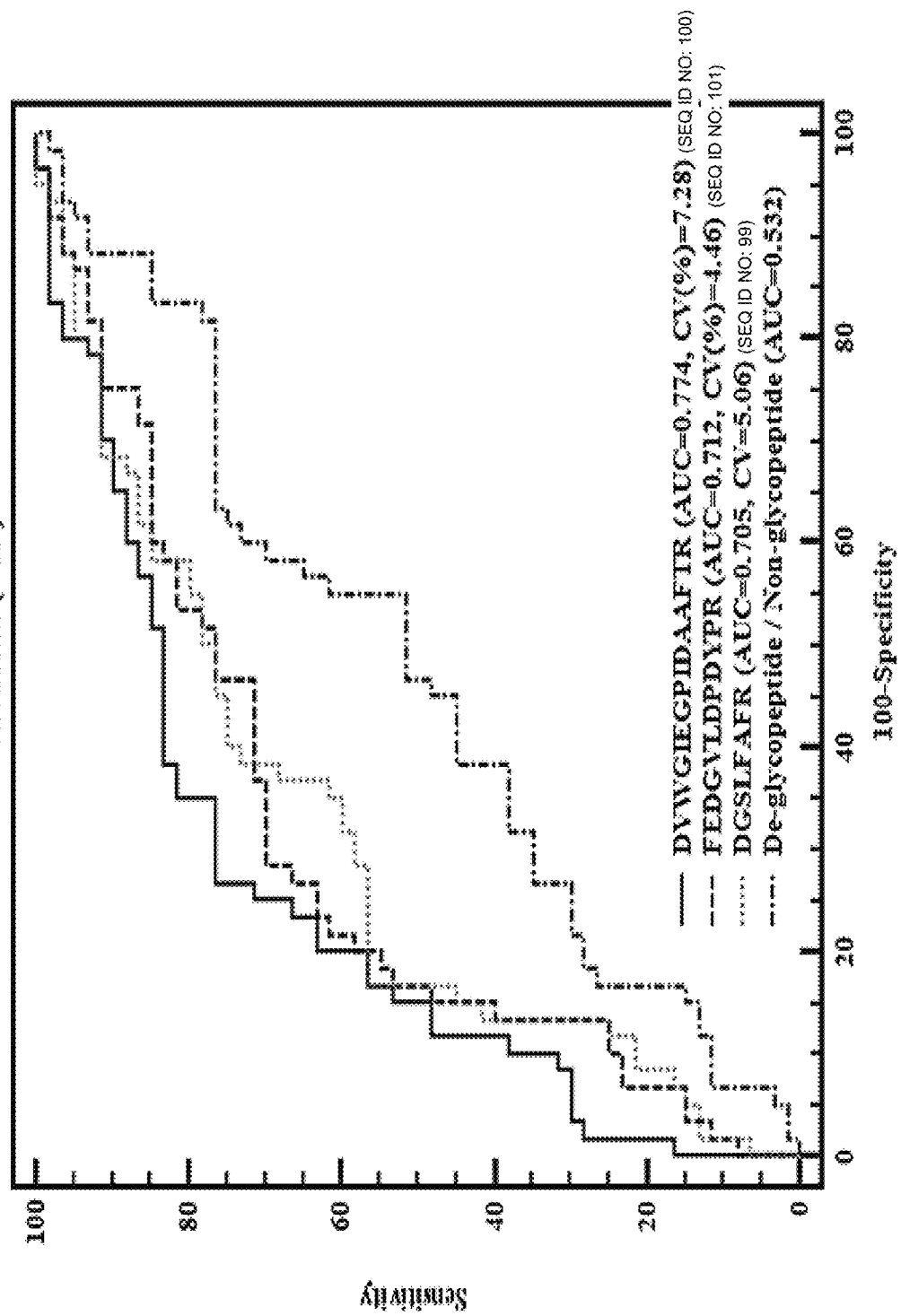

To determine the optimized collision energy (CE) for the heavy labelled synthetic peptide of AFP, a total of 11 points of CE including 2 units before and after the default CE value were analyzed for 3 times and the CE with the highest peak area was confirmed. The results are shown in FIG. 12 and Table 11. Table 11 shows the mass value (m/z) and the optimized CE value for AFP target peptide (endo/heavy).

the heavy labelled synthetic peptide. As a result, the endogenous peptides from serum and the heavy labelled synthetic peptide were eluted at the same retention time. Also the strength of the product ion type was determined to be identical. Results are shown in FIGS. 13a and 13b.

TABLE 11

| Protein name | Peptide sequence | Isotype | Precursor ion (m/z) | Product ion (m/z) | Optimized collision energy (volt) | Ion type |
|---|---|---|---|---|---|---|
| Alpha-fetoprotein (AFP) | VDFTEIQK (SEQ ID NO: 9) | light | 490.258382 | 880.441074 | 13.3 | y7 |
| | | light | 490.258382 | 765.414131 | 13.3 | y6 |
| | | light | 490.258382 | 618.345717 | 15.3 | y5 |
| | | light | 490.258382 | 517.298038 | 11.3 | y4 |
| | | light | 490.258382 | 388.255445 | 21.3 | y3 |
| | | light | 490.258382 | 275.171381 | 21.3 | y2 |
| | | light | 490.258382 | 362.171047 | 9.3 | b3 |
| | | light | 490.258382 | 463.218725 | 9.3 | b4 |
| | | light | 490.258382 | 592.261319 | 11.3 | b5 |
| | | light | 490.258382 | 705.345383 | 9.3 | b6 |
| | | light | 490.258382 | 833.40396 | 7.3 | b7 |
| | VDFTEIQK (SEQ ID NO: 9) | heavy | 494.265481 | 888.455273 | 13.3 | y7 |
| | | heavy | 494.265481 | 773.42833 | 13.3 | y6 |
| | | heavy | 494.265481 | 626.359916 | 15.3 | y5 |
| | | heavy | 494.265481 | 525.312237 | 11.3 | y4 |
| | | heavy | 494.265481 | 396.269644 | 21.3 | y3 |
| | | heavy | 494.265481 | 283.18558 | 21.3 | y2 |
| | | heavy | 494.265481 | 362.171047 | 9.3 | b3 |
| | | heavy | 494.265481 | 463.218725 | 9.3 | b4 |
| | | heavy | 494.265481 | 592.261319 | 11.3 | b5 |
| | | heavy | 494.265481 | 705.345383 | 9.3 | b6 |
| | | heavy | 494.265481 | 833.40396 | 7.3 | b7 |
| | GYQELLEK (SEQ ID NO: 10) | light | 490.258382 | 759.424636 | 11.3 | y6 |
| | | light | 490.258382 | 631.366118 | 13.3 | y5 |
| | | light | 490.258382 | 502.323525 | 15.3 | y4 |
| | | light | 490.258382 | 389.239461 | 17.3 | y3 |
| | | light | 490.258382 | 276.155397 | 21.3 | y2 |
| | | light | 490.258382 | 221.092068 | 11.3 | b2 |
| | | light | 490.258382 | 349.150646 | 9.3 | b3 |
| | | light | 430.258382 | 591.277303 | 11.3 | b5 |
| | | light | 490.258382 | 704.361367 | 7.3 | b6 |
| | | light | 490.258382 | 833.40396 | 9.3 | b7 |
| | GYQELLEK (SEQ ID NO: 10) | heavy | 494.265481 | 767.438895 | 11.3 | y6 |
| | | heavy | 494.265481 | 639.380317 | 13.3 | y5 |
| | | heavy | 494.265481 | 510.337724 | 15.3 | y4 |
| | | heavy | 494.265481 | 397.25366 | 17.3 | y3 |
| | | heavy | 494.265481 | 284.169536 | 21.3 | y2 |
| | | heavy | 494.265481 | 221.092068 | 11.3 | b2 |
| | | heavy | 494.265481 | 349.150646 | 9.3 | b3 |
| | | heavy | 494.265481 | 591.277303 | 11.3 | b5 |
| | | heavy | 494.265481 | 704.361367 | 7.3 | b6 |
| | | heavy | 494.265481 | 833.40396 | 9.3 | b7 |

Example 3-3 Determination of Endogenous AFP Target Peptide

Using a heavy labelled synthetic peptide with the same sequence as AFP target peptide (De-glycopeptide, Non-glycopeptide) except that $^{12}C$ and $^{14}N$ atoms in Arg (R) and Lys (K) residues at the C-terminal region were heavy labelled with $^{13}C$ and $^{15}N$ were used to confirm that the peptides detected are actually the endogenous peptide present in serum.

That is, the heavy labelled peptide and the endogenous peptide share the same sequence and thus have the identical hydrophobicity. Thus they can be detected on LC-column (C18) since they are eluted at the same retention time.

The de-glycosylated peptide VDFTEIQK (SEQ ID NO: 9) and the non-glycosylated peptide GYQELLEK (SEQ ID NO: 10) were analyzed on the de-glycosylated peptide obtained by treatment with PNGase-F/trypsin together with Example 3-4 Reaction Curve of the Heavy Labelled Synthetic Peptide To confirm the quantifiable property of the heavy labelled synthetic peptides to AFP target peptide, experiments to confirm the linearity of the reaction curve was performed as follows. The heavy labelled synthetic peptide for the de-glycosylated peptide VDFTEIQK (SEQ ID NO: 9) was serially diluted to 0, 0.8, 1.6, 3.1, 6.3, 12.5, 25, 50, 100 fmol. The heavy labelled synthetic peptide for the non-glycosylated peptide GYQELLEK (SEQ ID NO: 10) was serially diluted to 0, 1.6, 3.1, 6.3, 12.5, 25, 50, 100, 200 fmol. Then 5 μg of serum from the pooled sample was added to each of the diluted peptides.

Experiments were repeated 3 times for each concentration. As a result, both the synthetic peptides were found to have a linearity ($R^2$=0.995, 0.992). Results are shown in FIG. 14 and Table 12.

TABLE 12

| VDFTEIQK (SEQ ID NO: 9) (494.3/773.4)_2+_y6 | | | | | | | | | | |
|---|---|---|---|---|---|---|---|---|---|---|
| Conc. (fmol) | Blank | 0 | 0.8 | 1.6 | 3.1 | 6.3 | 12.5 | 25 | 50 | 100 |
| MeanArea | 7.00 | 307.00 | 610.00 | 1109.33 | 1296.67 | 1900.33 | 12319.33 | 25216.00 | 61973.00 | 138138.00 |
| Stdev | 5.57 | 14.11 | 61.59 | 83.20 | 12.90 | 194.20 | 76.85 | 669.63 | 1838.58 | 3336.99 |
| CV (%) | 79.54% | 4.60% | 9.62% | 7.50% | 0.99% | 10.22% | 0.62% | 2.66% | 2.831% | 2.42% |

| GYQELLEX (SEQ ID NO: 10) (494.3/767.4)_2+_y6 | | | | | | | | | | |
|---|---|---|---|---|---|---|---|---|---|---|
| Conc. (fmol) | Blank | 0.0 | 1.6 | 3.1 | 6.3 | 12.5 | 25.0 | 50.0 | 100.0 | 200.0 |
| MeanArea | 7.33 | 70.67 | 441.00 | 524.33 | 1061.33 | 8809.33 | 1686.33 | 48325.33 | 109508.67 | 259150.09 |
| Stdev | 2.31 | 48.60 | 9.64 | 28.45 | 121.23 | 277.69 | 809.40 | 1110.34 | 5383.50 | 13769.43 |
| CV (%) | 31.49% | 68.78% | 2.19% | 5.43% | 11.39% | 3.15% | 5.03% | 2.30% | 4.92% | 5.31% |

Example 4. Determination of Correlation Between Clinical Result and MRM Data EXAMPLE 4-1 Classification 1 According to the Detection (Normal Control)

MRM analysis was performed on 60 normal samples as described in Example. As shown in Table 13-1 to 13-3, the de-glycosylated peptide VDFTEIQK (SEQ ID NO: 9) was detected in two samples (3.3%) out of sixty. The non-glycosylated peptide GYQELLEK (SEQ ID NO: 10) was detected in seven samples out of sixty samples (11.7%). Based on this, the specificity with which the liver cancer can be differentiated from the normal person was found to be 96.7% for the de-glycosylated peptide and 88.3% for the non-glycosylated peptide.

TABLE 13-1

| N. | T. # | Set 1 Test Date | Sex | Age | Detection Deglycopeptide | (Normal group) Non-glycopeptide |
|---|---|---|---|---|---|---|
| 1 | N12-051 | 2012 Mar. 28 | M | 53 | Not detected | Not detected |
| 2 | N12-052 | 2012 Mar. 23 | M | 43 | Not detected | Not detected |
| 3 | N12-055 | 2012 Mar. 23 | M | 59 | Not detected | Not detected |
| 4 | N12-057 | 2012 Mar. 23 | M | 59 | Not detected | Not detected |
| 5 | N12-059 | 2012 Mar. 28 | M | 42 | Not detected | Not detected |
| 6 | N12-061 | 2012 Mar. 23 | M | 61 | Not detected | Detected |
| 7 | N12-062 | 2012 Mar. 23 | M | 60 | Not detected | Detected |
| 8 | N12-069 | 2012 Mar. 23 | M | 47 | Not detected | Not detected |
| 9 | N12-081 | 2012 Mar. 23 | M | 51 | Not detected | Detected |
| 10 | N12-082 | 2012 Mar. 29 | M | 44 | Not detected | Not detected |
| 11 | N12-085 | 2012 Mar. 26 | M | 42 | Not detected | Not detected |
| 12 | N12-086 | 2012 Mar. 26 | M | 51 | Not detected | Not detected |
| 13 | N12-088 | 2012 Mar. 26 | M | 54 | Not detected | Not detected |
| 14 | N12-095 | 2012 Mar. 26 | M | 69 | Not detected | Not detected |
| 15 | N12-054 | 2012 Mar. 28 | F | 66 | Not detected | Not detected |
| 16 | N12-060 | 2012 Mar. 23 | F | 64 | Not detected | Not detected |
| 17 | N12-075 | 2012 Mar. 28 | F | 55 | Detected | Not detected |
| 18 | N12-084 | 2012 Mar. 26 | F | 53 | Not detected | Not detected |
| 19 | N12-087 | 2012 Mar. 26 | F | 39 | Not detected | Not detected |
| 20 | N12-108 | 2012 Mar. 26 | F | 51 | Not detected | Not detected |

TABLE 13-2

| N. | T. # | Set 2 Test Date | Sex | Age | Detection Deglycopeptide | (Normal group) Non-glycopeptide |
|---|---|---|---|---|---|---|
| 21 | N12-096 | 2012 Mar. 26 | M | 48 | Not detected | Not detected |
| 22 | N12-097 | 2012 Mar. 26 | M | 55 | Not detected | Not detected |
| 23 | N12-101 | 2012 Mar. 26 | M | 48 | Not detected | Not detected |
| 24 | N12-109 | 2012 Mar. 26 | M | 69 | Not detected | Not detected |
| 25 | N12-112 | 2012 Mar. 26 | M | 70 | Not detected | Not detected |
| 26 | N12-120 | 2012 Mar. 26 | M | 45 | Not detected | Not detected |
| 27 | N12-122 | 2012 Mar. 26 | M | 52 | Not detected | Not detected |
| 28 | N12-125 | 2012 Mar. 26 | M | 59 | Not detected | Not detected |
| 29 | N12-126 | 2012 Mar. 26 | M | 47 | Not detected | Not detected |
| 30 | N12-127 | 2012 Mar. 26 | M | 66 | Not detected | Detected |
| 31 | N12-130 | 2012 Mar. 26 | M | 53 | Not detected | Not detected |
| 32 | N12-181 | 2012 Mar. 26 | M | 43 | Not detected | Not detected |
| 33 | N12-188 | 2012 Mar. 28 | M | 43 | Not detected | Not detected |
| 34 | N12-199 | 2012 Mar. 28 | M | 56 | Not detected | Not detected |
| 35 | N12-110 | 2012 Mar. 26 | F | 62 | Not detected | Not detected |
| 36 | N12-117 | 2012 Mar. 26 | F | 49 | Not detected | Not detected |

TABLE 13-2-continued

| N. | T. # | Set 2 Test Date | Sex | Age | Detection Deglycopeptide | (Normal group) Non-glycopeptide |
|---|---|---|---|---|---|---|
| 37 | N12-119 | 2012 Mar. 26 | F | 37 | Not detected | Not detected |
| 38 | N12-128 | 2012 Mar. 26 | F | 42 | Not detected | Not detected |
| 39 | N12-189 | 2012 Mar. 28 | F | 58 | Not detected | Not detected |
| 40 | N12-202 | 2012 Mar. 28 | F | 65 | Not detected | Not detected |

TABLE 13-3

| N. | T. # | Set 3 Test Date | Sex | Age | Detection Deglycopeptide | (Normal group) Non-glycopeptide |
|---|---|---|---|---|---|---|
| 41 | N12-218 | 2012 Mar. 29 | M | 58 | Not detected | Not detected |
| 42 | N12-216 | 2012 Mar. 29 | M | 46 | Not detected | Not detected |
| 43 | N12-217 | 2012 Mar. 29 | M | 61 | Not detected | Not detected |
| 44 | N12-219 | 2012 Mar. 29 | M | 43 | Not detected | Detected |
| 45 | N12-220 | 2012 Mar. 29 | M | 58 | Not detected | Not detected |
| 46 | N12-225 | 2012 Mar. 29 | M | 58 | Not detected | Not detected |
| 47 | N12-228 | 2012 Mar. 29 | M | 58 | Not detected | Not detected |
| 48 | N12-229 | 2012 Mar. 29 | M | 52 | Not detected | Not detected |
| 49 | N12-288 | 2012 Mar. 29 | M | 53 | Not detected | Not detected |
| 50 | N12-239 | 2012 Mar. 29 | M | 57 | Not detected | Not detected |
| 51 | N12-249 | 2012 Mar. 29 | M | 57 | Not detected | Not detected |
| 52 | N12-254 | 2012 Mar. 30 | M | 56 | Not detected | Not detected |
| 53 | N12-258 | 2012 Mar. 30 | M | 51 | Not detected | Not detected |
| 54 | N12-261 | 2012 Mar. 30 | M | 51 | Not detected | Not detected |
| 55 | N12-204 | 2012 Mar. 28 | F | 44 | Not detected | Detected |
| 56 | N12-218 | 2012 Mar. 29 | F | 59 | Not detected | Not detected |
| 57 | N12-221 | 2012 Mar. 29 | F | 85 | Not detected | Not detected |
| 58 | N12-226 | 2012 Mar. 29 | F | 54 | Not detected | Not detected |
| 59 | N12-235 | 2012 Mar. 29 | F | 53 | Detected | Detected |
| 60 | N12-241 | 2012 Mar. 29 | F | 50 | Not detected | Not detected |

Example 4-2 Classification 2 According to the Detection (HCC Group)

MRM analysis was performed on 60 HCC samples as described in Example 3. As shown in Tables 14-1 to 14-3, the de-glycosylated peptide (VDFTEIQK) (SEQ ID NO: 9) was detected in 39 samples out of 60 (65.0%). The non-glycosylated peptide (GYQELLEK) (SEQ ID NO: 10) was detected in 32 samples out of 60 samples (53.3%). Based on this, it was determined that the sensitivity to determine the cancer as cancer is 65.0% for the de-glycosylated peptide and 53.3% for the non-glycosylated peptide.

TABLE 14-1

| # | Gender | Age | Set 1 AFP(0-20) | PIVKA | Virus | Treatment | Detection De-glycopeptide | (HCC group) Non-glycopeptide |
|---|---|---|---|---|---|---|---|---|
| 1 | M | 57 | 8 | 516 | HBV | TACE | Not detected | Not detected |
| 2 | M | 56 | 12700 | 25 | HBV | TACE | Detected | Detected |
| 3 | M | 62 | 45 | 30 | HBV | RFA | Not detected | Detected |
| 4 | M | 61 | 13 | NA | HBV | RFA | Not detected | Not detected |
| 5 | M | 46 | 13200 | 189 | HBV | TACE & PEIT | Detected | Detected |
| 6 | M | 64 | 6 | 13 | HBV | TACE | Not detected | Not detected |
| 7 | M | 65 | 6 | 118 | HBV | TACE | Detected | Not detected |
| 8 | M | 50 | 6 | 107 | HBV | PEIT | Not detected | Not detected |
| 9 | M | 57 | <5 | 912 | HBV | TACE | Not detected | Detected |
| 10 | M | 54 | 337 | 6604 | HBV | TACE(06/1/11) | Detected | Detected |
| 11 | M | 56 | 10 | NA | HBV | TACE | Not detected | Not detected |
| 12 | M | 62 | 2240 | 37 | HBV | PEITT | Detected | Detected |
| 13 | M | 60 | 351 | 644 | HBV | TACE | Detected | Detected |
| 14 | M | 61 | 34 | 39 | HBV | TACE | Detected | Not detected |
| 15 | F | 42 | 283000 | 1560 | HBV | TACE | Detected | Detected |
| 16 | F | 66 | 10 | 41 | HBV | RFA | Detected | Not detected |
| 17 | F | 74 | 10 | 74 | HBV | TACE, PEIT | Not detected | Detected |
| 18 | F | 71 | <5 | 675 | HBV | TACE | Not detected | Not detected |
| 19 | F | 61 | 6 | 7 | HBV | PEIT | Detected | Not detected |
| 20 | F | 69 | 473 | 117 | HBV | PEIT | Detected | Detected |

TABLE 14-2

| # | Gender | Age | Set 2 AFP(0-20) | PIVKA | Virus | Treatment | Detection De-glycopeptide | (HCC group) Non-glycopeptide |
|---|---|---|---|---|---|---|---|---|
| 21 | M | 70 | 8 | 3628 | HBV | TACE(06/4/15) | Not detected | Not detected |
| 22 | M | 47 | 346 | 3447 | HBV | TACE | Detected | Detected |
| 23 | M | 49 | 1690 | 786 | HBV | TACE | Detected | Detected |
| 24 | M | 61 | <5 | 3 | HBV | PEIT | Not detected | Detected |
| 25 | M | 62 | 1610 | 11641 | HBV | TACE | Detected | Detected |
| 26 | M | 66 | 7 | 57 | HBV | PEIT | Detected | Not detected |
| 27 | M | 57 | 73 | 1270 | HBV | TACE | Detected | Detected |
| 28 | M | 58 | 360 | 281 | HBV | PEIT | Detected | Detected |
| 29 | M | 60 | 164 | 23 | HBV | TACE | Detected | Not detected |
| 30 | M | 75 | 3530 | 1577 | HBV | TACE | Detected | Detected |
| 31 | M | 59 | 1330 | 7433 | HBV | TACE | Detected | Detected |
| 32 | M | 44 | 18 | 1646 | HBV | TACE + PEIT | Not detected | Not detected |
| 33 | M | 61 | 12 | 29 | HBV | TACE -> PEI | Not detected | Detected |
| 34 | M | 59 | 29 | 21 | HBV | PEIT | Not detected | Not detected |
| 35 | F | 54 | 18 | 61 | HBV | PEIT | Not detected | Detected |
| 36 | F | 63 | 16 | 21 | HBV | PEIT | Detected | Detected |
| 37 | F | 51 | 29 | 32 | HBV | op | Detected | Detected |
| 38 | F | 63 | 364 | 159 | HBV | TACE | Detected | Detected |
| 39 | F | 42 | 1000 | 24 | HBV | PEIT | Detected | Detected |
| 40 | F | 63 | 7 | 12 | HBV | TACE | Detected | Not detected |

TABLE 14-3

| # | Gender | Age | Set 3 AFP(0-20) | PIVKA | Virus | Treatment | Detection De-glycopeptide | (HCC group) Non-glycopeptide |
|---|---|---|---|---|---|---|---|---|
| 41 | M | 54 | 24 | 19 | HBV | PEIT | Detected | Not detected |
| 42 | M | 58 | 40300 | 3522 | HBV | TACE | Detected | Detected |
| 43 | M | 53 | 217 | 29 | HBV | TACE | Detected | Detected |
| 44 | M | 56 | 222000 | 1969 | HBV | TACE | Detected | Detected |
| 45 | M | 63 | 6 | 2706 | HBV | TACE | Detected | Not detected |
| 46 | M | 38 | 105200 | 1005 | HBV | TACE | Detected | Detected |
| 47 | M | 55 | 25 | 17 | HBV | PEIT | Not detected | Detected |
| 48 | M | 48 | 7.1 | 31 | HBV | PEIT | Detected | Not detected |
| 49 | M | 60 | 7.8 | 50 | HBV | PEIT | Not detected | Not detected |
| 50 | M | 76 | 74 | 5 | HBV | PEIT | Detected | Detected |
| 51 | M | 47 | 3.2 | 25 | HBV | PEIT | Not detected | Not detected |
| 52 | M | 58 | 14.1 | 34 | HBV | PEIT(4/25-16) | Detected | Not detected |
| 53 | M | 58 | 350 | 9 | HBV | PEIT | Detected | Not detected |
| 54 | M | 56 | 5.5 | 188 | HBV | TACE(6/30) | Not detected | Not detected |
| 55 | F | 74 | 15 | 81 | HBV | TACE | Detected | Not detected |
| 56 | F | 67 | 43 | 56 | HBV | PEIT | Not detected | Not detected |
| 57 | F | 56 | 971 | 37 | HBV | TACE | Detected | Not detected |
| 58 | F | 46 | 1088 | 10 | HBV | TACE(3/13) | Detected | Detected |
| 59 | F | 47 | 435.6 | 29 | HBV | PEIT | Detected | Not detected |
| 60 | F | 57 | 5.8 | 9 | HBV | PEIT(1/1-2) | Not detected | Not detected |

Example 4-3 Correlation Between Clinical Results and MRM Results

The level of AFP was measured in 60 HCC patients using commercially available AFP kit (Bioland; NanoSign AFP, Nanoentech; AFP quantification kit) commonly used in clinics according to the manufacturer's instruction (clinical results). Then the data obtained using AFP kit were compared to the MRM data as described in Example 3 to determine the correlation between the two data set. As shown in FIG. 15, de-glycosylated peptide of AFP protein (VDFTEIQK) (SEQ ID NO: 9) was found to have a $R^2$ value of 0.8368, the non-glycosylated peptide (GYQELLEK) (SEQ ID NO: 10) was found to have a $R^2$ value of 0.8868. This indicates that the two data set, i.e., AFP data and MRM data are correlated to each other in a quantitative manner.

Further to confirm the efficiency of the diagnosis using the present method, ROC (Receiver-Operating Characteristic) curve was determined on 60 normal controls and HCC patients to obtain AUC (Area Under Curve). As a result, it was found that the non-glycosylated peptide (GYQELLEK) (SEQ ID NO: 10) was found to have an AUC value of 0.734, and the de-glycosylated peptide (VDFTEIQK) (SEQ ID NO: 9) was found to have an AUC value of 0.811.

Then the non-glycosylated and de-glycosylated peptides data from AFP protein were combined into one panel using logistic regression model. As a result, it was found that 58 normal people out of 60 were determined as being normal and 2 were determined as having cancer; and 41 liver cancer patients out of 60 were determined as having cancer, and 19 patients were determined as being normal. Thus the accuracy was 82.5%. That is, as shown in Table 15, as a result of comparison of AUC value using the non-glycosylated peptide, de-glycosylated peptide and the combination thereof, the two-peptide panel was found to have a higher value (AUC=0.852) to differentiate liver cancer from normal patients compared to each of the peptide.

This indicates that by monitoring both the non-glycosylated peptide (GYQELLEK) (SEQ ID NO: 10) and the de-glycosylated peptide (VDFTEIQK) (SEQ ID NO: 9) of AFP which were obtained by treating the blood sample of patients with PNGase-F/trypsin, the liver cancer can be differentiated from normal sample with high specificity.

TABLE 15

| Group | Predicted group | | Percent correct |
| --- | --- | --- | --- |
| | Normal group | HCC group | |
| Normal group | 58 | 2 | 96.67% |
| HCC group | 19 | 41 | 68.33% |
| Percent of cases correctly classified | | | 82.50% |

Example 5. MRM Analysis to Discover Additional Glycoprotein Markers in Addition to AFP Three hundred fifty four proteins corresponding to the non-glycosylated peptides selected in Example 2-5, 145 proteins corresponding to 1000 peptides and de-glycosylated peptides, and 182 peptides were applied to individual samples. Then the proteins showing the difference between normal and patient groups were selected as final target protein marker.

In the analysis, normal and patient samples were analyzed alternatively, that is, normal sample No. 1, liver cancer sample No. 1, normal sample No. 2 followed by liver cancer sample No. 2 and the like. The data obtained were fed into Skyline software and analyzed using MedCalc (version 12.2). As a result, 35 proteins showing the difference between the normal and liver cancer sample were selected as follows: Alpha-2-antiplasmin (SERPINF2), Alpha-2-macroglobulin (A2M), Apolipoprotein B-100 (APOB), Beta-galactosidase (GLB1), Bone morphogenetic protein 1 (BMP1), Corticosteroid-binding globulin (SERPINA6), Complement factor H (CFH), Cholinesterase (BCHE), Clusterin (CLU), Collagen alpha-1(XII) chain (COL12A1), Carboxypeptidase N subunit 2 (CPN2), Versican core protein (VCAN), Receptor tyrosine-protein kinase erbB-3 (ERBB3), Coagulation factor V (F5), Coagulation factor XI (F11), Follistatin-related protein 1 (FSTL1), N-acetylglucosamine-6-sulfatase (GNS), G-protein coupled receptor 126 (GPR126), Heparin cofactor 2 (SERPIND1), Hypoxia up-regulated protein 1 (HYOU1), Integrin alpha-2 (ITGA2), Integrin alpha-3 (ITGA3), Integrin alpha-6 (ITGA6), Integrin alpha-M (ITGAM), Integrin beta-2 (ITGB2), Plasma kallikrein (KLKB1), Kinectin (KTN1), Lysosome-associated membrane glycoprotein 2 (LAMP2), Galectin-3-binding protein (LGALS3BP), Plexin-A1 (PLXNA1), Periostin (POSTN), Inactive tyrosine-protein kinase 7 (PTK7), Roundabout homolog 4 (ROBO4), Tenascin (TNC), Vitronectin (VTN)

The ROC curves were drawn for each of the 35 target proteins. A ROC curve is a graphical plot that illustrates the changing relationship between the specificity and sensitivity. In ROC curves, bigger AUC (area under curve) value indicates better diagnosis ability. The AUC values determined were listed in Table 16-1 and 16-2. ROC curve and the correlation plot were prepared using MedCalc (version 12.2) statistical program.

TABLE 16-1

| N. | Protein Name | Peptide Sequence | SEQ ID NO | Precursor Mz | Precursor Charge | Product Mz | Product Charge | Fragment Ion | AUC-value Normal vs. HCC |
| --- | --- | --- | --- | --- | --- | --- | --- | --- | --- |
| 1 | Alpha-2-antiplasmin (SERPINF2) | LGNQEPGGQTALK | (SEQ ID NO: 12) | 656.8 | 2 | 771.4 | 1 | Y8 | 0.796 |
| | | NPDPSAPR | (SEQ ID NO: 11) | 427.2 | 2 | 527.3 | 1 | y5 | 0.799 |
| 2 | Alpha-2-macroglobulin (A2M) | AIGYLNTGYQR | (SEQ ID NO: 14) | 628.3 | 2 | 738.4 | 1 | y6 | 0.941 |
| | | FEVQVTVPK | (SEQ ID NO: 15) | 523.8 | 2 | 244.2 | 1 | y2 | 0.938 |
| | | IAQWQSFQLEGGLK | (SEQ ID NO: 16) | 802.9 | 2 | 978.5 | 1 | y9 | 0.941 |
| | | NEDSLVFVQTDK | (SEQ ID NO: 17) | 697.8 | 2 | 737.4 | 1 | y6 | 0.934 |
| | | VSDQTLSLFFTVLQDVPVR | (SEQ ID NO: 13) | 1082.6 | 2 | 1320.7 | 1 | y11 | 0.861 |
| | | VSVQLEASPAFLAVPVEK | (SEQ ID NO: 18) | 942.5 | 2 | 472.3 | 1 | y4 | 0.852 |
| 3 | Apolipoprotein B-100 (APOB) | FEVDSPVYDATWSASLK | (SEQ ID NO: 19) | 958.0 | 2 | 1337.7 | 1 | y12 | 0.526 |
| | | LSLESLTSYFSIESSTK | (SEQ ID NO: 20) | 946.5 | 2 | 1249.6 | 1 | y11 | 0.707 |
| 4 | Beta-galactosidase (GLB1) | NNVITLDITGK | (SEQ ID NO: 21) | 594.3 | 2 | 655.4 | 1 | b6 | 0.857 |
| | | VNYGAYINDFK | (SEQ ID NO: 22) | 652.3 | 2 | 870.4 | 1 | y7 | 0.912 |
| 5 | Bone morphogenetic protein 3 (BMP1) | GIFLDTIVPK | (SEQ ID NO: 24) | 551.8 | 2 | 672.4 | 1 | y6 | 0.916 |
| | | IILDFTSLDLYR | (SEQ ID NO: 23) | 734.9 | 2 | 703.4 | 1 | b6 | 0.556 |
| 6 | Corticosteroid-binding globulin (SERPINA6) | AQLLQGLGFDLTER | (SEQ ID NO: 25) | 780.9 | 2 | 928.5 | 1 | b9 | 0.815 |
| | | ITQDAQLK | (SEQ ID NO: 26) | 458.8 | 2 | 215.1 | 1 | b2 | 0.524 |
| | | WSAGLTSSQVDLYIPK | (SEQ ID NO: 27) | 883.0 | 3 | 357.2 | 1 | y3 | 0.519 |
| 7 | Complement factor H (CFH) | SPDVIDGSPISQK | (SEQ ID NO: 28) | 671.8 | 2 | 831.4 | 1 | y8 | 0.531 |
| | | SSIDIENGFISESQYTYALK | (SEQ ID NO: 29) | 1133.0 | 2 | 1076.5 | 1 | b10 | 0.853 |
| 8 | Cholinesterase (BCHE) | AILQSGSFNAPWAYTSLYEAR | (SEQ ID NO: 31) | 1141.1 | 2 | 1292.7 | 1 | y11 | 0.745 |
| | | IFFPGVSEFGK | (SEQ ID NO: 32) | 614.3 | 2 | 261.2 | 1 | b2 | 0.745 |
| | | WSDIWDATK | (SEQ ID NO: 30) | 561.3 | 2 | 935.4 | 1 | y8 | 0.703 |
| | | YLTLNTESTR | (SEQ ID NO: 33) | 599.3 | 2 | 921.5 | 1 | y8 | 0.789 |
| 9 | Clusterin (CLU) | ASSIIDELFQDR | (SEQ ID NO: 35) | 697.4 | 2 | 922.4 | 1 | y7 | 0.826 |
| | | EIQNAVGVK | (SEQ ID NO: 36) | 536.3 | 2 | 701.4 | 1 | y7 | 0.766 |
| | | LADLTQGEDQYYLR | (SEQ ID NO: 102) | 842.9 | 2 | 1043.5 | 1 | y8 | 0.842 |
| 10 | Collagen alpha-1 (XII) chain (COL12A1) | ITEVTSEGFR | (SEQ ID NO: 38) | 569.8 | 2 | 696.3 | 1 | y6 | 0.586 |
| | | NVQVYDPTPNSLDVR | (SEQ ID NO: 37) | 858.9 | 2 | 800.4 | 1 | y7 | 0.882 |
| | | VQISLVQYSR | (SEQ ID NO: 39) | 506.8 | 2 | 652.3 | 1 | y5 | 0.628 |
| | | VYDPSTSTLNVR | (SEQ ID NO: 40) | 676.3 | 2 | 689.4 | 1 | y6 | 0.522 |
| 11 | Carboxypeptidase N subunit 2 (CPN2) | AFGSNPDLTK | (SEQ ID NO: 41) | 525.3 | 2 | 831.4 | 1 | y8 | 0.671 |
| | | LELLSLSK | (SEQ ID NO: 42) | 451.8 | 2 | 243.1 | 1 | b2 | 0.837 |

TABLE 16-2

| N. | Protein name | Peptide Sequence | SEQ ID NO | Precursor Mz | Precursor Charge | Product Mz | Product Charge | Fragment Ion | AUC-value Normal vs. HCC |
|---|---|---|---|---|---|---|---|---|---|
| 12 | Versican core protein | LLASDAGLYR | (SEQ ID NO: 44) | 539.8 | 2 | 694.4 | 1 | y6 | 0.907 |
| | | TDGQVSGEAIK | (SEQ ID NO: 45) | 552.8 | 2 | 517.3 | 1 | y5 | 0.888 |
| | | VVAEDITQTSR | (SEQ ID NO: 43) | 609.8 | 2 | 514.3 | 1 | b5 | 0.608 |
| 13 | Receptor tyrosine-protein kinase erbB-3 (ERBB3) | LAEVPDLLEK | (SEQ ID NO: 47) | 563.8 | 2 | 413.2 | 1 | b4 | 0.529 |
| | | NLDVTSLGFR | (SEQ ID NO: 46) | 561.3 | 2 | 543.3 | 1 | b5 | 0.851 |
| 14 | Coagulation factor V (F5) | ASEFLGYWEPR | (SEQ ID NO: 49) | 677.8 | 2 | 272.2 | 1 | y2 | 0.763 |
| | | TWDQSIALR | (SEQ ID NO: 48) | 545.3 | 2 | 731.3 | 1 | b6 | 0.655 |
| 15 | Coagulation factor XI (F11) | LSSDGSPTK | (SEQ ID NO: 50) | 446.2 | 2 | 691.3 | 1 | y7 | 0.947 |
| | | VVSGFSLK | (SEQ ID NO: 51) | 418.7 | 2 | 286.2 | 1 | b3 | 0.936 |
| 16 | Follistatin-related protein 1 | GSDYSEILDK | (SEQ ID NO: 52) | 563.8 | 2 | 867.4 | 1 | y7 | 0.755 |
| | | LSFQEFLK | (SEQ ID NO: 53) | 506.3 | 2 | 201.1 | 1 | b2 | 0.593 |
| 17 | N-acetylglucosamine-6-sulfatase (GNS) | AFQNVFAPR | (SEQ ID NO: 55) | 525.3 | 2 | 343.2 | 1 | y3 | 0.914 |
| | | YYDYTLSINGK | (SEQ ID NO: 54) | 668.8 | 2 | 732.4 | 1 | y7 | 0.781 |
| 18 | G-protein coupled receptor 126 (GPR126) | ISVVIQNILR | (SEQ ID NO: 57) | 577.9 | 2 | 515.3 | 1 | y4 | 0.703 |
| | | SLSSSSIGSDSTYLTSK | (SEQ ID NO: 56) | 860.4 | 2 | 1008.4 | 1 | b11 | 0.708 |
| | | VILPQTSDAYQVSVAK | (SEQ ID NO: 58) | 860.0 | 2 | 404.3 | 1 | y4 | 0.710 |
| 19 | Heparin cofactor 2 | DFVDASSK | (SEQ ID NO: 59) | 434.7 | 2 | 362.2 | 1 | b3 | 0.578 |
| | | EYYFAEAQIADFSDPAFISK | (SEQ ID NO: 60) | 1156.5 | 2 | 662.4 | 1 | y6 | 0.706 |
| | | NYNLVESLK | (SEQ ID NO: 61) | 540.3 | 2 | 802.5 | 1 | y7 | 0.918 |
| | | SVNDLYIQK | (SEQ ID NO: 62) | 540.3 | 2 | 187.1 | 1 | b2 | 0.900 |
| | | TLEAQLTPR | (SEQ ID NO: 63) | 514.8 | 2 | 814.4 | 1 | y7 | 0.894 |
| 20 | Hypoxia up-regulated protein 1 (HYOU1) | DEPGEQVELK | (SEQ ID NO: 66) | 572.3 | 2 | 260.2 | 1 | y2 | 0.711 |
| | | VFGSQDLTTVK | (SEQ ID NO: 64) | 597.8 | 2 | 519.3 | 1 | b5 | 0.936 |
| | | VIDETWAWK | (SEQ ID NO: 65) | 574.3 | 2 | 691.4 | 1 | y5 | 0.885 |
| 21 | Integrin alpha-2 (ITGA2) | FGIAVLGYLNR | (SEQ ID NO: 68) | 611.9 | 2 | 488.3 | 1 | b5 | 0.726 |
| | | YFFDVSDEAALLEK | (SEQ ID NO: 67) | 823.9 | 2 | 1189.6 | 1 | y11 | 0.771 |
| 22 | Integrin alpha-3 (ITGA3) | DITIVTGAPR | (SEQ ID NO: 69) | 521.8 | 2 | 501.3 | 1 | y5 | 0.825 |
| | | TVEDVGSPLK | (SEQ ID NO: 70) | 522.8 | 2 | 201.1 | 1 | b2 | 0.530 |
| 23 | Integrin alpha-6 (ITGA6) | LPNAGTQVR | (SEQ ID NO: 72) | 478.3 | 2 | 396.2 | 1 | b4 | 0.704 |
| | | LWDSTFLEEYSK | (SEQ ID NO: 71) | 759.4 | 2 | 915.4 | 1 | y7 | 0.588 |
| 24 | Integrin alpha-M (ITGAM) | EFDVTVTVR | (SEQ ID NO: 73) | 533.3 | 2 | 491.2 | 1 | b4 | 0.540 |
| | | ILVVITDGEK | (SEQ ID NO: 74) | 543.8 | 2 | 425.3 | 1 | b4 | 0.916 |
| 25 | Integrin beta-2 (ITGB2) | ALNEITESGR | (SEQ ID NO: 76) | 545.3 | 2 | 662.3 | 1 | y6 | 0.912 |
| | | LTDNSNQFQTEVGK | (SEQ ID NO: 75) | 790.9 | 2 | 661.4 | 1 | y6 | 0.660 |
| | | YLIYVDESR | (SEQ ID NO: 103) | 579.3 | 2 | 506.2 | 1 | y4 | 0.726 |
| 26 | Plasma kallikrein (KLKB1) | DSVTGTLPK | (SEQ ID NO: 78) | 459.3 | 2 | 244.2 | 1 | y2 | 0.847 |
| | | GVNFDVSK | (SEQ ID NO: 77) | 433.2 | 2 | 709.4 | 1 | y6 | 0.917 |
| | | IAYGTQGSSGYSLR | (SEQ ID NO: 79) | 730.4 | 2 | 826.4 | 1 | y8 | 0.857 |
| | | YSPGGTPTAIK | (SEQ ID NO: 80) | 546.3 | 2 | 841.5 | 1 | y9 | 0.912 |
| 27 | Kinectin (KTN1) | LQTLVSEQPNK | (SEQ ID NO: 82) | 628.8 | 2 | 242.1 | 1 | b2 | 0.941 |
| | | TEDSSLTK | (SEQ ID NO: 81) | 440.7 | 2 | 520.2 | 1 | b5 | 0.634 |
| 28 | Lysosome-associated membrane glycoprotein 2 | GILTVDELLAIR | (SEQ ID NO: 84) | 656.9 | 2 | 472.3 | 1 | y4 | 0.693 |
| | | VQPFDVTQGK | (SEQ ID NO: 83) | 559.8 | 2 | 587.3 | 1 | b5 | 0.909 |
| 29 | Galectin-3-binding protein (LGALS3BP) | ALGFFDATQALGR | (SEQ ID NO: 85) | 674.8 | 2 | 960.5 | 1 | y9 | 0.920 |
| | | ELSEALGQIFDSQR | (SEQ ID NO: 86) | 796.9 | 2 | 950.5 | 1 | y8 | 0.914 |
| | | SDLAVPSELALLK | (SEQ ID NO: 87) | 678.4 | 2 | 870.5 | 1 | y8 | 0.898 |
| | | YSSDYFOAPSDYR | (SEQ ID NO: 88) | 799.8 | 2 | 338.2 | 1 | y2 | 0.883 |
| 30 | Plexin-A1 (PLXNA1) | LSLPWLLNK | (SEQ ID NO: 90) | 542.3 | 2 | 314.2 | 1 | b3 | 0.547 |
| | | YDYTEDPTILR | (SEQ ID NO: 89) | 693.3 | 2 | 714.4 | 1 | y6 | 0.949 |
| 31 | Periostin (POSTN) | EVDDTLLVNELK | (SEQ ID NO: 91) | 694.4 | 2 | 602.4 | 1 | y5 | 0.614 |
| | | IIDGVPVEITEK | (SEQ ID NO: 92) | 656.9 | 2 | 1086.6 | 1 | y10 | 0.914 |
| 32 | Inactive tyrosine-protein kinase 7 (PTK7) | SADASFNIK | (SEQ ID NO: 93) | 476.7 | 2 | 679.4 | 1 | y6 | 0.762 |
| | | SSLQPITTLGK | (SEQ ID NO: 94) | 572.8 | 2 | 416.2 | 1 | b4 | 0.815 |
| 33 | Roundabout homolog 4 | DLSQSPGAVPQALVAWR | (SEQ ID NO: 95) | 898.0 | 2 | 715.4 | 1 | y6 | 0.516 |
| | | GPDSNVLLLR | (SEQ ID NO: 96) | 542.3 | 2 | 514.4 | 1 | y4 | 0.909 |
| 34 | Tenascin (TNC) | APTAQVESFR | (SEQ ID NO: 98) | 553.3 | 2 | 765.4 | 1 | y6 | 0.777 |
| | | LLETVEYDISGAER | (SEQ ID NO: 97) | 797.9 | 2 | 556.1 | 1 | b5 | 0.888 |
| 35 | Vitronectin (VTN) | DGSLFAFR | (SEQ ID NO: 99) | 456.7 | 2 | 540.3 | 1 | y4 | 0.705 |
| | | DVWGIEGPIDAAFTR | (SEQ ID NO: 100) | 823.9 | 2 | 458.2 | 1 | b4 | 0.774 |
| | | FEDGVLDPDYPR | (SEQ ID NO: 101) | 711.8 | 2 | 647.3 | 1 | y5 | 0.712 |

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention.

What is claimed is:

1. A method of diagnosing a liver cancer in a subject or a sample in need thereof comprising the steps of:
   providing a biological sample from the subject comprising proteins having a N-linked glycosylation motif;
   de-glycosylating the proteins comprised in the sample;
   fragmenting the de-glycosylated proteins to obtain de-glycosylated peptides comprising the N-linked motif, and non-glycosylated peptides comprising a non-glycosylated motif and which do not comprise the N-linked motif;
   determining in the fragmented proteins an amount of the de-glycosylated peptide at the N-linked motif and the amount of a non-glycosylated peptide which does not contain the N-linked motif and a ratio of the amount of the de-glycosylated peptide to the non-glycosylated peptide; and
   diagnosing the subject or the sample as the cancer or susceptible to the cancer if the ratio is changed in the subject or in the sample compared to that of a control,
   wherein the proteins, the peptide fragments from the proteins which are de-glycosylated at the N-linked glycosylation motif, the de-glycosylated peptide and the non-glycosylated peptide of the proteins are at least one as listed in Table 1; and the amount is determined using a LC-MS obtained by SIM (Selected Ion Monitoring) or MRM (Multiple reaction monitoring).

2. The method of claim 1, wherein the de-glycosylation is performed by using a PNGase-F.

3. The method of claim 1, wherein the fragmentation is performed by treating the sample with at least one of a trypsin, a lysine-C, an arginine-C or an aspartic acid N.

4. The method of claim 1, wherein the sample is selected from the group consisting of a cell, a whole blood, a serum, a plasma, a saliva, a urine, a follicular fluid, a breast milk and a pancreatin.

5. The method of claim 1, wherein the protein having an N-linked motif is an AFP (alpha feto protein), the de-glycosylated peptide is VDFTEIQK (SEQ ID NO:9), and the non-glycosylated peptide is GYQELLEK (SEQ ID NO:10) in Table 1.

6. The method of claim 1, wherein the determination of the amount using the MRM is performed by monitoring a m/z value and optimized collision energy as described in the table below:

| Protein name | Peptide sequence | Precursor ion (m/z) | Product ion (m/z) | Optimized collision energy (volt) | Ion type |
|---|---|---|---|---|---|
| Alpha-fetoprotein (AFP) | VDFTEIQK (SEQ ID NO: 9) | 490.258382 | 880.441074 | 13.3 | y7 |
| | | 490.258382 | 765.414131 | 18.3 | y6 |
| | | 490.258382 | 818.845717 | 15.3 | y5 |
| | | 490.258382 | 517.298038 | 11.3 | y4 |
| | | 490.258382 | 388.255445 | 21.3 | y3 |
| | | 490.258382 | 275.171381 | 21.3 | y2 |
| | | 490.258382 | 362.171047 | 9.3 | b3 |
| | | 490.258382 | 468.218725 | 9.3 | b4 |
| | | 490.258382 | 592.261319 | 11.3 | b5 |
| | | 490.258382 | 705.345388 | 9.8 | b6 |
| | | 490.258382 | 833.40396 | 7.3 | b7 |
| | GYQELLEK (SEQ ID NO: 10) | 490.258382 | 759.424696 | 11.9 | y6 |
| | | 490.258382 | 631.366118 | 18.3 | y5 |
| | | 490.258382 | 502.323525 | 15.3 | y4 |
| | | 490.258382 | 389.239481 | 17.3 | y3 |
| | | 490.258382 | 276.155397 | 21.3 | y2 |
| | | 490.258382 | 221.092088 | 11.3 | b2 |
| | | 490.258382 | 349.150646 | 9.3 | b3 |
| | | 490.258382 | 591.277303 | 11.3 | b5 |
| | | 490.258382 | 704.361367 | 7.3 | b6 |
| | | 490.258382 | 833.40396 | 9.3 | b7 |

* * * * *